US008080417B2

(12) United States Patent
Peled et al.

(10) Patent No.: US 8,080,417 B2
(45) Date of Patent: Dec. 20, 2011

(54) METHODS OF EX VIVO HEMATOPOIETIC STEM CELL EXPANSION BY CO-CULTURE WITH MESENCHYMAL CELLS

(75) Inventors: Tony Peled, Mevaseret Zion (IL); Arik Hasson, Kiryat-Ono (IL)

(73) Assignee: Gamida-Cell Ltd., Jerusalem (IL)

( * ) Notice: Subject to any disclaimer, the term of this patent is extended or adjusted under 35 U.S.C. 154(b) by 213 days.

(21) Appl. No.: 11/606,525

(22) Filed: Nov. 29, 2006

(65) Prior Publication Data
US 2007/0077652 A1 Apr. 5, 2007

Related U.S. Application Data

(63) Continuation of application No. PCT/IL2005/000994, filed on Sep. 15, 2005.

(60) Provisional application No. 60/610,171, filed on Sep. 16, 2004.

(51) Int. Cl.
*C12N 5/00* (2006.01)
(52) U.S. Cl. ........ 435/373; 435/377; 435/325; 424/93.7
(58) Field of Classification Search .................... None
See application file for complete search history.

(56) References Cited

U.S. PATENT DOCUMENTS

| | | |
|---|---|---|
| 3,687,808 A | 8/1972 | Merigan, Jr. et al. |
| 3,715,345 A | 2/1973 | Smith |
| 3,791,932 A | 2/1974 | Schuurs et al. ........ 195/103.5 R |
| 3,839,153 A | 10/1974 | Schuurs et al. ........ 195/103.5 R |
| 3,850,578 A | 11/1974 | McConnell ................ 23/230 B |
| 3,850,752 A | 11/1974 | Schuurs et al. ........ 195/103.5 R |
| 3,853,987 A | 12/1974 | Dreyer ............................. 424/1 |
| 3,863,008 A | 1/1975 | Grant |
| 3,867,517 A | 2/1975 | Ling ............................... 424/1 |
| 3,876,623 A | 4/1975 | Jackson et al. |
| 3,879,262 A | 4/1975 | Schuurs et al. ................. 195/63 |
| 3,901,654 A | 8/1975 | Gross ......................... 23/230 B |
| 3,935,074 A | 1/1976 | Rubenstein et al. ... 195/103.5 R |
| 3,984,533 A | 10/1976 | Uzgiris ........................... 424/12 |
| 3,996,345 A | 12/1976 | Ullman et al. ................. 424/12 |
| 4,034,074 A | 7/1977 | Miles ............................. 424/1 |
| 4,036,945 A | 7/1977 | Haber |
| 4,098,876 A | 7/1978 | Piasio et al. .................... 424/1 |
| 4,331,647 A | 5/1982 | Goldenberg |
| 4,469,863 A | 9/1984 | Ts'o et al. |
| 4,476,301 A | 10/1984 | Imbach et al. |
| 4,642,120 A | 2/1987 | Nevo et al. |
| 4,666,828 A | 5/1987 | Gusella ........................... 435/6 |
| 4,683,202 A | 7/1987 | Mullis ........................... 435/91 |
| 4,687,808 A | 8/1987 | Jarrett et al. |
| 4,801,531 A | 1/1989 | Frossard ......................... 435/6 |
| 4,806,484 A | 2/1989 | Petrossian et al. |
| 4,816,567 A | 3/1989 | Cabilly et al. |
| 4,866,052 A | 9/1989 | Hider et al. |
| 4,868,116 A | 9/1989 | Morgan et al. |
| 4,879,219 A | 11/1989 | Wands et al. ..................... 435/7 |
| 4,946,778 A | 8/1990 | Ladner et al. |
| 4,980,286 A | 12/1990 | Morgan et al. |
| 5,011,771 A | 4/1991 | Bellet et al. ................ 435/7.94 |
| 5,013,830 A | 5/1991 | Ohtsuka et al. |
| 5,023,243 A | 6/1991 | Tullis |
| 5,034,506 A | 7/1991 | Summerton et al. |
| 5,081,035 A | 1/1992 | Halberstadt et al. |
| 5,149,797 A | 9/1992 | Pederson et al. |
| 5,166,315 A | 11/1992 | Summerton et al. |
| 5,166,320 A | 11/1992 | Wu et al. |
| 5,177,196 A | 1/1993 | Meyer, Jr. et al. |
| 5,185,444 A | 2/1993 | Summerton et al. |
| 5,188,897 A | 2/1993 | Suhadolnik et al. |
| 5,192,659 A | 3/1993 | Simons ............................. 435/6 |
| 5,214,134 A | 5/1993 | Weis et al. |
| 5,216,141 A | 6/1993 | Benner |
| 5,220,007 A | 6/1993 | Pederson et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,272,057 A | 12/1993 | Smulson et al. .................. 435/6 |
| 5,276,019 A | 1/1994 | Cohen et al. |
| 5,278,302 A | 1/1994 | Caruthers et al. |
| 5,281,521 A | 1/1994 | Trojanowski et al. ......... 435/7.5 |
| 5,286,717 A | 2/1994 | Cohen et al. |
| 5,320,963 A | 6/1994 | Knaack et al. |
| 5,321,131 A | 6/1994 | Agrawal et al. |

(Continued)

FOREIGN PATENT DOCUMENTS

AU          759 522          8/1999

(Continued)

OTHER PUBLICATIONS

Mulloy et al, Blood 2003, vol. 102, No. 13, pp. 4369-4376.*
Roach, ML and McNeish, JD. "Methods for the Isolation and Maintenance of Murine Embryonic Stem Cells". Methods in Molecular Biology, vol. 185: Embryonic Stem Cells: Methods and Protocols. Ed. K Turksen. Totowa, NJ: Humana Press Inc, 2002. 1-16.*
Chen et al, "Differentiation of rat marrow mesenchymal stem cells into pancreatic islet beta-cells" World J Gastroenterol (2004) 10(20): 3016-3020.*
Ku et al, "Committing Embryonic Stem Cells to Early Endocrine Pancreas In Vitro" Stem Cells (2004) 22: 1205-1217.*
Lee et al, "Clonal Expansion of Adult Rat Hepatic Stem Cell Lines by Suppression of Asymmetric Cell Kinetics (SACK)" Biotechnology and Bioengineering, (2003) 83: 760-771.*
Roberts, I "Mesenchymal Stem Cells" Vox Sanguinis (Jul. 2004) 87 (Suppl 2): s38-s41.*
Zhang et al, "Human placenta-derived mesenchymal progenitor cells support culture expansion of long-term culture-initiating cells from cord blood CD34+ cells" Experimental Hematology, Jul. 2004, vol. 32, pp. 657-664.*

(Continued)

*Primary Examiner* — Allison Ford
(74) *Attorney, Agent, or Firm* — Mintz Levin Cohn Ferris Glovsky and Popeo, P.C.; Ivor R. Elrifi; Matthew Pavao

(57) ABSTRACT

Methods of ex-vivo expansion and at the same time inhibiting differentiation of stem cells by co-culture with mesenchymal cells, transplantable populations of renewable progenitor and stem cells expanded thereby, and their uses in therapeutic applications.

33 Claims, No Drawings

U.S. PATENT DOCUMENTS

| | | |
|---|---|---|
| 5,342,781 A | 8/1994 | Su |
| 5,366,878 A | 11/1994 | Pedersen et al. |
| 5,378,725 A | 1/1995 | Bonjouklian et al. |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,434,257 A | 7/1995 | Matteucci et al. |
| 5,437,994 A | 8/1995 | Emerson et al. |
| 5,453,496 A | 9/1995 | Caruthers et al. |
| 5,455,233 A | 10/1995 | Spielvogel et al. |
| 5,466,677 A | 11/1995 | Baxter et al. |
| 5,470,967 A | 11/1995 | Huie et al. |
| 5,476,925 A | 12/1995 | Letsinger et al. |
| 5,480,906 A | 1/1996 | Creemer et al. |
| 5,486,359 A | 1/1996 | Caplan et al. |
| 5,489,677 A | 2/1996 | Sanghvi et al. |
| 5,491,133 A | 2/1996 | Walder et al. |
| 5,504,103 A | 4/1996 | Bonjouklian et al. |
| 5,519,126 A | 5/1996 | Hecht |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,545,806 A | 8/1996 | Lonberg et al. |
| 5,545,807 A | 8/1996 | Surani et al. |
| 5,550,111 A | 8/1996 | Suhadolnik et al. |
| 5,561,225 A | 10/1996 | Maddry et al. |
| 5,563,253 A | 10/1996 | Agrawal et al. |
| 5,565,350 A | 10/1996 | Kmiec |
| 5,569,825 A | 10/1996 | Lonberg et al. |
| 5,571,799 A | 11/1996 | Tkachuk et al. |
| 5,587,361 A | 12/1996 | Cook et al. |
| 5,596,086 A | 1/1997 | Matteucci et al. |
| 5,602,240 A | 2/1997 | De Mesmaeker et al. |
| 5,608,046 A | 3/1997 | Cook et al. |
| 5,610,289 A | 3/1997 | Cook et al. |
| 5,612,211 A | 3/1997 | Wilson et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,625,126 A | 4/1997 | Lonberg et al. |
| 5,631,219 A | 5/1997 | Rosenthal et al. |
| 5,633,360 A | 5/1997 | Bischofberger et al. |
| 5,633,425 A | 5/1997 | Lonberg et al. |
| 5,652,355 A | 7/1997 | Metelev et al. |
| 5,652,356 A | 7/1997 | Agrawal |
| 5,654,186 A | 8/1997 | Cerami et al. |
| 5,661,016 A | 8/1997 | Lonberg et al. |
| 5,663,312 A | 9/1997 | Chaturvedula |
| 5,674,750 A | 10/1997 | Kraus et al. |
| 5,677,437 A | 10/1997 | Teng et al. |
| 5,677,439 A | 10/1997 | Weis et al. |
| 5,700,922 A | 12/1997 | Cook |
| 5,712,154 A | 1/1998 | Mullon et al. |
| 5,714,331 A | 2/1998 | Buchardt et al. |
| 5,716,411 A | 2/1998 | Orgill et al. |
| 5,716,616 A | 2/1998 | Prockop et al. |
| 5,719,262 A | 2/1998 | Buchardt et al. |
| 5,733,541 A | 3/1998 | Taichman et al. |
| 5,736,396 A | 4/1998 | Bruder et al. |
| 5,741,899 A | 4/1998 | Capon et al. |
| 5,770,378 A | 6/1998 | Hwang et al. |
| 5,770,580 A | 6/1998 | Ledley et al. |
| 5,776,699 A | 7/1998 | Klein et al. |
| 5,789,245 A | 8/1998 | Dubensky, Jr. et al. |
| 5,789,543 A | 8/1998 | Ingham et al. |
| 5,792,751 A | 8/1998 | Ledley et al. |
| 5,814,482 A | 9/1998 | Dubensky, Jr. et al. |
| 5,830,760 A | 11/1998 | Tsai et al. |
| 5,837,544 A | 11/1998 | Capon et al. |
| 5,843,723 A | 12/1998 | Dubensky, Jr. et al. |
| 5,844,079 A | 12/1998 | Ingham et al. |
| 5,851,832 A | 12/1998 | Weiss et al. |
| 5,851,984 A | 12/1998 | Matthews et al. |
| 5,877,207 A | 3/1999 | Klein et al. |
| 5,945,309 A | 8/1999 | Ni et al. |
| 5,945,337 A | 8/1999 | Brown |
| 5,952,345 A | 9/1999 | Klein et al. |
| 5,958,954 A | 9/1999 | Klein et al. |
| 5,990,329 A | 11/1999 | Klaus et al. |
| 6,008,204 A | 12/1999 | Klein et al. |
| 6,015,686 A | 1/2000 | Dubensky, Jr. et al. |
| 6,015,694 A | 1/2000 | Dubensky, Jr. et al. |
| 6,063,797 A | 5/2000 | Fesus et al. |
| 6,077,947 A | 6/2000 | Capon et al. |
| 6,090,810 A | 7/2000 | Klein et al. |
| 6,117,850 A | 9/2000 | Patchen et al. |
| 6,130,230 A | 10/2000 | Chambon et al. |
| 6,133,309 A | 10/2000 | Bollag et al. |
| 6,165,747 A | 12/2000 | Ingham et al. |
| 6,218,128 B1 | 4/2001 | Klein et al. |
| 6,228,848 B1 | 5/2001 | Klein et al. |
| 6,232,291 B1 | 5/2001 | Ni et al. |
| 6,255,112 B1 | 7/2001 | Thiede et al. |
| 6,261,786 B1 | 7/2001 | Marigo et al. |
| 6,270,964 B1 | 8/2001 | Michnick et al. |
| 6,271,363 B1 | 8/2001 | Ingham et al. |
| 6,284,540 B1 | 9/2001 | Milbrandt et al. |
| 6,294,330 B1 | 9/2001 | Michnick et al. |
| 6,303,374 B1 | 10/2001 | Zhang et al. |
| 6,306,575 B1 | 10/2001 | Thomas et al. |
| 6,326,174 B1 | 12/2001 | Joyce et al. |
| 6,326,198 B1 | 12/2001 | Emerson et al. |
| 6,329,169 B1 | 12/2001 | Ni et al. |
| 6,335,195 B1 | 1/2002 | Rodgers et al. |
| 6,338,942 B2 | 1/2002 | Kraus et al. |
| 6,342,219 B1 | 1/2002 | Thorpe et al. |
| 6,342,221 B1 | 1/2002 | Thorpe et al. |
| 6,342,372 B1 | 1/2002 | Dubensky, Jr. et al. |
| 6,342,581 B1 | 1/2002 | Rosen et al. |
| 6,372,210 B2 | 4/2002 | Brown |
| 6,372,473 B1 | 4/2002 | Moore et al. |
| 6,376,236 B1 | 4/2002 | Dubensky, Jr. et al. |
| 6,384,192 B1 | 5/2002 | Ingham et al. |
| 6,413,772 B1 | 7/2002 | Block |
| 6,413,773 B1 | 7/2002 | Ptasznik et al. |
| 6,642,019 B1 | 11/2003 | Anderson et al. |
| 6,645,489 B2 | 11/2003 | Pykett et al. |
| 6,680,166 B1 | 1/2004 | Mullon et al. |
| 6,887,704 B2 | 5/2005 | Peled et al. |
| 6,962,698 B1 | 11/2005 | Peled et al. |
| 7,169,605 B2 | 1/2007 | Peled et al. |
| 7,247,477 B2 | 7/2007 | Itskovitz-Eldor et al. |
| 7,344,881 B2 | 3/2008 | Peled et al. |
| 2001/0014475 A1 | 8/2001 | Frondoza et al. |
| 2002/0001826 A1 | 1/2002 | Wager et al. |
| 2002/0090603 A1 | 7/2002 | Lipton et al. |
| 2002/0114784 A1 | 8/2002 | Li et al. |
| 2002/0114789 A1 | 8/2002 | Peled et al. |
| 2002/0146678 A1 | 10/2002 | Benvenisty |
| 2002/0146816 A1 | 10/2002 | Vellinger et al. |
| 2002/0159981 A1 | 10/2002 | Peled et al. |
| 2002/0182035 A1 | 12/2002 | Ramiya et al. |
| 2003/0002363 A1 | 1/2003 | Le et al. |
| 2003/0031665 A1 | 2/2003 | Dang et al. ............... 424/141.1 |
| 2003/0113913 A1 | 6/2003 | Purton et al. |
| 2003/0125410 A1 | 7/2003 | Keita et al. |
| 2003/0149074 A1 | 8/2003 | Melese et al. |
| 2003/0215445 A1 | 11/2003 | Serrero |
| 2003/0235909 A1 | 12/2003 | Hariri et al. |
| 2004/0076603 A1 | 4/2004 | Peled et al. |
| 2004/0247574 A1 | 12/2004 | Christopherson, II et al. ............... 424/93.7 |
| 2005/0008624 A1 | 1/2005 | Peled et al. ............... 424/93.21 |
| 2005/0031595 A1 | 2/2005 | Peled et al. |
| 2005/0054097 A1 | 3/2005 | Peled et al. ............... 435/372 |
| 2005/0054103 A1 | 3/2005 | Peled et al. |
| 2005/0069527 A1 | 3/2005 | Laughlin et al. |
| 2005/0084961 A1 | 4/2005 | Hedrick et al. |
| 2005/0095228 A1 | 5/2005 | Fraser et al. |
| 2005/0118150 A1 | 6/2005 | Peled et al. |
| 2005/0214262 A1 | 9/2005 | Peled et al. |
| 2005/0220774 A1 | 10/2005 | Peled et al. |
| 2006/0171932 A1 | 8/2006 | Hendricks et al. |
| 2006/0205071 A1 | 9/2006 | Hasson et al. |

| | | | |
|---|---|---|---|
| 2007/0077652 | A1 | 4/2007 | Peled et al. |
| 2008/0279828 | A1 | 11/2008 | Peled et al. |
| 2010/0061963 | A1 | 3/2010 | Peled |

FOREIGN PATENT DOCUMENTS

| | | |
|---|---|---|
| AU | 770 896 | 6/2000 |
| EP | 0 331 464 | 9/1989 |
| EP | 1 332 673 | 8/2003 |
| EP | 1 332 676 | 8/2003 |
| EP | 1 332 673 | 6/2004 |
| EP | 1424389 A1 | 6/2004 |
| WO | WO 89/02468 | 3/1989 |
| WO | WO 89/05345 | 6/1989 |
| WO | WO 89/07136 | 8/1989 |
| WO | WO 92/07573 | 5/1992 |
| WO | WO 92/11355 | 7/1992 |
| WO | WO 93/09220 | 5/1993 |
| WO | WO 93/18132 | 9/1993 |
| WO | WO 94/18991 | 9/1994 |
| WO | WO 95/14078 | 5/1995 |
| WO | WO 95/21911 | 8/1995 |
| WO | WO 95/24464 | 9/1995 |
| WO | WO 96/01108 | 1/1996 |
| WO | WO 96/40876 | 12/1996 |
| WO | WO 97/04707 | 2/1997 |
| WO | WO 97/31647 | 9/1997 |
| WO | WO 97/33978 | 9/1997 |
| WO | WO 97/41209 | 11/1997 |
| WO | WO 97/41224 | 11/1997 |
| WO | WO 98/25634 | 6/1998 |
| WO | WO 99/07831 | 2/1999 |
| WO | WO 99/18885 | 4/1999 |
| WO | WO 99/40783 | 8/1999 |
| WO | WO 99/64566 | 12/1999 |
| WO | WO 00/18885 | 4/2000 |
| WO | WO 00/30635 | 6/2000 |
| WO | WO 00/46349 | 8/2000 |
| WO | WO 00/66712 | 11/2000 |
| WO | WO 00/73421 | 12/2000 |
| WO | WO 02/064755 | 8/2002 |
| WO | WO 02/080995 | 10/2002 |
| WO | WO 03/004626 | 1/2003 |
| WO | WO 03/062369 * | 7/2003 |
| WO | WO 03/062404 | 7/2003 |
| WO | WO 03/072557 | 9/2003 |
| WO | WO 03/078567 | 9/2003 |
| WO | WO 2004/016731 | 2/2004 |
| WO | WO 2004/078917 | 9/2004 |
| WO | WO 2005/007073 A2 | 1/2005 |
| WO | WO 2005/007799 | 1/2005 |
| WO | WO-2005007799 A2 | 1/2005 |
| WO | WO 2005/086845 A2 | 9/2005 |
| WO | WO 2006/030442 A2 | 3/2006 |
| WO | WO 2007/063545 | 6/2007 |
| WO | WO 2008/056368 | 5/2008 |
| WO | WO-08056368 A2 | 5/2008 |

OTHER PUBLICATIONS

Aiuti et al. "The Chemokine SDF-1 Is a Chemoattractant for Human CD34+ Hematopoietic Progenitor Cells and Provides a New Mechanism to Explain the Mobilization of CD34+ Progenitors to Peripheral Blood", Journal of Experimental Medicine, 185(1): 111-120, 1997.
Anderlini et al. "The Use of Mobilized Peripheral Blood Stem Cells From Normal Donors for Allografting", Stem Cells, 15: 9-17, 1997.
Arriero et al. "Adult Skeletal Muscle Stem Cells Differentiate Into Endothelial Lineage and Ameliorate Renal Dysfunction After Acute Ischemia", American Journal of Physiology—Renal Physiology, 287: F621-F627, 2004.
Baggiolini "Chemokines and Leukocyte Traffic", Nature, 392: 565-568, 1998.
Banasik et al. "Specific Inhibitors of Poly(ADP-Ribose) Synthetase and Mono(ADP-Ribosyl)Transferase", The Journal of Biological Chemistry, 267(3): 1569-1575, 1992.
Bernhard et al. Generation of Immunostimulatory Dendritic Cells From Human CD34+ Hematopoietic Progenitor Cells of the Bone Maroow and Peripheral Blood, Cancer Research, 55: 1099-1104, 1995.

Bohmer et al. "Fetal Cell Isolation From Maternal Blood Cultures by Flow Cytometric Hemoglobin Profiles", Fetal Diagnosis and Therapy, 17(2): 83-89, 2002.
Bongers et al. "Kinetics of Dipeptyl Peptidase IV Proteolysis of Growth Hormone-Releasing Factor and Analogs", Biochimica et Biophysica Acta, 1122: 147-153, 1992.
Broxmeyer "Regulation of Hematopoiesis by Chemokine Family Members", International Journal of Hematology, 74: 9-17, 2001.
Brugger et al. "Reconstitution of Hematopoiesis After High-Dose Chemotherapy by Autologous Progenitor Cells Generated Ex Vivo", New England Journal of Medicine, 333(5): 283-287, 1995.
Christopherson II et al. "Cell Surface Peptidase CD26/Dipeptidylpeptidase IV Regulates CXCL12/Stromal Cell-Derived Factor-1α-Mediated Chemotaxis of Human Cord Blood CD34+ Progenitor Cells", The Journal of Immunology, 169: 7000-7008, 2002.
Christopherson II et al. "Modulation of Hematopoietic Stem Cell Homing and Engraftment by CD26", Science, 305: 1000-1003, 2004.
Corda et al. "Functional Aspects of Protein Mono-ADP-Ribosylation", The EMBO Journal, 22(9): 1953-1958, 2003.
Czyz et al. "Potential of Embryonic and Adult Stem Cell In Vitro", Biological Chemistry, 384: 1391-1409, 2003.
De La Cruz et al. "Do Protein Motifs Read the Histone Code?", BioEssays, 27.2: 164-175, 2005.
Donovan et al. "The End of the Beginning for Pluripotent Stem Cells", Nature, 414(6859): 92-97, 2001.
Emerson "Ex Vivo Expansion of Hematopoietic Precursors, Progenitors, and Stem Cells: The Next Generation of Cellular Therapeutics", Blood, 87(8): 3082-3088, 1996.
Ferrari et al. "Muscle Regeneration by Bone Marrow-Derived Myogenic Progenitors", Science, 279(5356): 1528-1530, 1998. Erratum in: Science, 281(5379): 923, 1998.
Fisch et al. "Generation of Antigen-Presenting Cells for Soluble Protein Antigens Ex Vivo From Peripheral Blood CD34+ Hematopoietic Progenitor Cells in Cancer Patients", European Journal of Immunology, 26: 595-600, 1996.
Freedman et al. "Generation of Human T Lymphocytes From Bone Marrow CD34+ Cells In Vitro", Nature Medicine, 2(1): 46-51, 1995.
Gluckman et al. "Hematopoietic Reconstitution in a Patient With Fanconi's Anemia by Means of Umbilical-Cord Blood From an HLA-Identical Sibling", The New England Journal of Medicine, 321(17): 1174-1178, 1989.
Heslop et al. "Long-Term Restoration of Immunity Against Epstein-Barr Virus Infection by Adoptive Transfer of Gene-Modified Virus-Specific T Lymphocytes", Nature Medicine, 2(5): 551-555, 1996.
Hühn et al. "Molecular Analysis of CD26-Mediated Signal Transduction in T Cells", Immunology Letters, 72: 127-132, 2000.
Imai et al. "Selective Secretion of Chemoattractants for Haemapoietic Progenitor Cells by Bone Marrow 25Endothelial Cells: A Possible Role in Homing of Haemopoietic Progenitor Cells to Bone Marrow", British Journal of Haematology, 106: 905-911, 1999.
Imitola et al. "Directed Migration of Neural Stem Cells to Sites of CNS Injury by the Stroman Cell-Derived Factor 1α/CXC Chemokine Receptor 4 Pathway", Proc. Natl. Acad. Sci. USA, 101(52): 18117-18122, 2004.
Jackson et al. "Regeneration of Ischemic Cardiac Muscle and Vascular Endothelium by Adult Stem Cells", The Journal of Clinical Investigation, 107(11): 1395-1402, 2001.
Koller et al. "Large-Scale Expansion of Human Stem and Progenitor Cells From Bone Marrow Mononuclear Cells in Continous Perfusion Cultures", Blood, 82(2): 378-384, 1993.
Lambeir et al. "Kinetic Investigation of Chemokine Truncation by CD26/DipeptidylPeptidase IV Reveals a Striking Selectivity Within the Chemokine Family", The Journal of Biological Chemistry, 276(32): 29839-29845, 2001.
Lebkowski et al. "Rapid Isolation and Serum-Free Expansion of Human CD34+ Cells", Blood Cells, 20: 404-410, 1994.
Lee et al. "Repair of Ischemic Heart Disease With Novel Bone Marrow-Derived Multipotent Stem Cells", Cell Cycle, 4(7): 861-864, 2005.
Lupi et al. "Endogenous ADP-Ribosylation of the G Protein β Subunit Prevents the Inhibition of Type 1 Adenylyl Cyclase", The Journal of Biological Chemistry, 275(13): 9418-9424, 2000.

McGrath et al. "Embryonic Expression and Function of the Chemokine SDF-1 and Its Receptor, CXCR4", Developmental Biology, 213: 442-456, 1999.

Miraglia et al. "A Novel Five-Transmembrane Hematopoietic Stem Cell Antigen: Isolation, Characterization, and Molecular Clonin", Blood, 90(12): 5013-5021, 1997.

Nagaya et al. "Intravenous Administration of Mesenchymal Stem Cells Improves Cardiac Functions in Rats With Acute Myocardial Infarction Through Angiogenesis and Myogenesis", American Journal of Physiology—Heart Circulation Physiology, 287: H2670-H2676, 2004.

Orlic et al. "Bone Marrow Cells Regenerate Infarcted Myocardium", Nature, 410: 701-705, 2001.

Palmiter "Regulation of Metallothionein Genes by Heavy Metals Appears to be Mediated by a Zinc-Sensitive Inhibitor That Interacts With a Constitutively Active Transcription Factor, MTF-1", Proc. Natl. Acad. Sci. USA, 91: 1219-1223, 1994.

Peled et al. "Dependence of Human Stem Cell Engraftment and Repopulation of NOD/SCID Mice on CXCR4", Science, 283: 845-848, 1999.

Prockop et al. "Isolation and Characterization of Rapidly Self-Renewing Stem Cells From Cultures of Human Marrow Stromal Cells", Cytotherapy, 3(5): 393-396, 2001.

Protti et al. "Particulate Naturally Processed Peptides Prime a Cytotoxic Response Against Human Melanoma in Vitro", Cancer Research, 56: 1210-1213, 1996.

Rankin et al. "Quantitative Studies of Inhibitors of ADP-Ribosylation In Vitro and In Vivo", The Journal of Biological Chemistry, 264(8): 4312-4317, 1989.

Rosenberg et al. "Prospective Randomized Trial of High-Dose Interleukin-2 Alone or in Conjunction With Lymphokine-Activated Killer Cells for the Treatment of Patients With Advanced Cancer", Journal of the National Cancer Institute, 85(8): 622-632, 1993.

Rowley et al. "Isolation of CD34+ Cells From Blood Stem Cell Components Using the Baxter Isolex System", Bone Marrow Transplantation, 21: 1253-1262, 1998.

Rubinstein et al. "Processing and Cryopreservation of Placental/Umbilical Cord Blood for Unrelated Bone Marrow Reconstitution", Proc. Natl. Acad. Sci. USA, 92: 10119-10122, 1995.

Sandstrom et al. "Effects of CD34+ Cell Selection and Perfusion on Ex Vivo Expansion of Peripheral Blood Mononuclear Cells", Blood, 86(3): 958-970, 1995.

Shioda et al. "Anti-HIV-1 and Chemotactic Activities of Human Stromal Cell-Derived Factor 1α(SDF-1α) and SDF-1β Are Abolished by CD26/Dipeptidyl Peptidase IV-Mediated Cleavage", Proc. Natl. Acad. Sci. USA, 95: 6331-6336, 1998.

Siena et al. "Massive Ex Vivo Generation of Functional Dendritic Cells From Mobilized CD34+ Blood Progenitors for Anticancer Therapy", Experimental Hematology, 23: 1463-1471, 1995.

Simmons et al. "Identification of Stromal Cell Precursors in Human Bone Marrow by a Novel Monoclonal Antibody, STRO-1", Blood, 78(1): 55-62, 1991.

Smith "Embryo-Derived Stem Cells: of Mice and Men", Annual Reviews of Cell and Developmental Biology, 17: 435-462, 2001.

Smith "The World According to PARP", Trends in Biochemical Sciences, 26(3): 174-179, 2001.

Struyf et al. "Natural Truncation of RANTES Abolishes Signaling Through the CC Chemokine Receptors CCR1 and CCR3, Impairs Its Chemotactic Potency and Generates a CC Chemokine Inhibitor", European Journal Immunology, 28: 1262-1271, 1998.

Sylvester et al. "Stem Cells: Review and Update", Archives of Surgery, 139: 93-99, 2004.

Tögel et al. "Administered Mesenchymal Stem Cells Protect Against Ischemic Acute Renal Failure Through Differentiation-Independent Mechanisms", American Journal of Physiology—Renal Physiology, 289: F31-F42, 2005.

Trounson "The Derivation and Potential Use of Human Embryonic Stem Cells", Reproduction, Fertility and Development, 13: 523-532, 2001.

Tse et al. "Angiogenesis in Ischaemic Myocardium by Intramyocardial Autologous Bone Marrow Mononuclear Cell Implantation", Lancet, 361: 47-49, 2003.

Uchida et al. "Direct Isolation of Human Central Nervous System Stem Cells", Proc. Natl. Acad. Sci. USA, 97(26): 14720-14725, 2000.

Ueda et al. "ADP-Ribosylation", Annual Reviews of Biochemistry, 54: 73-100, 1985.

Van Epps et al. "Harvesting, Characterization, and Culture of CD34+ Cells From Human Bone Marrow, Peripheral Blood, and Cord Blood", Blood Cells, 20(2-3): 411-423, 1994.

Vanham et al. "Decreased Expression of the Memory Marker CD26 on Both CD4+ and CD8+ T Lymphocytes of HIV-Infected Subjects", Journal of Acquired Immune Deficiency Syndromes, 6: 749-757, 1993.

Virág et al. "The Therapeutic Potential of Poly(ADP-Ribose) Polymerase Inhbititors", Pharmacological Reviews, 54(3): 375-429, 2002.

Williams et al. "Selection and Expansion of Peripheral Blood CD34+ Cells in Autologous Stem Cell Transplantation for Breast Cancer", Blood, 87(5): 1687-1691, 1996.

Xia et al. "Surface Fucosylation of Human Cord Blood Cells Augments Binding to P-Selectin and E-Selectin and Enhances Engraftment in Bone Marrow", Blood, 104(10): 3091-3096, 2004.

Yau et al. "Endogenous Mono-ADP-Ribosylation Mediates Smooth Muscle Cell Proliferation and Migration Via Protein Kinase Induction of C-Fos Expression", European Journal of Biochemistry, 270: 101-110, 2003.

Zimmerman. et al. "Large-Scale Selection of CD34+ Peripheral Blood Progenitors and Expansion of Neutrophil Precursors for Clinical Applications", Journal of Hematotherapy, 5: 247-253, 1996.

Bieback et al., "Critical Parameters for the Isolation of Mesenchymal Stem Cells from Umbilical Cord Blood", Stem Cells, 22:625-634 (2004).

Kern et al., "Comparative Analysis of Mesenchymal Stem Cells from Bone Marrow, Umbilical Cord Blood, or Adipose Tissue", *Stem Cells*, 24:1294-1301 (2006).

Acsadi et al. "Human Dystrophin Expression in Mdx Mice After Intamuscular Injection of DNA Constructs", Nature, 352: 815-818, 1991.

Alter "Fetal Erythropoiesis in Stress Hemopoiesis", Experimental Hematology, 7(5): 200-209, 1979.

American Cancer Society "Chelation Therapy", ACS, p. 1-5, 2006.

Aoki et al. "In Vivo Transfer Efficiency of Antisense Oligonucleotides Into the Myocardium Using HVJ Liposome Method", Biochemical and Biophysical Research Communications, 231: 540-545, 1997.

Armentano et al. "Expression of Human Factor IX in Rabbit Hepatocytes by Retrovirus-Mediated Gene Transfer: Potential for Gene Therapy of Hemophilia B", Proc. Natl. Acad. Sci. USA, 87: 6141-6145, 1990.

Asahara et al., "Stem cell therapy and gene transfer for regeneration", *Gene Therapy*, 7:451-457 (2000).

Auger et al. "PDGF-Dependent Tyrosine Phosphorylation Stimulates Production of Novel Polyphosphoinositides in Intact Cells", Cell, 57: 167-175, 1989.

Avital et al. "Isolation, Characterization, and Transplantation of Bone Marrow-Derived Hepatocyte Stem Cells", Biochemical and Biophysical Research Communications, 288(1): 156-164, 2001.

Bae et al. "Copper Uptake and Intracellular Distribution During Retinoic Acid-Induced Differentiation of HL-60 Cells", Journal of Nutritional Biochemistry, Food Science and Human Nutrition Department, 5: 457-461, 1994.

Bae et al. "Retinoic Acid-Induced HL-60 Cell Differentiation Is Augmented by Copper Supplementation", The Journal of Nutrition, 123(6): 997-1002, 1993.

Banno et al. "Anemia and Neutropenia in Eldery Patients Caused by Copper Deficiency for Long-Term Eternal Nutrition", Rinsho-Ketsueki, 35: 1276-1280, 1994.

Baum et al. "Isolation of a Candidate Human Hematopoietic Stem-Cell Population", Proc. Natl. Acad. Sci. USA, 89: 2804-2808, 1992.

Belovari et al. "Differentiation of Rat Neural Tissue in a Serum-Free Embryo Culture Model Followed by In Vivo Transplantation", Croatian Medical Journal, 42(6): 611-617, 2001. Abstract.

Berardi et al. "Individual CD34+CD38lowCD19-CD10—Progenitor Cells From Human Cord Blood Generate B Lymphocytes and Granulocytes", Blood, 89(10): 3554-3564, 1997.
Berkner "Development of Adenovirus Vectors for the Expression of Heterologous Genes", BioTechniques, 6(7): 616-629, 1988.
Bertagnolo et al. "Phosphoinositide 3-Kinase Activity is Essential for all-trans-Retinoic Acid-induced Granulocytic Differentiation of HL-60 Cells", Cancer Res., 59: 542-546, 1999.
Bhatia et al. "Purification of Primitive Human Hematopoietic Cells Capable of Repopulating Immune Deficient Mice", Proc. Natl. Acad. Sci, USA, 94: 5320-5325, 1997.
Bhat-Nakshatri, et al., "Tumour necrosis factor and PI3-kinase control oestrogen receptor alpha protein level and its transrepression function", Br. J. Cancer, 90:853-859 (2004).
Bi et al. "Effect of Lactoferrin on Proliferation and Differentiation of the Jurkat Human Lymphoblastic T Cell Line", Arch. Immunol. Ther. Exp., 45(4): 315-320, 1997. Abstract.
Bird et al. "Single-Chain Antigen-Binding Proteins", Science, 242: 423-426, 1988.
Birkenkamp, et al., "An inhibitor of PI3-K differentially affects proliferation and IL-6 protein secretion in normal and leukemic myeloid cells depending on the stage of differentiation", Exp. Hematol., 28:1239-1249 (2000).
Blau et al. "Fetal Hemoglobin in Acute and Chronic Stage of Erythroid Expansion", Blood, 81(1): 227-233, 1993.
Boerner et al. "Production of Antigen-Specific Human Monoclonal Antibodies From In Vitro-Primed Human Splenocytes", The Journal of Immunology, 147(1): 86-95, 1991.
Borthwick et al. "A Comparison of Cupruretic Responses to Various Tetramines and D-Penicillamine", Journal of Laboratory and Clinical Medicine, 95(4): 575-580, 1980.
Brandt et al. "Ex Vivo Expansion of Autologous Bone Marrow CD34+ Cells With Porcine Microvascular Endothelial Cells Results in a Graft Capable of Rescuing Lethally Irradiated Baboons", Blood, 94(1): 106-113, 1999.
Brazelton et al. "From Marrow to Brain: Expression of Neuronal Phenotypes in Adult Mice", Science, 290(5497): 1775-1779, 2000. Abstract.
Breitman et al. "Induction of Differentiation of the Human Promyelocytic Leukemia Cell Line (HL-60) by Retinoic Acid", Proc. Natl. Acad. Sci., 77(5): 2936-2940, 1980.
Briddell et al. "Purification of CD34+ Cells Is Essential for Optimal Ex Vivo Expansion of Umbilical Cord Blood Cells", Journal of Hematotherapy, 6: 145-150, 1997.
Brigham et al. "Rapid Communication: In Vivo Transfection of Murine Lungs With a Functioning Prokaryotic Gene Using a Liposome Vehicle", The American Journal of the Medical Sciences, 298(4): 278-281, 1989.
Brott et al. "Flow Cytometric Characterization of Perfused Human Bone Marrow Cultures: Identification of the Major Cell Lineages and Correlation With the CFU-GM Assay", Cytometry Part A, 53A: 22-27, 2003.
Brugger et al. "Ex Vivo Expansion of Enriched Peripheral Blood CD34+ Progenitor Cells by Stem Cell Factor, Interleukin-1? (IL-1?), IL-6, IL-3, Interferon-?, and Erythropoietin", Blood, 81(10); 2579-2584, 1993.
Brugnera et al. "Cloning, Chromosomal Mapping and Characterization of the Human Metal-Regulatory Transcription Factor MTF-1", Nucleic Acids Research, 22(15): 3167-3173, 1994.
Bryder et al. "Hematopoietic Stem Cells: the paradigmatic tissue-specific stem cell." Am J Pathol., 169(2):338-46, 2006.
Burgada et al. "Synthesis of New Phosphonated Tripod Ligands as Putative New Therapeutic Agents in the Chelation Treatment of Metal Intoxications", European Journal of Organic Chemistry, p. 349-352, 2001.
Buskin et al. "Identification of a Myocyte Nuclear Factor That Binds to the Muscle-Specific Enhancer of the Mouse Muscle Creatine Kinase Gene", Molecular and Cellular Biology, 9(6): 2627-2640, 1989.
Butt "Introduction to Chemical Reactor Theory", Reaction Kinetics and Reactor Design, Chap.4: 184-241, 1980.

Cable et al. "Exposure of Primary Rat Hepatocytes in Long-Term DMSO Culture to Selected Transition Metals Induces Hepatocyte Proliferation and Formation of Duct-Like Structure", Hepatoloty, 26(6): 1444-1457, 1997.
Cakir-Kiefer et al. "Kinetic Competence of the cADP-Ribose-CD38 Complex as an Intermediate in the CD38/NAD+ Glycohydrolase-Catalysed Reactions: Implication for CD38 Signalling", Biochemical Journal, 358: 399-406, 2001.
Caliaro et al. "Response of Four Human Ovarian Carcinoma Cell Lines to Al-Trans Retinoic Acid: Relationship With Induction of Differentiation and Retinoic Acid Receptor Expression", International Journal of Cancer, 56: 743-748, Mar. 1, 1994.
Casal et al. "In Utero Transplantation of Fetal Liver Cells in the Mucopolysaccharidosis Type VII Mouse Results in Low-Level Chimerism, But Overexpression of Beta-Glucuronidase Can Delay Onset of Clinical Signs", Blood, 97(6): 1625-1634, 2001.
Cepko "Overview of the Retrovirus Transduction System", Short Protocols in Molecular Biology, Unit 9.10-9.14: 9-41-9-57, 1984.
Charrier et al. "Normal Human Bone Marrow CD34+CD133+ Cells Contain Primitive Cells Able to Produce Different Categories of Colony-Forming Unit Megacaryocytes In Vitro", Experimental Hematology, 30: 1051-1060, 2002.
ChemMasters "Duraguard 100", Safety Data Sheet, p. 1-4, 1999.
Chen et al. "Fibroblast Growth Factor (FGF) Signaling Through PI 3-Kinase and Akt/PKB Is Required for Embryoid Body Differentiation", Oncogene, 19: 3750-3756, 2000. p. 3752-3755.
Chen et al. "Therapeutic Benefit of Intravenous Administration of Bone Marrow Stromal Cells After Cerebral Ischemia in Rats", Stroke, 32(4): 1005-1011, 2001.
Chisi et al. "Inhibitory Action of the Peptide AcSDKP on the Proliferative State of Hematopoietic Stem Cells in the Presence of Captopril But Not Lisinopril", Stem Cells, 15(6): 455-460, 1997.
Chowdhury et al. "Long-Term Improvement of Hypercholesterolemia After Ex Vivo Gene Therapy in LDLR-Deficient Rabbits", Science, 254: 1802-1805, 1991.
Cicuttini et al. "Support of Human Cord Blood Progenitor Cells on Human Stromal Cell Lines Transformed by SV40 Large T Antigen Under the Influence of an Inducible (Metallothionein) Promoter", Blood, 80(1): 102-112, 1992.
Cole et al. "The EBV-Hybridoma Technique and Its Application to Human Lung Cancer", Monoclonal Antibodies and Cancer Therapy, p. 77-96, 1985.
Collins et al. "Stirred Culture of Peripheral and Cord Blood Hematopoietice Cells Offers Advantages over Traditional Static Systems for Clinically Relevant Applications", Biotechnology and Bioengineering, 59(5): 534-543, 1998.
Colter et al. "CD34+ Progenitor Cell Selection: Clinical Transplantation, Tumor Cell Purging, Gene Therapy, Ex Vivo Expansion, and Cord Blood Processing", Journal of Hematology,5: 179-184, 1996.
Côtó et al. "Response to Histone Deacetylase Inhibition of Novel PML/RARα Mutants Detected in Retinoic Acid-Resistant APL Cells", Blood, 100(7): 2586-2596, 2002.
Coutinho et al. "Effects of Recombinant Human Granulocyte Colony-Stimulating Factor (CSF), Human Granulocyte Macrophage-CSF, and Gibbon Interleukin-3 on Hematopoiesis in Human Long-Term Bone Marrow Culture", Blood, 75(11): 2118-2129, 1990.
Cristiano et al. "Hepatic Gene Therapy: Adenovirus Enhancement of Receptor-Mediated Gene Delivery and Expression in Primary Hepatocytes", Proc. Natl. Mad. Sci. USA, 90: 2122-2126, 1993.
Curiel et al. "Adenovirus Enhancement of Transferrin-Polylysine-Mediated Gene Delivery", Proc. Natl. Acad. Sci. USA, 88: 8850-8854, 1991.
Czaudema, et al., "Functional studies of the PI(3)-kinase signalling pathway employing synthetic and expressed siRNA.", Nuc. Acid Res., 31(2):670-682 (2003).
Dabeva et al. "Transcription Factor and Liver-Specific mRNA Expression in Facultative Epithelial Progenitor Cells of Liver and Pancreas", American Journal of Pathology, 147: 1633-1648, 1995. Abstract.
Dahl et al. "Tranformation of Hematopoietic Cells by the Ski Oncoprotein Involves Repression of Retinoic Acid Receptor Signaling", Proc. Natl. Acad. Sci. USA, 95(19): 11187-11192, 1998.

Dai et al. "Gene Therapy Via Primary Myoblasts: Long-Term Expression of Factor IX Protein Following Transplantation In Vivo", Proc. Natl. Acad. Sci. USA, 89: 10892-10895, 1992.

Dalyot et al. "Adult and Neonatal Patterns of Human Globin Gene Expression Are Recapitulated in Liquid Cultures", Experimental Hematology, 20: 1141-1145, 1992.

Danos et al. "Safe and Efficient Generation of Recombinant Retroviruses With Amphotropic and Ecotropic Host Ranges", Proc. Natl. Acad. Sci. USA, 85: 6460-6464, 1988.

Datta et al. "Ionizing Radiation Activates Transcription of the EGR1 Gene Via CArG Elements", Proc. Natl. Acad. Sci. USA, 89: 10149-10153, 1992.

De Bruyn et al. "Comparison of the Coexpressioin of CD33 and HLA-DR Antigens on CD34+ Purified Cells From Human Cord Blood and Bone Narrow", Stem Cells, 13: 281-288, 1995.

De Luca et al. "Retinoic Acid Is a Potent Regulator of Growth Plate Chondrogenesis", Endocrinology, 141(1): 346-353, 2000. Abstract.

De Wynter et al. "CD34+AC133+ Cells Isolated From Cord Blood Are Highly Enriched in Long-Term Culture-Initiating Cells, NOD/SCID-Repopulating Cells and Dendritic Cell Progenitors", Stem Cells, 16: 387-396, 1998.

Defacque et al. "Expression of Retinoid X Receptor Alpha Is Increased Upon Monocytic Cell Differentiation", Biochemical and Biophysical Research Communications, 220: 315-322, 1996.

Dexter et al. "Conditions Controlling the Proliferation of Haemopoietic Stem Cells In Vitro", Journal of Cell Physiology, 91: 335-344, 1976.

Dosil et al., "Mitogenic signalling and substrate specificity of the Flk2/Flt3 receptor tyrosine kinase in fibrobiasis and interleukin 3-dependent hematopoietic cells", *Mo. Cell Biol.*, 13(10):6572-6585 (1993). Abstract.

Douer et al. "All-trans-retinoic Acid Effects the Growth, Differentiation and Apoptosis of Normal Human Myeloid Progenitors Derived from Purified CD34+ Bone Marrow Cells", Leukemia, 14(5): 874-881, 2000.

Drayson et al. "Cell Proliferation and CD11b Expression are Controlled Independently During HL60 Cell Differentiation Initiated by 1,25α-Dihydroxyvitamin D3 or All-trans-Retinoic Acid", Exp. Cell Res., 266(1): 126-134, 2001. Abstract.

Dubois et al. "Treatment of Wilson's Disease With Triethylene Tetramine Hydrochloride (Trientine)", Journal of Pediatric Gastroenterology and Nutrition, 10(1): 77-81, 1990. Abstract.

Duncan et al. "Repair of Myelin Disease: Strategies and Progress in Animal Models", Molecular Medicine Today, 3(12): 554-561, 1997. Abstract.

Ebner et al. "Distinct Roles for PI3K in Proliferation and Survival of Oligodendrocyte Progenitor Cells", Journal of Neuroscience Research, 62: 336-345, 2000. p. 338-344.

Eglitis et al. "Gene Expression in Mice After High Efficiency Retroviral-Mediated Gene Transfer", Science, 230: 1395-1398, 1985.

Ehring et al. "Expansion of HPCs From Cord Blood in a Novel 3D Matrix", Cytotherapy, 5(6): 490-499, 2003.

Eipers et al. "Retroviral-Mediated Gene Transfer in Human Bone Marrow Cells Grown in Cortinuous Perfusion Culture Vessels", Blood, 86(10): 3754-3762, 1995.

Englisch et al. "Chemically Modified Oligonucleotides as Probes and Inhibitors", Angewandte Chemie (International Edition in English), 30(6): 613-629, 1991.

Fasouliotis et al. "Human Umbilical Cord Blood Banking and Transplantation: A State of the Art", European Journal of Obstetrics & Gynecology and Reproductive Biology, 90(1): 13-25, 2000.

Feldman "Israeli Start-Up Gamida-Cell to Receive Prize", GLOBES—Online, 2004.

Ferbeyre "PML A Target of Translocations in APL Is A Regulator of Cellular Senescence", Leukemia, 16: 1918-1926, 2002. Abstract.

Ferrero et al. "The Metamorphosis of A Molecule: From Soluble Enzyme to the Leukocyte Receptor CD38", Journal of Leukocyte Biology; 65(2): 151-161, 1999.

Ferry et al. "Retroviral-Mediated Gene Transfer Into Hepatocytes In Vivo", Proc. Natl. Acad. Sci. USA, 88: 8377-8381, 1991.

Fibach et al. "Growth of Human Normal Erythroid Progenitors in Liquid Culture: A Comparison With Colony Growth in Semisolid Culture", International Journal of Cell Cloning, 9: 57-64, 1991.

Fibach et al. "Normal Differentiation of Myeloid Leukemic Cells Induced by a Protein Differentiation Inducing Protein", Nature New Biology, 237(78): 276-278, 1972.

Fibach et al. "Proliferation and Maturation of Human Erythroid Progenitors in Liquid Culture", Blood, 73(1): 100-103, 1989. Abstract.

Fibach et al. "Retinoic Acid Antagonist Inhibits CD38 Antigen Expression on Human Hematopoietic Cells", Blood, 100(11): 172A & 44th Annual Meeting of the American Society of Hematology, 2002. Abstract.

Fibach et al. "The Two-Step Liquid Culture: A Novel Procedure for Studying Maturation of Human Normal and Pathological Erythroid Precursors", Stem Cells, 11(Suppl.1): 36-41, 1993. Abstract.

Fietz et al. "Culturing Human Umbilical Cord Blood: A Comparison of Mononuclear Vs CD34+ Selected Cells", Bone Marrow Transplantation, 23: 1109-1115, 1999.

Filvaroff et al. "Functional Evidence for an Extracellular Calcium Receptor Mechanism Triggering Tyrosine Kinase Activation Associated With Mouse Keratinocyte Differentiation", The Journal of Biological Chemistry, 269(34): 21735-21740, 1994.

Fishwild et al. "High-Avidity Human IgG? Monoclonal Antibodies From a Novel Strain of Minilocus Transgenic Mice", Nature Biotechnology, 14: 845-851, 1996.

Flores et al. "Akt-Mediated Survival of Oligodendrocytes Induced by Neuregulins", The Journal of Neuroscience, 20(20): 7622-7630, 2000. p. 7624-7629.

Flotte et al. "Expression of the Cystic Fibrosis Transmemebrane Conductance Regulators From a Novel Adeno-Associated Virus Promoter", The Journal of Biological Chemistry, 268(5): 3781-3790, 1993.

Flotte et al. "Gene Expression From Adeno-Associated Virus Vectors in Airways Epithelial Cells", American Journal of Respiratory Cell and Molecular Biology, 7: 349-356, 1992.

Forraz, et al., "AC133+ umbilical cord blood progenitors demonstrate rapid self-renewal and low apoptosis.", *Br. J. Haematol.*, 119(2):516-524 (2002).

Fosmire "Zinc Toxicity", American Journal of Clinical Nutrition, 51(2): 225-227, 1990. Abstract.

Freshney "Culture of Animal Cells, A Manual of Basic Technique", John Wiley & Sons, 3rd Ed., Chap.20: 309-311, 327-328, 1994.

Fry, M. J., "Phosphoinositide 3-kinase signalling in breast cancer: how big a role might it play?", *Breast Cancer Res.*, 3(5):304-312 (2001).

Gagnon et al. "Activation of Protein Kinase B and Induction of Adipogenesis by Insulin in 3T3-L1 Preadipocytes", Diabetes, 48: 691-698, 1999. p. 693-697.

Gallacher et al. "Isolation and Characterization of Human CD34-Lin- and CD34+Lin-Hematopoietic Stem Cells Using Cell Surface Markers AC133 and CD7", Blood, 95(9): 2813-2820, 2000.

Gloeckner et al. "New Miniaturized Hollow-Fiber Bioreactor for In Vivo Like Cell Culture, Cell Expansion, and Production of Cell-Derived Products", Biotechnology Progresses, 17: 828-831, 2001.

Gossler et al. "Transgenesis by Means of Blasocyst-Derived Embryonic Stem Cell Lines", Proc. Natl. Acad. Sci. USA, 83: 9065-9069, 1986.

Gould-Fogerite et al. "Chimerasome-Mediated Gene Transfer In Vitro and In Vivo", Gene, 84: 429-438, 1989.

Grande et al. "Physiological Levels of 1Alpha, 25 Dihydroxyvitamin D3 Induce the Monocytic Commitment of CD34+ Hematopoietic Progenitors", J. Leukoc. Biol., 71(4): 641-651, 2002.

Grenda et al. "Mice Expressing A Neutrophil Elastase Mutation Derived From Patients With Severe Congenital Neutropenia Have Normal Granulopoiesis", Blood, 100(9): 3221-3228, 2002.

Gur et al. "Toelrance Induction by Megadose Hematopoietic Progenitor Cells: Expansion of Veto Cells by Short-Term Culture of Purified Human CD34+ Cells", Blood, 99: 4174-4181, 2002.

Haj-Ahmad et al. "Development of a Helper-Independent Human Adenovirus Vector and Its Use in the Transfer of the Herpes Simplex Virus Thymidine Kinase Gene", Journal of Virology, 57(1): 267-274, 1986.

Hamilton "Stem Cell Technology to Treat Leukemia Patients Show Promise", The Wall Street Journal, Online, 2003.

Hammond et al. "Suppression of In Vitro Granulocytopoiesis by Captopril and Penicillamine", Experimental Hematology, 16(8): 674-680, 1988.

Hatayama et al. "Regulation of HSP70 Synthesis Induced by Cupric Sulfate and Zinc Sulfate in Thermotolerant HeLa Cells", Journal of Biochemistry, Tokyo, 114(4): 592-597, 1993. Abstract.

Haviernik et al., "Tissue inhibitor of matrix metalloproteinase-1 overexpression in M1 myeloblasts impairs IL-6-induced differentiation", Oncogene, 23(57):9212-9219 (2004). Abstract.

Hayashi et al. "Changes in the Balance of Phosphoinositide 3-Kinase/Protein Kinase B (AKt) and the Mitogen-activated Protein Kinases (ERK/p38MAPK) Determine a Phenotype of Visceral and Vascular Smooth Muscle Cells", J. Cell Biol., 145(4): 727-740, 1999.

Haylock et al. "Ex-Vivo Expansion and Maturation of Peripheral Blood CD34+ Cells Into the Myeloid Lineage", Blood, 80(5): 1405-1412, 1992.

Hermonat et al. "Use of Adeno-Associated Virus as A Mammalian DNA Cloning Vector: Transduction of Neomycin Resistance Into Mammalian Tissue Culture Cells", Proc. Natl. Acad. Sci. USA, 81: 6466-6470, 1984.

Herz et al. "Adenovirus-Mediated Transfer of Low Density Lipoprotein Receptor Gene Acutely Accelerates Cholesterol Clearence in Normal Mice", Proc. Natl. Acad. Sci. USA, 90: 2812-2816, 1993.

Heuchel et al. "The Transcription Factor MTF-1 Is Essential for Basal and Heavy Metal-Induced Metallothionein Gene Expression", The EMBO Journal, 13(12): 2870-2875, 1994.

Hida et al. "Existence of Retinoic Acid-Receptor-Independent Retinoid X-Receptor-Dependent Pathway in Myeloid Cell Function", Japanese Journal of Pharmacology, 85(1): 60-69, 2001.

Higashi et al., "Autologous Bone-Marrow Mononuclear Cell Implantation Improves Endothelium-Dependent Vasodilation in Patients With Limb Ischemia", Circulation, 109:1215-1218 (2004).

Hino et al. "A Long-Term Culture of Human Hepatocytes Which Show a High Growth Potential and Express Their Differentiated Phenotypes*[1]", Biochemical and Biophysical Research Communications, 256(1): 184-191, 1999, Abstract.

Hirase et al. "Anemia and Neutropenia in a Case of Copper Deficiency: Role of Copper in Normal in Hematopiesis", Acta Haematology, 87(4): 195-197, 1992.

Hirose et al. "Identification of a Transposon-Related RNA Down-Regulated by Retinoic Acid in Embryonal Carcinoma and Embryonic Stem Cells", Experimental Cell Research, 221(2): 294-300, 1995. Abstract.

Hmama et al. "1-Alpha, 25-Dihydroxyvitamin D3-Induced Myeloid Cell Differentiation Is Regulated by A Vitamin D Receptor-Phosphatidylinositol 3-Kinase Signaling Complex", Journal of Experimental Medicine, 190(11): 1583-1594, 1999.

Hoffman et al. "Zinc-Induced Copper Deficiency", Gastroenterology, 94(2): 508-512, Feb. 1988. Abstract.

Hofmeister et al. "Ex Vivo Expansion of Umbilical Cord Blood Stem Cells for Transplantation: Growing Knowledge From the Hematopoietic Niche", Bone Marrow Transplantation, 39: 11-23, 2007.

Holleman "Triethylene Tetramine, CAS No. 112-24-3", Chemical Hazard Information Profile Draft Report, 1982. Abstract.

Hoogenboom et al. "By-Passing Immunisation. Human Antibodies From Synthetic Repertoires of Germline VH Gene Segments Rearranged In Vitro", Journal of Molecular Biology, 227: 381-388, 1992.

Hori et al. "Growth Inhibitors Promote Differentiation of Insulin-Producing Tissue From Embryonic Stem Cells", Proc. Natl. Acad. Sci. USA, 99(25): 16105-16110, 2002.

Hottinger et al. "The Copper Chelator D-Penicillamine Delays Onset of Disease a Extends Survival in a Transgenic Mouse Model of Familial Amyotrophic Lateral Sclerosis", European Journal of Neuroscience, 9(7): 1548-51, 1997. Abstract.

Howard et al. "Formation and Hydrolysis of Cyclic ADP-Ribose Catalyzed by Lymphocyte Antigen CD38", Science, 262(5136): 1056-1059, 1993, Abstract.

Huang et al. "Differentiation of Human U937 Promonocytic Cells Is Impaired by Moderate Copper Deficiency", Experimental Biology and Medicine, 226(3): 222-228, 2001.

Huber et al. "Retroviral-Mediated Gene Therapy for the Treatment of Hepatocellular Carcinoma: An Innovative Approach for Cancer Therapy", Proc. Natl. Acad. Sci. USA, 88: 8039-8043, 1991.

Hutvágner et al. "RNAi: Nature Abhors a Double-Strand", Current Opinion in Genetics & Development, 12: 225-232, 2002.

Hwu et al. "Functional and Molecular Characterization of Tumor-Infiltrating Lymphocytes Transduced With Tumor Necrosis Factor-? cDNA for the Gene Therapy of Cancer in Humans", The Journal of Immunology, 150(9): 4104-4115, 1993.

Inbar et al. "Localization of Antibody-Combining Sites Within the Variable Portions of Heavy and Light Chains", Proc. Natl. Acad. Sci. USA, 69(9): 2659-2662, 1972.

Itoh et al. "Inhibition of Urokinase Receptor (uPAR) Expression by RNA-Cleaving Catalytic DNA (DNAzyme) Containing Antisense uPAR", Molecular Therapy, 5(5/Part2): S134, 2002.

Jelinek et al. "Novel Bioreactors for the Ex Vivo Cultivation of Hematopoietic Cells", English Life Science, 2(1): 15-18, 2002.

Jiang et al. "Phosphatidylinositol 3-Kinase Signaling Mediates Angiogenesis and Expression of Vascular Endothelia Growth Factor in Endothelial Cells", PNAS, 97(4): 1749-1753, 2000.

Johnson et al. "Synthesis and Biological Activity of High-Affinity Retinoic Acid Receptor Antagonists", Bioorganic & Medicinal Chemistry, 7(7): 1321-1338, 1999.

Johnson et al. "The Cytokines IL-3 and GM-CSF Regulate the Transcriptional Activity of Retinoic Acid Receptors in Different In Vitro Models of Myeloid Differentiation", Blood, 99(3): 746-753, 2002.

Jones et al. "Replacing the Complementarity-Determining Regions in a Human Antibody With Those From a Mouse", Nature, 321: 522-525, 1986.

Kähne et al. "Dipeptidyl Peptidase IV: A Cell Surface Peptidase Involved in Regulating T Cell Growth (Review)", International Journal of Molecular Medicine, 4: 3-15, 1999.

Kang et al. "Retinoic Acid and Its Receptors Repress the Expression and Transactivation Functions of Nur77: A Possible Mechanism for the Inhibition of Apoptosis by Retinoic Acid", Experimental Cell Research, 256: 545-554, 2000.

Kastner et al. "Positive and Negative Regulation of Granulopoiesis by Endogenous RARalpha", Blood, 97(5): 1314-1320, 2001. Abstract.

Kaufman et al. "Translational Efficency of Polycistronic mRNAs and Their Utilization to Express Heterologous Genes in Mammalian Cells", The EMBO Journal, 6(1): 187-193, 1987.

Kawa et al. "Stem Cell Factor and/or Endothelin-3 Dependent Immortal Melanoblast and Melanocyte Populations Derived From Mouse Neural Crest Cells", Pigment Cell Research, 13(Suppl.8): 73-80, 2000.

Kay et al. "Hepatic Gene Therapy: Persistent Expression of Human ?1-Antitrypsin in Mice After Direct Gene Delivery In Vivo", Human Gene Therapy, 3: 641-647, 1992.

Keith et al. "Multicomponent Therapeutics for Networked Systems", Nature Reviews: Drug Discovery, 4: 1-8, 2005.

Khachigian "DNAzymes: Cutting a Path to a New Class of Therapeutics", Current Opinion in Molecular Therapeutics, 4(2): 119-121, 2002.

Kim "Differentiation and Identification of the Two Catalytic Metal Binding Sites in Bovine Lens Leucine Aminopeptidase by X-Ray Crystallography", Proc. Natl. Acad. Sci. USA, 90(11): 5006-5010, 1993.

Kishimoto et al. "Molecular Mechanism of Human CD38 Gene Expression by Retinoic Acid. Identification of Retinoic Acid Response Elemen in the First Intron", Journal ofBiological Chemistry, 273(25): 15429-15434, 1998.

Kitanaka, et al., "CD38 ligation in human B cell progenitors triggers tyrosine phosphorylation of CD19 and association of CD19 with lyn and phosphatidylinositol 3-kinase.", J. Immunol., 159(1):184-192 (1997).

Kizaki et al. Regulation of Manganese Superoxide Dismutase and Other Antioxidant Genes in Normal and Leukemic Hematopoietic Cells and Their Relationship to Cytotoxicity by Tumor Necrosis Factor, Blood, 82(4): 1142-1150, 1993.

Kobari et al. "CD133+ cell selection is an alternative to CD34+ cell selection for ex vivo expansion of hematopoietic stem cells.", *J. Hematother Stem Cell Res*. 2001; 10(2):273-81.

Kocher et al. "Neovascularization of Ischemic Myocardium by Human BoneMarrow-Derived Angioblasts Prevents Cardiomyocyte Apoptosis, Reduces Remodeling and Improves Cardiac Function", Nature Medicine, 7(4): 430-436, 2001.

Köhler et al. "Defining Optimum Conditions for the Ex Vivo Expansion of Human Umbilical Cord Blood Cells. Influences of Progenitor Enrichment, Interference With Feeder Layers, Early-Acting Cytokines and Agitation of Culture Vessels", Stem Cells, 17(1)19-24, 1999.

Kohroki et al. "Induction of Differentiation and Apoptosis by Dithizone in Human Myeloid Leukemia Cell Lines", Leukemia Research, 22(5): 405-412, 1998.

Koizumi et al. "Large Scale. Purification of Human Blood CD34+ Cells From Cryopreserved Peripheral Blood Stem Cells, Using a Nylon-Fiber Syringe System and Immunomagnetic Microspheres", Bone Marrow Transplantation, 26: 787-793, 2000.

Krause et al. "Multi-Organ, Multi-Lineage Engraftment by a Single Bone Marrow-Derived Stem Cell", Cell, 105(3): 369-377, 2001. Abstract.

Kronenwett et al. "Oligodeoxyribonucleotide Uptake in Primary Human Hematopoietic Cells Is Enhanced by Cationic Lipids and Depends on the Hematopoietic Cell Subset", Blood, 91(3): 852-862, 1998.

Kumagai et al. "Ligation of CD38 Suppresses Human B Lymphopoiesis", Journal of Experimental Medicine, 181(3): 1101-1110, 1995.

Labrecque et al. "Impaired Granulocytic Differentiation in Vitro in Hematopoietic Cells Lacking Retinoic Acid Receptors αl and γ", Blood, 92(2): 607-615, 1998.

Lagasse et al. "Purified Hematopoietic Stem Cells Can Differentiate Into Hepatocytes In Vivo", Nature Medicine, 6(11): 1229-1234, 2000. Abstract.

Lam et al. "Preclinical Ex Vivo Expansion of Cord Blood Hematopoietic Stem and Progenitor Cells: Duration of Culture; the Media, Serum Supplements, and Growth Factors Used; and Engraftment in NOD/SCID Mice", Transfusion, 41(12): 1567-1576, 2001. Abstract.

Lange et al. "Biological and Clinical Advances in Stem Cell Expansion", Leukemia, 10: 943-945, 1996.

Lapidot et al. "Cytokine Stimulation of Multilineage Hematopoiesis From Immature Human Cells Engrafted in SCID Mice", Science, 255: 1137-1141, 1992. Abstract.

Larrick et al. "PCR Amplification of Antibody Gehes", Methods: A Companion to Methods in Enzymology, 2(2): 106-110, 1991.

Lassila et al. "Role for Lys-His-Gly-NH2 in Avian and Murine B Cell Development", Cellular Immunology, 122(2): 319-328, 1989.

Lau et al. "A Peptide Molecule Mimicking the Copper (Ii) Transport Site of Human Serum Albumin", Journal of Biological Chemistry, 249(18): 5878-5884, 1974.

Lavigne et al. "Enhanced Antisense Inhibition of Human Immunodeficiency Virus Type 1 in Cell Cultures by DLS Delivery System", Biochemical and Biophysical Research Communications, 237: 566 571, 1997.

Lawlor et al. "Coordinate Control of Muscle Cell Survival by Distinct Insulin-Like Growth Factor Activated Signaling Pathways", The Journal of Cell Biology, 151(6): 1131-1140, 2000. p. 1133-1139.

Lee et al. "Effect of Vitamin D3 Analog, EB1089, on Hematopoietic Stem Cells From Normal and Myeloid Leukemic Blasts", Leukemia, 10: 1751-1757, 1996.

Lemarchand et al. "Adennvirus-Mediated Transfer of A Recombinant Human α1-Antitrypsin cDNA to Human Endothelial Cells", Proc. Natl. Acad. Sci. USA, 89: 6482-6486, 1992.

Leslie et al. "An Activating Mutation in the Kit Receptor Abolishes the Stroma Requirement for Growth of ELM Erythroleukemia Cells, But Does Not Prevent Their Differentiation in Response to Erythropoietin", Blood, 92(12): 4798-4807, 1998.

Lewandowski et al. "Phosphatidylinositol 3-Kinases Are Involved in the All-Trans Retinoic Acid-Induced Upregulation of CD38 Antigen on Human Haematopoietic Cells", British Journal of Hematology, 118(2): 535-544, 2002. Fig.8.

Li et al. "Activation of Phosphatidylinositol-3 Kinase (PI-3K) and Extracellular Regulated Kinases (Erk½) Is Involved in Muscarinic Receptor-Mediated DNA Synthesis in Neural Progenitor Cells", The Journal of Neuroscience, 21(5): 1569-1579, 2001. p. 1572-1578.

Lianguzova et al. "PI3-Kinase Inhibitors LY294002 and Wortmannin Have Different Effects on Proliferation of Murine Embryonic Stem Cells", Tsitologiia, 48(7): 560-568, 2006. Abstract.

Lonberg et al. "Antigen-Specific Human Antibodies From Mice Comprising Four Distinct Genetic Modifications", Nature, 368: 856-859, 1994.

Lonberg et al. "Human Antibodies From Transgenic Mice", International Review in Immunology, 13: 65-93, 1995.

Lovejoy et al. "Novel 'Hybrid' Iron Chelators Derived From Aroylhydrazones and Thiosemicarbazones Demonstrate Delective Antiproliferative Activity Against Tumor Cells", Blood, 100(2): 666-676, 2002.

Lu et al. "Intravenous Administration of Human Umbilical Cord Blood Reduces Neurological Deficit in the Rat After Traumatic Brain Injury", Cell Transplant., 11(3): 275-281, 2002. Abstract.

Luft "Making Sense Out of Antisense Oligodeoxynucleotide Delivery: Getting There Is Half the Fun". J. Mol. Med, p. 75-76. 1998.

Lutton et al. "Zinc Porphyrins: Potent Inhibitors of Hematopoieses in Animal and Human Bone Marrow", Proc. Natl. Acad. Sci. USA, 94: 1432-1436, 1997.

Ma, et al., "Inhibition of phosphatidylinositol 3-kinase causes apoptosis in retinoic acid differentiated hl-60 leukemia cells.", *Cell Cycle*, 3(1):67-70 (2004).

Mader et al. "A Steroid-Inducible Promoter for the Controlled Overexpression of Cloned Genes in Eukaryotic Cells", Proc. Natl. Acad. Sci. USA, 90: 5603-5607, 1993.

Madlambayan et al. "Controlling Culture Dynamics for the Expansion of Hematopoietic Stem Cells", Journal of Hematotherapy and Stem Cell Research, 10(4): 481-492, 2001. Abstract.

Manome et al. "Coinduction of C-Jun Gene Expression and Intemucleosomal DNA Fragmentation by Ionizing Radiation", Biochemistry, 32: 10607-10613, 1993.

Mar et al. "A Conserved CATTCT Motif Is Required for Skeletal Muscle-Specific Activity of the Cardiac Troponin T Gene Promoter", Proc. Natl. Acad. Sci. USA, 85: 6404-6408, 1988.

Marcinkowska "Does the Universal 'Signal Transduction Pathway of Differentiation' Exist? Comparison of Different Cell Differentiation Experimental Models With Differentiation of HL-60 Cells in Response to 1,25-Dihydroxyvitamin D3", Postepy Higieny i Medycyny Doświadczalnej, 53(2): 305-313, 1999. Abstract.

Marks et al. "By-Passing Immunization. Human Antibodies From V-Gene Libraries Displayed on Phage", Journal of Molecular Biology, 222: 581-597, 1991.

Marks et al. "By-Passing Immunization: Building High Affinity Human Antibodies by Chain Shuffling", Bio/Technology, 10: 779-783, 1992.

Martelli et al. "Transplants Across Human Leukocyte Antigen Barriers", Seminars in Hematology, 39(1): 48-56, 2002.

Matuoka et al. "A Positive Role of Phosphatidylinositol 3-Kinase in Aging Phenotype Expression in Cultured Human Diploid Fibroblasts", Arch. Gerontal. Geriatry, 36:203-219, 2003.

Matzner et al. "Bone Marrow Stem Cell Gene Therapy of Arylsulfatase A-Deficient Mice, Using an Arylsulfatase A Mutant That Is Hypersecreted From Retrovirally Transduced Donor-Type Cells", Human Gene Therapy, 12: 1021-1033, 2001.

McNiece et al. "Action of Interleukin-3, G-CSF on Highly Enriched Human Hematopoietic Preogenitor Cells: Synergistic Interaction of GM-CSF Plus G-CSF", Blood, 74: 110-114, 1989.

McNiece et al. "CD34+ Cell Selection From Frozen Cord Blood Products Using the Isolex 300i and CliniMACS CD34 Selection Devices", Journal of Hematotherapy, 7: 457-461, 1998.

McNiece et al., "Ex vivo Expansion of Cord Blood Mononuclear Cells on Mesenchymal Stem Cells", *Cytotherapy*, 6(4):311-317 (2004).

Mehta et al. "Human CD38, A Cell-Surface Protein With Multiple Functions", The FASEB Journal, 10(12): 1408-1417, 1996.

Mehta et al. "Involvement of Retinoic Acid Receptor-α-Mediated Signaling Pathway in Induction of CD38 Cell-Surface Antigen", Blood, 89(10): 3607-3614, 1997.

Mehta et al. "Retinoid-Mediated Signaling Pathways in CD38 Antigen Expression in Myeloid Leukema Cells", Leukemia and Lymphoma, 32(5/6): 441-449, 1999.

Meissner et al. "Development of a Fixed Bed Bioreactor for the Expansion of Human Hematopoietic Progenitor Cells", Cytotechnology, 30: 227-234, 1999.

Merck & Co. "The Merck Index, An Encyclopedia of Chemicals, Drugs and Biologicals", 10th Ed.(3742): 549, 1983.

Mezey et al. "Turning Blood Into Brain: Cells Bearing Neuronal Antigens Generated In Vivo From Bone Marrow", Science, 290(5497): 1779-1782, 2000.

Migliaccio et al. "Long-Term Generation of Colony-Forming Cells in Liquid Culture of CD34+ Cord Blood Cells in the Presence of Recombinant Human Stem Cell Factor", Blood, 79: 2620-2627, 1992.

Miller "Progress Toward Human Gene Therapy", Blood, The Journal of the American Society of Hematology, 76(2): 271-278, 1990.

Miller et al. "Expansion In Vitro of Adult Murine Hematopoietic Stem Cells With Transplantable Lympho-Myeloid Reconstituting Ability", Proc. Natl. Acad. Sci. USA, 94: 13648-13653, 1997.

Mills et al. "Regulation of Retinoid-Induced Differentiation in Embryonal Carcinoma PCC4.Aza 1 R Cells: Effects of Retinoid-Receptor Selective Ligands", Cell Growth Differ., 7(3): 327-337, 1996. Abstract.

Mood, et al., "Contribution of JNK, Mek, Mos and PI-3K signaling to GVBD in Xenopus oocytes.", *Cell. Signalling*, 16:631-642 (2004).

Moore et al. "Ex Vivo Expansion of Cord Blood-Devined Stem Cells and Progenitons", Blood Cells, 20: 468-481, 1994.

Morier-Teissier et al. "Synthesis and Antitumor Properties of an Anthraquinone Bisubstituted by the Copper Chelating Peptide Gly-Gly-L-His", Journal of Medical Chemistry, 36: 2084-2090, 1993. Abstract.

Morimoto et al. "EDTA Induces Differentiation and Suppresses Proliferation of Promyelotic Leukemia Cell Line HL-60—Possible Participation of Zinc-", Biochemistry International, 28(2): 313-321, 1992.

Morosetti et al. "Infrequent Alterations of the RARα Gene in Acute Myelogenous Leukemias, Retinoic Acid-Resistant Acute Promyelocytic Leukemias, Myelodysplastic Syndromes, and Cell Lines", Blood, 87(10): 4399-4403, May 15, 1996.

Morrison "Success in Specification", Nature, 368(6474): 812-813, 1994.

Morrison et al. "Identification of a Lineage of Multipotent Hematopoietic Progenitors", Development, 124: 1929-1939, 1997.

Morrison et al. "The Long-Term Repopulating Subset of Hematopoietic Stem Cell Is Deterministic and Isolatable by Phenotype", Immunity, 1: 661-673, 1994. Abstract.

Mueller et al. "Heterozygous PU.1 Mutations Are Associated With Acute Myeloid Leukemia", Blood, 100(3): 998-1007, 2002.

Muench et al. "Interactions Among Colony-Stimulating Factors, IL-1β, IL-6, and Kit-Ligand in the Regulation of Primitive Murine Hematopoietic Cells", Experimental Hematoloiy, 20: 339-349, 1992.

Mulloy et al. "Maintaining the self-renewal and differentiation potential of human CD34+ hematopoietc cells using a single genetic element," Blood, 102(13):4369-76, 2003.

Munshi et al. "Evidence for a Causal Role of CD38 Expression in Granulocytic Differentiation of Human HL-60 Cells", The Journal of Biological Chemistry, 277(51): 49453-49458, 2002.

Muramatsu et al. "Reversible Integration of the Dominant Negative Retinoid Receptor Gene for Ex Vivo Expansion of Hematopoietic Stem/Progenitor Cells", Biochemical & Biophysical Research Communications, 285(4): 891-896, 2001. Abstract.

Murray et al. "Modulation of Murine Lymphocyte and Macrophage Proliferation by Parenteral Zinc", Clinical and Experimental Immunology, 53(3): 744-749, 1983.

Murray et al. "Thrombopoietin, Flt3, and Kit Ligands Together Suppress Apoptosis of Human Mobilized CD34+ Cells and Recruit Primitive CD34+Thy-1+ Cells Into Rapid Division", Experimental Hematology, 27: 1019-1028, 1999.

Murry et al., "Haematopoietic Stem Cells Do Not Transdifferentiate Into Cardiac Myocytes in Myocardial Infarcts", *Nature*, 428:664-668 (2004).

Muzyczka "Use of Adeno-Associated Virus as a General Transduction Vector for Mammalian Cells", Current Topics in Microbiology and Immunology, 158: 97-129, 1992.

Narita et al. "Cardiomycyte Differentiation by GATA-4-Deficient Embryonic Stem Cells", Development, 122(19): 3755-3764, 1996.

Neuberger "Generating High-Avidity Human Mabs in Mice", Nature Biotechnology, 14: 826, 1996.

Nicolau et al. "Liposomes as Carriers for In Vivo Gene Transfer and Expression", Methods in Enzymology, 149(Chap.16): 157-176, 1987.

Ohishi et al. "Delta-1 Enhances Marrow and Thymus Repopulating Ability of Human CD34+CD38 Cord Blood Cells", The Journal of Clinical Investigation, 110(8): 1165-1174, 2002.

Okazaki et al. "Characteristics and Partial Purification of a Novel Cytosolic, Magnesium-Independent, Neutral Sphingomyelinase Activated in the Early Signal Transduction of 1?,25-Dihydroxyvitamin D3-Induced HL-60 Cell Differentiation", The Journal of Biological Chemistry, 269(6): 4070-4077, 1994.

Okuno et al. "Differential regulation of the human and murine CD34 genes in hematopoietic stem cells." Proc Natl Acad Sci U S A., 99(9):6246-51, 2002.

Olivares et al. "Copper As An Essential Nutrient", The American Journal of Clinical Nutrition, 63: 791S-796S, 1996. Abstract.

Orlic et al. "Exogenous Hematopoietic Stem Cells Can Regenerate Infarcted Myocardium", Circulation, 102: 2672, 2000.

Orlic et al. "Mobilized Bone Marrow Cells Repair the Infarcted Heart, Improving Function and Survival", Proc. Natl. Acad. Sci. USA, 98(18): 10344-10349, 2001.

Orlic et al. "Transplanted Adult Bone Marrow Cells Repair Myocardial Infarcts in Mice", Annals of the New York Academy of Sciences, 938: 221-230, 2001. Abstract.

Osawa et al. "Long-Term Lymphohematopoietic Reconstitution by a Single CD34+Low/Negative Hematopoietic Stem Cell", Science, 273(5272): 242-245, 1996.

Ostrakhovitch et al. Copper Ions Strongly Activate the Phosphoinositide-3-Kinase/Akt Pathway Independent of the Generation of Reactive Oxygen Species, Archives of Biochemistry and Biophysics, 397(2): 232-239, 2002. p. 235, col. 1, Paragraph 4-col. 2, Paragraph 2.

Pack et al. "Improved Bivalent Miniantibodies, With Identical Avidity as Whole Antibodies, Produced by High Cell Density Fermentation of*Escherichia coli*", Bio/Technology, 11: 1271-1277, 1993.

Paling et al. "Regulation of Embryonic Stem Cell Self-Renewal by Phosphoinositide 3-Kinase-Dependent Signaling", The Journal of Biological Chemistry, 279(46): 48063-48070, 2004.

Park, et al., "Phosphatidylinositol 3-kinase regulates PMA-induced differentiation and superoxide production in HL-60 cells.", *Immunopharmacol. Immunotoxicol*, 24(2):211-226 (2002).

Pei et al. "Bioreactors Mediate the Effectiveness of Tissue Engineering Scaffolds", The FASEB Journal, 16: 1691-1694, 2002.

Peled et al. "Cellular Copper Content Modulates Differentiation and Self-Renewal in Cultures of Cord Blood-Derived CD34+ Cells", British Journal of Haematology, 116(3): 655-661, 2002.

Peled et al., "Chelatable Cellular Copper Modulates Differentiation and Self-Renewal of Cord Blood-Derived Hematopoietic Progenitor Cells", *Exp Hematol*, 33:1092-1100 (2005).

Peled et al. "Copper Chelators Sustain Long-Term Expansion of Cord-Blood CD 34+ Cultures Initiated With IL-3 and G-CSF—Late Acting, Differentiation-Inducing Cytokines", Blood, 96(1): 773a, 2000. Abstract # 3343.

Peled et al. "Identification of A Serum-Derived Differentiation-Inducing Activity as the Copper-Binding Protein Ceruloplasmin", Blood, 92(10, Suppl.1, Part 1-2): 618A-619A, 1998. Abstract.

Peled et al. "Linear Polyamine Copper Chelator Tetraethylenepentamine Augments LongTerm Ex Vivo Expansion of Cord Blood-Derived CD34+ Cells and Increases Their Engraftment Potential in NOD/SCID Mice", Experimental Hematology, 32: 547-555, 2004.

Peled et al. "Regulation of Long-Term Expansion of Hemopoietic Stem/Progenitor Cells (HPC) by Intracellular Copper Content", Blood, 96(11/Pt.1): 776a-777a, 2000.

Peled et al. "Copper chelators enable long term CFU and CD34+ cells expansions in cultures initiated with the entire mononuclear cell (MNC) fraction.", Blood, 100 (11), 2002. Abstract # 4076.

Pera MF. 2001, Human pluripotent stem cells: a progress report. Curr Opin Gen Devel 11:595-599.

Percival "Copper and Immunity", American Journal of Clinical Nutrition, 67(5 Suppl.): 1064S-1068S, 1998. p. 1066, 1-h col. § 2-r-h col. § 2.

Percival "Neutropenia Caused by Copper Deficiency: Possible Mechanism of Action", Nutrition Reviews, 53(3):59-66, 1995.

Percival et al. "Copper Is Required to Maintain Cu/Zn-Superoxide Dismutase Activity During HL-60 Cell Differentiation", Proc. Soc. Exp. Biol. Med., 203: 78-83, 1993.

Percival et al. "HL-60 Cells Can Be Made Copper Deficient by Incubating With Tetraethylenepentamine 1,2,3", Journal of Nutrition, 122(12): 2424-2429, 1992.

Perrotti et al. "Overexpression of the Zinc Finger Protein MZF1 Inhibits Hematopoietic Development From Embryonic Stem Cells: Correlation With Negative Regulation of CD34 and C-MYB Promoter Activity", Molecular and Cellular Biology, 15(11): 6075-6087, 1995.

Peters et al. "Long-Term Ex Vivo Expansion of Human Fetal Liver Primitive Haematopoietic Progenitor Cells in Stroma-Free Cultures", British Journal of Haematology, 119: 792-802, 2002.

Petersen et al. "Bone Marrow as a Potential Source of Hepatic Oval Cells", Science, 284(5417): 1168-1170, 1999. Abstract.

Petersen et al. "Hepatic Oval Cells Express the Hematopoietic Stem Cell Marker Thy-1 in the Rat", Hepatology, 27(2): 433-445, 1998.

Petti et al. "Complete Remission Through Blast Cell Differentiation in PLZF/RARα-Positive Acute Promyelocytic Leukemia: In Vitro and In Viva Studies", Blood, 100(3): 1065.1067, 2002.

Petzer et al. "Differential Cytokine Effects on Primitive (CD34+CD38−) Human Hematopoietic Cells: Novel Responses to Flt3-Ligand and Thrombopoietin", Journal of Experimental Medicine, 183: 2551-2558, 1996.

Petzer et al., "Self-Renewal of Primitive Human Hematopoietic Cells (Long-Term-Culture-Initiating Cells) in vitro and Their Expansion in Defined Medium", *Proc Natl Acad Sci USA*, 93:1470-1474 (1996).

Piacibello et al. "Extensive Amplification and Self-Renewal of Human Primitive Hematopoietic Stem Cells From Cord Blood", Blood, 89(8): 2644-2653, 1997.

Pickart et al. "Growth Modulating Plasma Tripeptide May Function by Facilitating Copper Uptake Into Cells", Nature, 288(18/25): 715-717, 1980.

Podesta et al. "Extracellular Cyclic ADP-Ribose Increases Intracellular Free Calcium Concentration and Stimulates Proliferation of Human Hematopoietic Progenitors", FASEB Journal, 14(5): 680-690, 2000. Fig. 1.

Podestá et al. "Cyclic ADP-Ribose Generation by CD38 Improves Human Hemopoietic Stem Cell Engraftment Into NOD/SCID Mice", The FASEB Journal, 17: 310-312, 2003.

Porter "The Hydrolysis of Rabbit γ-Globulin and Antibodies With Crystalline Papain", Biochemical Journal, 73: 119-126, 1959.

Porter et al. "Graft-Versus-Leukemia Effect of Allogeneic Bone Marrow Transplantation and Donor Mononuclear Cell Infusions", Cancer Treatment & Research, 77: 57-85, 1997. Abstract.

Presta "Antibody Engineering", Current Opinion in Structural Biology, 2: 593-596, 1992.

Puccetti et al. "AML-Associated Translocation Products Block Vitamin D3-Induced Differentiation by Sequestering the Vitamin D3 Receptor", Cancer Research, 62: 7050-7058, 2002.

Punzel et al. "The Type of Stromal Feeder Used in Limiting Dilution Assays Influences Frequency and Maintenance Assessment of human Long-Term Culture Initiating Cells", Leukemia, 13: 92-97, 1999.

Purdy et al. "Large Volume Ex Vivo Expansion of CD34+-Positive Hematopoietic Progenitor Cells for Transplantation", Journal of Hematotherapy, 4: 515-525, 1995.

Purton et al. "All-Trans Retinoic Acid Delays the Differentiation of Primitive Hematopoietic Precursors (lin⁻c-kit+sca-1+) While Enhancing the Terminal Maturation of Committed Granulocyte/MonoCyte Progenitors", Blood, 94(2); 483-495, 1999.

Purton et al. "All-Trans Retinoic Acid Enhances the Long-Term Repopulating Activity of Cultured Hematopoietic Stem Cells", Blood, 95(2): 470-477, 2000. Abstract.

Purton et al. "All-Trans Retinoic Acid Facilitates Oncoretrovirus-Mediated Transduction of Hematopoietic Repopulating Stem Cells", J. Hematother. Stem Cell Res., 10(8): 815-825, 2001. Abstract.

Quantin et al. "Adenovirus as an Expression Vector in Muscle Cells In Vivo", Proc. Natl. Acad. Sci. USA, 89: 2581-2584, 1992.

Rajur et al. "Covalent Protein-Oligoneucleotide Conjugates for Efficient Delivery of Antisense Molecules", Bioconjugate Chemistry, 8(6): 935-940, 1997.

Ramsfjell et al. "Distinct Requirements for Optimal Growth and In Vitro Expansion of Human CD34+CD38-Bone Marrow Long-Term Culture-Initiating Cells (LTC-IC), Extended LTC-IC, and Murine In Vivo Long-Term Reconstituting Stem Cells", Blood, 94(12): 4093-4102, 1999.

Ratajczak et al. "Effect of Basic (FGF-2) and Acidic (FGF-1) Fibroblast Growth Factors on Early Haemopoietic Cell Development", British Journal of Hematology, 93: 772-782, 1996.

Ratajczak MZ et al., "Hunt for pluripotent stem cell—regenerative medicine search for almighty cell.", J Autoimmun 30: 151-162, 2008.

Reeves et al. "High Zinc Concentrations in Culture Media Affect Copper Uptake and Transport in Differentiated Human Colon Adenocarcinoma Cells", Journal of Nutrition, 126(6): 1701-1712, 1996. Abstract.

Reid et al. "Interactions of Tumor Necrosis Factor With Granulocyte-Macrophage Colony-Stimulating Factor and Other Cytokines in the Regulation of Dendritic Cell Growth In Vitro From Early Bipotent CD34+ Progenitors in Human Bone Marrow", Journal of Immunology, 149(8): 2681-2688, 1992. Abstract.

Reya, T., "Regulation of Hematopoietic Stem Cell Self-Renewal", *Rec Prog Horm Res*, 58:283-295 (2003).

Reyes et al. "Origin of Endothelial Progenitors in Human Postnatal Bone Marrow", Journal of Clinical Investigation, 109: 337-346, 2002.

Riechmann et al. "Reshaping Human Antibodies for Therapy", Nature, 332: 323-327, 1988.

Robinson et al., "Superior Ex vivo Cord Blood Expansion Following Co-Culture With Bone Marrow-Derived Mesenchymal Stem Cells", *Bone Marrow Transplant.*, 37:359-366 (2006).

Rosenfeld et al. "Adenovirus-Mediated Transfer of a Recombinant α1-Antitrypsin Gene to the Lung Epithelium In Vivo", Science, 252: 431-434, 1991.

Rosenfeld et al. "In Vivo Transfer of the Human Cystic Fibrosis Transmembrane Conductance Regulator Gene to the Airway Epithelium", Cell, 68: 143-155, 1992.

Ross et al. "Chelometric Indicators Titrations With the Solid-State Cupric Ion-Selective Electrode", Analytical Chemistry, 41(13): 1900-1902, 1969.

Rusten et al. "The RAR-RXR as Well as the RXR-RXR Pathway Is Involved Signaling Growth Inhibition of Human CD34+ Erythroid Progenitor Cells", Blood, 87(5): 1728-1736, 1996. Abstract.

Ryu et al. "Adenosine Triphosphate Induces Proliferation of Human Neural Stem Cells: Role of Calcium and P70 Ribosomal Protein S6 Kinase", Journal of Neuroscience Research, 72: 352-362, 2003.

Sammons et al. "Mechanisms Mediating the Inhibitory Effect of All-Trans Retinoic Acid on Primitive Hematopoietic Stem Cells in Human Long-Term Bone Marrow Culture", Stem Cells, 18(3): 214-219, 2000.

Samulski et al. "Helper-Free Stocks of Recombinant Adeno-Associated Viruses: Normal Integration Does Not Require Viral Gene Expression", Journal of Virology, 63(9): 3822-3828, 1989.

Santoro et al. "A General Purpose RNA-Cleaving DNA Enzyme", Proc. Natl. Acad. Sci. USA, 94: 4262-4266, 1997.

Sato et at. "In Vitro Expansion of Human Peripheral Blood CD34+ Cells", Blood, 82(12): 3600-3609, 1993.

Sauve et al. "Mechanism-Based Inhibitors of CD38: A Mammalian Cyclic ADP-Ribose Synthetase", Biochemistry, 41(26): 8455-8463, 2002.

Schechter et al. The Molecular Basis of Blood Diseases, p. 179-218, 1987.

Schmetzer et al. "Effect of GM-CSF, 1,25-Dihydroxycholecalciferol (Vit. D) and All-Trans-Retinocin Acid (ATRA) on the Proliferation and Differentiation of MDS-Bone Marrow (BM)-Cells In Vitro", Hematology, 2: 11-19, 1997.

Schwartz et al. "In Vitro Myelopoiesis Stimulated by Rapid Medium Exchange and Supplementation With Hematopoietic Growth Factors", Blood, 78(12): 3155-3161, 1991.

Seed "An LFA-3 cDNA Encodes a Phospholipid-Linked Membrane Protein Homologous to Its Receptor CD2", Nature, 329: 840-842, 1987.

Sekhar et al. "Retroviral Transduction of CD34-Enriched Hematopoietic Progenitor Cells Under Serum-Free Conditions", Human Gene Therapy, 7: 33-38, 1996.

Selden "Transfection Using DEAE-Dextran", Short Protocols in Molecular Biology, Unit 9.2: 9-9-9-11, 1984.

Selden et al. "Optimization of Transfection", Short Protocols in Molecular Biology, Unit 9.4: 262-263, 1984.

Sergeant et al. "Iron and Copper Requirements for Proliferation and Differentiation of a Human Promyelocytic Leukemia Cell Line (HL-60)", Journal of Cellular Physiology, 163(3): 477-485, 1995.

Shimakura et al. "Murine Stromal Cell Line HESS-5 Maintains Reconstituting Ability of Ex Vivo-Generated Hematopoietic Stem Cells From Human Bone Marrow and Cytokine-Mobilized Peripheral Blood", Stem Cells, 18: 183-189, 2000.

Shimizu et al. "Treatment and Management of Wilson's Disease", Pediatrics International, 41(4): 419-422, 1999. Abstract.

Sieff, et al., "Changes in cell surface antigen expression during hemopoietic differentiation.", *Blood*, 60(3):703-713 (1982).

Sigurdsson et al. "Copper Chelation Delays the Onset of Prion Disease", Journal of Biological Chemistry, 278(47): 46199-202, 2003.

Silvenoinen et al. "CD38 Signal Transduction in Human B Cell Precursors. Rapid Induction of Tyrosine Phosphorylation, Activation of Syk Tyrosine Kinase and Phosphorylation of Phospholipase GGamma and Phosphatidylinositol 3-Kinase", Journal of Immunology, 156(1): 100-107, 1996. Abstract.

Simon et al. "Copper Deficiency and Sideroblastic Anemia Associated With Zinc Ingestion", American Journal of Hematology, 28: 181-183, 1988.

Slavin et al. "Donor Lymphocyte Infusion: The Use of Alloreactive and TumorReactive Lymphocytes for Immunotherapy of Malignant and Nonmalignant Diseases in Conjunction With Allogeneic Stem Cell Transplantation", Journal of Hematotherapy & Stem Cell Research, 11: 265-276, 2002.

Slavin et al. "Treatment of Leukemia by Alloreactive Lymphocytes and Nonmyeloablative Stem Cell Transplantation", Journal of Clinical Immunology, 22(2): 64-69, 2002.

Spencer et al. "Controlling Signal Transduction With Synthetic Ligands", Science, 262: 1019-1024, 1993.

Sprangrude et al. "Purification and Characterization of Mouse Hematopoietic Stem Cells", Science, 241(4861): 58-62, 1988. Abstract.

Suda et al. "A Study of Trientine Therapy in Wilson's Disease With Neurology Symptoms", No To Hattatsu, 25(5): 429-34, 1993. Abstract.

Szilvassy et al. "Differential Homing and EngraftmentProperties of Hematopoetic Progenitor Cells From Murine Bone Marrow Mobilized Peripheral Blood Cells and Fetal Liver", Blood, 98(7): 2108-2115, 2001.

Takeshita et al. "Selective Stimulation by Ceramide of the Expression of the α Isoform of Retinoic Acid and Retinoid X Receptors in Osteoblastic Cells", Journal of Biological Chemistry, 275(41): 32220-32226, 2000.

Tashiro-Itoh et al. "Metallothionein Expression and Concentrations of Copper and Zinc Are Associated With Tumor Differentiation in Hepatocellular Carcinoma", Liver, 17: 300-306, 1997.

Tateishi-Yuyama et al., "Therapeutic angiogenesis for patients with limb ischaemia by autologous transplantation of bone-marrow cells: a pilot study and a randomised controlled trial", *The Lancet*, 360:427-435 (2002).

Tateno et al., "Long-term cultivation of adult rat hepatocytes that undergo multiple cell divisions and express normal parenchymal phenotypes.", *Am. J. Pathol.*, 148(2):383-392 (1996).

Tetraethylene Pentamine DOD Hazardous Material Information; 6810-00F017710 (1991).

Thiotepa Product Identification Sheet; THIOTEPA; EM Science, 6505-01-047-3872 (1990).

Todisco et al. "CD38 Ligation Inhibits Normal and Leukemic Myelopoiesis", Blood, 95(2): 535-542, 2000. Abstract.

Tratschin et al. "A Human Parvovirus, Adeno-Associated Virus, as a Eucaryotic Vector: Transient Expression and Encapsidation of the Procaryotic Gene for Chloramphenieol Acetyltransferase", Molecular and Cellular Biology, 4(10): 2072-2081, 1984.

Tratschin et al. "Adeno-Associated Virus Vector for High-Frequency Integration, Expression, and Rescue of Genes in Mammalian Cells", Molecular and Cellular Biology, 5(11): 3251-3260, 1985.

Tratschin et al. "Genetic Analysis of Adeno-Associated Virus: Properties of Deletion Mutants Constructed In Vitro and Evidence for an Adeno-Associated Virus Replication Function", Journal of Virology, 51(3): 611-619, 1984.

Trientine (Systemic) MEDLINEPlus Drug Information.

Triethylenetetramine Product Identification Sheet; TETA, TX1235; EM Science, 6810-00N052879 (1991).

Tuba et al. "Synthesis and Structure—Activity Relationships of Neuromuscular Blocking Agents", Current Medicinal Chemistry, 9: 1507-1536, 2002.

Turnpenny L et al., "Evaluating human embryonic germ cells: concorl and conflict as pluripotent stem cells.", Stem Cells 24: 212-220, 2006.

Ueno et al. "A Novel Retinoic Acid Receptor (RAR)-Selective Antagonist Inhibits Differentiation and Apoptosis of HL-60 Cells: Implications of RAR?-Mediated Signals in Myeloid Leukemic Cells", Leukemia Research, 22(6): 517-525, 1998.

Van Beusechem et al. "Long-Term Expression of human Adenosine Deaminase in Rhesus Monkeys Transplanted With Retrovirus-Infected Bone-Marrow Cells", Proc. Natl. Acad. Sci. USA, 89: 7640-7644, 1992.

Verfaillie "Can Human Hematopoietic Stem Cells Be Cultured Ex Vivo?", Stem Cells, 12(5): 466-476, 1994. Abstract.

Verfaillie "Direct Contact Between Human Primitive Hematopoietic Progenitors and Bone Marrow Stroma Is Not Required for Long-Term In Vitro Hematopoiesis", Blood, 79(11): 2821-2826, 1992.

Verhoeyen et al. "Reshaping Human Antibodies: Grafting an Antilysozyme Activity", Science, 239: 1534-1536, 1988.

Verlinden et al. "Interaction of Two Novel 14-Epivitamin D3 Analogs With Vitamin D3 Receptor-Retinoid X Receptor Heterodimers on Vitamin D3 Response Elements", Journal of Bone and Mineral Research, 16(4): 625-638, 2001.

Vilensky et al. "British Anti-Lewisite (Dimercaprol): an Amazing History", Ann. Emerg. Med., 41(3): 378-83, 2003. Abstract.

Vlahos, et al., "A specific inhibitor of phosphatidylinositol 3-kinase, 2-(4-monaholiny1)-8-phenyl-4H-1-benzopyran-4-one (LY294002).", .J. Biol. Chem., 269(7):5241-5248 (1994).

Wagers et al., "Little Evidence for Developmental Plasticity of Adult Hematopoietic Stem Cells", Science, 297(5590):2256-2259 (2002). Abstract.

Wall et al. "Inhibition of the Intrinsic NAD+ Glycohydrolase Activity of CD38 by Carbocyclic NAD Analogues", Biochemical Journal, 335(3): 631-636, 1998.

Walton et al. "Prediction of Antisense Oligonucleotide Binding Affinity to a Structured RNA Target", Biotechnology and Bioengineering, 65(1): 1-9, 1999.

Wang et al. "In Vitro Culture of Umbilical Cord Blood MNC and CD34+ Selected Cells", Sheng Wu Gong Cheng Xue Bao, 18(3): 343-347, 2002. Abstract.

Wang et al. "PH-Sensitive Immunoliposomes Mediate Target-Cell-Specific Delivery and Controlled Expression of a Foreign Gene in Mouse", Proc. Natl. Acad. Sci. USA, 84: 7851-7855, 1987.

Weissmann "Translating Stem and Progenitor Cell Biology to the Clinic: Barriers and Opportunities", Science, 287(5457): 1442-1446, 2000. Abstract.

Wendling et al. "Retinoid X Receptor Are Essential for Early Mouse Development and Placentogenesis", Proc. Natl. Acad. Sci. USA, 96(2): 547-551, 1999.

Whitlow et al. "Single-Chain Fv Proteins and Their Fusion Proteins", Methods: A Companion to Methods in Enzymology, 2(2): 97-105, 1991.
Wick et al. "New Ways in Hepatocyte Cultures: Cell Immobilisation Technique", ALTEX, 14(2): 51-56, 1997. Abstract.
Wilson et al. "Hepatocyte-Directed Gene Transfer In Vivo Leads to Transient Improvement of Hypercholesterolemia in Low Density Lipoprotein Receptor-Deficient Rabbits", The Journal of Biological Chemistry, 267(2): 963-967, 1992.
Wilson et al. "Retrovirus-Mediated Transduction of Adult Hepatocytes", Proc. Natl. Acad. Sci. USA, 85: 3014-3018, 1988.
Wolff et al. "Direct Gene Transfer Into Mouse Muscle In Vivo", Science, 247: 1465-1468, 1990.
Wondisford et al. "Cloning of the Human Thyrotropin β-Subunit Gene and Transient Expression of Biologically Active Human Thyrotropin After Gene Transfection", Molecular Endocrinology, 2: 32-39, 1988.
Wu et al. "Receptor-Mediated Gene Delivery and Expression In Vivo", The Journal of Biological Chemistry, 263(29): 14621-14624, 1988.
Wulf et al. "Somatic Stem Cell Plasticity: Current Evidence and Emerging Concepts", Experimental Hematology, 29: 1361-1370, 2001.
Yang et al. "In Vitro Trans-Differentiation of Adult Hepatic Stem Cells Into Pancreatic Endocrine Hormone-Producing Cells", Proc. Natl. Acad. Sci. USA, 99(12): 8078-8083, 2002.
Yin et al. "AC133, A Novel Marker for Human Hematopoietic Stem and Progenitor Cells", Blood, 90(12): 5002-5012, 1997.
Ylä-Herttuala et al., "Gene transfer as a tool to induce therapeutic vascular growth",Nature Medicine, 9(6): 694-701 (2003).
Yoon et al., "Clonally Expanded Novel Multipotent Stem Cells From Human Bone Marrow Regenerate Myocardium After Myocardial Infarction", J. Clin. Invest., 115(2)326-338 (2005).
Zenith "Zenith and US Robotics, A Complete Network Solution for Data Modem Communications Over One-Way Cable Plants", Zenith Network Systems Data Business Unit.
Zidar et al. "Observations on the Anemia and Neutropenia of Human Copper Deficiency", American Journal of Hematology, 3: 177-185, 1977.
Zocchi et al. "Ligand-Induced Internalization of CD38 Results in Intracellular Ca2+ Moblization: Role of NAD+ Transport Across Cell Membranes", The FASEB Journal, 13(2): 273-283, 1999. Abstract.
Zon et al. "Developmental Biology of Hematopoiesis", Blood, 86(8): 2876-2891, 1995.
European Patent Office Re.: Application No. 05784625.5 Supplementary Partial European Search Report and the European Search Opinion Dated Aug. 11, 2009.
Li et al. "Cell Life Versus Cell Longevity: Ther Mysteries Surrounding the NAD+ Precursor Nicotinamide", Current Medicinal Chemistry, XP0002539111, 13(8): 883-895, Apr. 2006.
Robinson et al. "Ex Vivo Expansion of Umbilical Cord Blood", Cytotherapy, XP009120788, 7(3): 243-250, 2005.
Segev et al. "Differentiation of Human Embryonic Stem Cells Into Insulin-Producing Clusters", Stem Cells, XP009038283, 22(3): 265-274, 2004.
Vaca et al. "Nicotinamide Induces Both Proliferation and Differentiation of Embryonic Stem Cells Into Insulin-Producing Cells", Transplantion Proceedings, XP002539110, 35(5): 2021-2023, 2003.
European Patent Office Re.: Application No. 05784625.5 Communication Pursuant to Article 94(3) EPC Dated Nov. 17, 2009.
European Patent Office Re.: Application No. 06821601.9 Communication Pursuant to Article 94(3) EPC Dated Aug. 20, 2009.
International Searching Authority Re.: Application No. PCT/IL0500994 International Search Report and the Written Opinion Dated Jul. 8, 2008.
International Searching Authority Re.: Application No. PCT/IL2006/001381 International Search Report and the Written Opinion Dated May 11, 2007.
Israel Patent Office Re.: Application No. 181976 and Its Translation Into English Office Action Dated Nov. 29, 2009.
Singapore Intellectual Property Office Re.: Application No. SG 200804154-3 Search Report and Written Opinion Dated Aug. 10, 2009.
Blyszczuk et al., "Embryonic stem cells differentiate into insulin-producing cells without selection of nestin-expressing cells." Int J Dev Biol. 48(10):1095-104, 2004.
Chen et al., "Differentiation of rat marrow mesenchymal stem cells into pancreatic islet betacells." World J Gastroenterol. 10(20):3016-20, 2004.
Chivu et al., "In vitro hepatic differentiation of human bone marrow mesenchymal stem cells under differential exposure to liver-specific factors." Transl Res. 154(3):122-32. Epub Jun. 24, 2009.
Zulewski et al., "Multipotential nestin-positive stem cells isolated from adult pancreatic islets differentiate ex vivo into pancreatic endocrine, exocrine, and hepatic phenotypes."Diabetes. 50(3):521-33, 2001.
International Preliminary Report on Patentability Dated Jun. 12, 2008 From the International Bureau of WIPO Re.: Application No. PCT/IL2006/001381.
International Preliminary Report on Patentability Dated Jan. 22, 2009 From the International Bureau of WIPO Re.: Application No. PCT/IL2005/000994.
Official Action Dated Sep. 20, 2006 From the US Patent and Trademark Office Re.: U.S. Appl. No. 11/289,004.
Official Action Dated Jun. 28, 2006 From the US Patent and Trademark Office Re.: U.S. Appl. No. 11/289,004.
Response Dated Mar. 4, 2010 to Communication Pursuant to Article 94(3) EPC of Nov. 17, 2009 From the European Patent Office Re.: Application No. 05784625.5.
Response Dated Mar. 8, 2010 to Official Action of Oct. 23, 2009 From the US Patent and Trademark Office Re.: U.S. Appl. No. 11/606,525.
Response Dated Feb. 18, 2010 to Communication Pursuant to Article 94(3) EPC of Aug. 20, 2009 From the European Patent Office Re.: Application No. 06821601.9.
Response Dated Jan. 31, 2010 to Search Report and Written Opinion of Aug. 10, 2009 From the Intellectual Property Office of Singapore Issued by the Australian Patent Office Re.: Application No. SG 200804154-3.
McLaughlin et al. "Adeno-Associated Virus General Transduction Vectors: Analysis of Proviral Structures", Journal of Virology, 62(6): 1963-1973, 1988.
Wasa et al. "Copper Deficiency With Pancytopenia During Total Parenteral Nutrition", Journal of Parenteral and Enteral Nutrition, 18(2): 190-192, 1994.
Examination Report Dated Jun. 10, 2010 From the Intellectual Property Office of Singapore Issued by the Australian Patent Office Re.: Application No. SG 200804154-3.
Communication From the Israel Patent Office Re. Application No. 191669 Office Action Dated Jul. 12, 2010.
Communication Pursuant to Article 94(3) EPC Dated Aug. 5, 2010 From the European Patent Office Re. Application No. 05784625.5.
Handgretinger et al., "Biology and plasticity of CD133+ hematopoietic stem cells", Ann. N.Y. Acad. Sci., 996:141-151 (2003).
Morita et al., "Heterogeneity and hierarchy within the most primitive hematopoietic stem cell compartment", J. Exp. Med., 207(6):1173-1182 (2010).

* cited by examiner

METHODS OF EX VIVO HEMATOPOIETIC STEM CELL EXPANSION BY CO-CULTURE WITH MESENCHYMAL CELLS

RELATED APPLICATIONS

The present application is a continuation of, and claims priority under 35 USC§365(c) to, PCT/IL2005/000994, filed Sep. 15, 2005, which claims priority to, and the benefit from, U.S. Ser. No. 60/610,171 filed Sep. 16, 2004. The contents of all of these applications are incorporated herein by reference in their entireties.

FIELD AND BACKGROUND OF THE INVENTION

The present invention relates to methods of ex-vivo expansion of stem cells, such as hematopoietic stem cells, by co-culture with mesenchymal cells, to expanded populations of renewable stem cells expanded by co-culture with mesenchymal cells, and to their uses. In particular, fetal and/or adult hepatic, and umbilical cord blood, bone marrow or peripheral blood derived hematopoietic stem cells expanded ex-vivo along with mesenchymal cells, according to the methods of the present invention, can be transplanted into recipients, for example, following myeloablation.

Expansion of Stem and Progenitor Cell Populations:

While many methods for stimulating proliferation of stem and progenitor cell populations have been disclosed [see, for example, Czyz et al, Biol Chem 2003; 384:1391-409; Kraus et al., (U.S. Pat. No. 6,338,942, issued Jan. 15, 2002); Rodgers et al. (U.S. Pat. No. 6,335,195 issued Jan. 1, 2002); Emerson et al. (Emerson et al., U.S. Pat. No. 6,326,198, issued Dec. 4, 2001) and Hu et al. (WO 00/73421 published Dec. 7, 2000) and Hariri et al (US Patent Application No. 20030235909)] few provide for reliable, long-term expansion, without the accompanying differentiation that naturally occurs with growth of stem or progenitor cells in culture.

Up until recently, expansion of renewable stem cells has been achieved either by growing the stem cells over a feeder layer of fibroblast cells, or by growing the cells in the presence of the early acting cytokines thrombopoietin (TPO), interleukin-6 (IL-6), an FLT-3 ligand and stem cell factor (SCF) (Madlambayan G J et al. (2001) J Hematother Stem Cell Res 10: 481, Punzel M et al. (1999) Leukemia 13: 92, and Lange W et al. (1996) Leukemia 10: 943). While expanding stem cells over a fibroblast feeder layer results in vast, substantially endless cell expansion, expanding stem cells without a feeder layer, in the presence of the early acting cytokines listed above, results in an elevated degree of differentiation (see Leslie N R et al. (Blood (1998) 92: 4798), Petzer A L et al. (1996) J Exp Med Jun 183: 2551, Kawa Y et al. (2000) Pigment Cell Res 8: 73).

Recently, however, methods for feeder-layer free expansion of stem cells ex-vivo have been disclosed. PCT IL99/00444 to Peled et al., filed Aug. 17, 1999, which is incorporated by reference as if fully set forth by reference herein, and from which the present invention derives priority, disclosed methods of imposing proliferation yet restricting differentiation of stem and progenitor cells by treating the cells with chelators of transitional metals. While reducing the invention to practice, they uncovered that heavy metal chelators having a high affinity for copper, such as tetraethylpentamine (TEPA), greatly enhanced the fraction of $CD34^+$ cell and their long-term clonability in cord-blood-derived, bone marrow-derived, and peripheral blood derived stem and progenitor cells. Facilitation of proliferation while inhibiting differentiation was also observed in erythroid progenitor cells, cultured mouse erythroleukemia cells, embryonal stem cells, and hepatocytes in primary hepatocyte culture treated with TEPA.

PCT IL03/00062, also to Peled et al., filed Jan. 23, 2003, which is incorporated by reference as if fully set forth herein, and from which the present invention derives priority, discloses a similar effective promotion of long term ex vivo stem cell proliferation, while inhibiting differentiation, using TEPA-Cu chelates as well as the chelator TEPA. Surprisingly, this effect of TEPA and TEPA-chelates was also demonstrated using as a starting population an un-selected peripheral mononuclear fraction. The results described therein clearly show that stem and progenitor hematopoietic cells may be substantially expanded ex vivo, continuously over at least 12 weeks period, in a culture of mixed (mononuclear fraction) blood cells, with no prior purification of $CD_{34}^+$ cells.

PCT IL 03/00064, also to Peled et al., filed Jan. 26, 2003, which is incorporated by reference as if fully set forth herein, and from which the present invention derives priority, teaches the ex-vivo expansion and inhibition of hematopoietic stem and progenitor cells using conditions and various molecules that interfere with CD38 expression and/or activity and/or with intracellular copper content, for inducing the ex-vivo expansion of hematopoietic stem cell populations. The small molecules and methods include linear polyamine chelators and their chelates, nicotinamide, a nicotinamide analog, a nicotinamide or a nicotinamide analog derivative or a nicotinamide or a nicotinamide analog metabolite, a PI 3-kinase inhibitor, conditions for reducing a capacity of the hematopoietic mononuclear cells in responding to retinoic acid, retinoids and/or Vitamin D and reducing the capacity of the cell in responding to signaling pathways involving PI 3-kinase.

Surprisingly, the inventors also showed that exposure of hepatocytes in primary culture to the small molecules, and conditions described hereinabove stimulated hepatocyte proliferation, greatly expanding the fraction of undifferentiated and immature hepatocytes (as determined by α-feto-protein expression, OC3 marker expression and oval cell morphology). Thus, using the methods described, adult stem and progenitor cells of hematopoietic and non-hematopoietic origin can provide expanded populations of cells for transplantation into endodermally derived organs.

PCT IL 03/00681, also to Peled et al, filed Aug. 17, 2003, which is incorporated by reference as if fully set forth herein, and from which the present invention derives priority, discloses methods of ex-vivo expanding a population of hematopoietic stem cells present, even as a minor fraction, in hematopoietic mononuclear cells, without first enriching the stem cells, while at the same time, substantially inhibiting differentiation of the hematopoietic stem cells. Cells thus expanded can be used to efficiently provide ex-vivo expanded populations of hematopoietic stem cells without prior enrichment of the hematopoietic mononuclear cells for stem cells suitable for hematopoietic cell transplantation, for genetic manipulations for cellular gene therapy, as well as in additional application such as, but not limited to, adoptive immunotherapy, implantation of stem cells in an in vivo cis-differentiation and trans-differentiation settings, as well as, ex-vivo tissue engineering in cis-differentiation and trans-differentiation settings.

PCT IL 2004/000215, also to Peled et al., filed Mar. 4, 2004, which is incorporated by reference as if fully set forth herein, and from which the present invention derives priority, further demonstrated the self-renewal of stem/early progenitor cells, resulting in expansion and inhibition of differentiation in stem cells of hematopoietic origin and non-hematopoietic origin by exposure to low molecular weight inhibitors of PI 3-kinase, disruption of the cells' PI 3-K signaling pathways.

PCT IL 2005/000753, also to Peled et al., filed Jul. 14, 2005, which is incorporated by reference as if fully set forth herein, and from which the present invention derives priority, discloses methods of expansion and inhibition of differentiation in stem cells of hematopoietic origin by exposure to inhibitors of the sirtuin family of enzymes, such as nicotinamide and splitomycin, resulting in extensive expansion of a cell population that displays phenotypic and functional characteristics of primitive hematopoietic progenitor cells.

PCT IL 2004/000644, also to Peled et al., filed Jul. 15, 2004, which is incorporated by reference as if fully set forth herein, and from which the present invention derives priority, discloses methods of ex-vivo expansion of endodermally-derived and non-endodermally-derived progenitor and stem cells, expanded populations of renewable progenitor and stem cells and their use for transplantation into solid organs for repopulation and treatment of diseases of endodermally derived organs such as liver and pancreas.

Hematopoietic Cell—Mesenchymal Cell Interactions:

Mature blood cells are derived from undifferentiated stem and progenitor cells in a highly complex series of maturational and divisional steps that occur in different tissues during embryonic development. The microenvironment seems to be an important factor influencing the proliferative activity and differentiation process of the stem and progenitor cells by local positive and negative signaling to the target cells (Williams D A. Stem cell model of hematopoiesis. In: Hoffman R, et al., eds. Hematology: Basic Principles and Practice. 2nd ed. New York, N.Y.: Churchill Livingstone; 1995:180). Within the bone marrow stroma there exists a subset of nonhematopoietic cells referred to as mesenchymal stem (MSC) or mesenchymal progenitor cells (MPC). Mesenchymal progenitor cells do not express the typical hematopoietic antigens, CD45, CD34, HLA-DR and CD14 and they are positive for CD105, CD49b, CD73 and HLA class 1. However, none of these markers is specific for mesenchymal progenitor cells. Recently, Thomas et al (US Patent Application No. 20040058397) has disclosed additional combinations of antibody markers to identify and enrich mesenchymal progenitor cells.

The following 3 mechanisms have been proposed to explain the role of non-hematopoietic stromal cells in the regulation of proliferation and differentiation of hematopoietic stem cells (Long M W. Exp Hematol. 1992; 20:288-301): (a) cytokine receptor-ligand interaction, (b) interaction between adhesion molecules on hematopoietic cells and stromal cells, or with components of the extracellular matrix, or (c) direct cell-to-cell communication between stromal cells or between stromal cells and hematopoietic cells.

Gap Junctions: Very little is known about the regulatory mechanisms of direct cell-to-cell communication in the hematopoietic microenvironment. Intercellular gap junctions represent the most well known intercellular communication system, and they are characterized by the existence of plaques of narrow channels between contacting cells. Each channel is formed by two hemichannels or hemiconnexons, and each one of them is contributed by one of two adjacent cells. A hemiconnexon is an oligomeric assembly of 6 polypeptide subunits, or connexins. Different tissue-specific connexins have been characterized and cloned (Kumar N M, Gilula N B Cell, 1996; 84:381-388). These channels form the only known system for direct diffusional exchange of ions and small molecules (ie, molecular weight<1000) between contacting cells (Spray D C. Circ Res. 1998; 83:679-681). Nutrients and second messengers can be quickly transported in this way through cell communication networks.

There are few reports analyzing the gap junctions in hematopoietic tissues. Rosendaal et al (J Cell Sci. 1994; 107: 29-37) reported on the basis of immunohistological studies that, in adult mouse bone marrow, the connexin (Cx43) gap junction epitopes are rare, but are up-regulated 80- to 100-fold in the marrow of the neonate or after forced stem cell division (by administering 5-fluorouracil [5-FU] or irradiation). This up-regulation occurs soon after an insult, before recognizable blood cells form, and around the time at which primitive stem cells are triggered to go into cycle, suggesting the presence of a latent network of gap junctions in normal hematopoietic tissues. Significantly, it has been reported that global blockade of all gap junctions and intercellular communication by amphotericin B reversibly inhibits the cobblestone area (CA) formation and hematopoiesis in stroma-containing cultures (Rosendaal M, et al. Leukemia. 1997; 11:1281-1289). In osteoblasts (Steinberg T H, et al. EMBO J. 1994; 13:744-750) and in fetal fibroblasts (Martyn K D, et al., Cell Growth Differ. 1997; 8:1015-1027), it has been shown that different gap junction proteins create channels with different conductance properties, suggesting that the gap junctions' contribution to regulation of cell functions might also differ between the different gap junctions. Thus, stromal-hematopoietic cell interaction may be mediated by gap junctions and/or other cell-to-cell connections.

Mesenchymal cells can be cultured. Two bone-marrow culture systems introduced in the mid-1970's have evolved as favored media for the in vitro analysis of mesengenesis and hematopoiesis. The Friedenstein culture system is based on the isolation of nonhematopoietic cells through their tendency to adhere to plastic. Once isolated, a monolayer of homogeneous, undifferentiated stromal cells is then grown in the culture medium, in the absence of hematopoietic cells. The stromal cells from this system have the potential to differentiate into discrete mesenchymal tissues, namely bone, cartilage, adipose tissue and/or muscle depending on specific growth supplements (Friedenstein, et al, Exp Hematol 1976 4, 267-74). In 1977, Dexter, et al. developed another bone marrow culture system for the study of hematopoiesis. (Dexter et al. J Cell Physiol 1977, 91:335-44). The Dexter culture does not require isolation of the mesenchymal cells before culturing, thus the monolayer of stromal cells is grown in the presence of hematopoietic cells. Greenberger later modified the Dexter system by the addition of hydrocortisone to the culture medium, making it more reproducible (Greenberger, Nature 1978 275, 752-4).

Co-culture of mesenchymal and hematopoietic cells has been previously reported. U.S. Pat. No. 6,030,836 to Thiede et al discloses the use of bone marrow mesenchymal stem cells or adipocytes in co-culture with autologous bone marrow hematopoietic stem cells, and the enhanced survival and expansion of hematopoietic progenitors such as CD34+, CD 34+/90+ and CD34+/CD14+. However, Thiede et al report that while the hematopoietic stem cell fraction of the cultured cells is not depleted, it grows only marginally.

Experiments with mesenchymal stem cells have indicated that they are "invisible" to the immune system. Normally, co-culturing cells from different individuals (allogeneic cells) results in T cell proliferation, manifested as a mixed lymphocyte reaction (MLR). However, when human mesenchymal stem cells are contacted with allogeneic T lymphocytes, in vitro, they do not generate an immune response by the T cells, i.e., the T cells do not proliferate, indicating that T cells are not responsive to mismatched mesenchymal stem cells (Maitra, et al., Bone Marrow Transplant 2004, 33:597-

604), despite the fact that the human mesenchymal stem cells express all of the class I and class II MHC surface molecules that render them immunogenic. Mesenchymal stem cells also actively reduce the allogeneic T cell response in mixed lymphocyte reactions in a dose dependent manner, and mesenchymal stem cells from different donors do not exhibit specificity of reduced response with regard to MHC type.

Thus, the use of mesenchymal cells, and mesenchymal cells culture in transplantation has been investigated. Using NOD/SCID mice, Noort, et al have demonstrated that co-transplantation of mesenchymal cells isolated as non-hematopoietic cells from fetal lung CD34+ cells significantly enhanced the engraftment of hematopoietic stem cells (Noort et al Exp Hematol 2002; 30:870-78). Similarly, Maitra et al (Maitra, et al., Bone Marrow Transplant 2004, 33:597-604) have demonstrated the successful repopulation of NOD/SCID mice with limited numbers of hematopoietic stem cells, augmented by co-infusion with unrelated human mesenchymal stem cells. Significantly, no enhancement was observed with a co-infusion with mouse mesenchymal stem cells. Human mesenchymal stem cells culture has also been shown to support the ex-vivo propagation of CD34+ cells, in the absence of direct contact between the mesenchymal and hematopoietic cells in culture, and enhance transplantation. (Sumner, et al, Cytother 2001 3; 422a). Therapeutic use of mesenchymal stem cells and stem cell culture has been investigated. Administration of expanded mesenchymal stem cell cultures has been proposed for treatment of articular disorders (US Patent Application No. 20040151703 to Ha, et al), Hurler syndrome and metachromatic leukodystrophy (Koc, et al, Bone Marrow Transplant. 2002; 30:215-22) and for connective tissue engraftment, as well as hematopoietic cell engraftment (U.S. Pat. No. 6,355,239, to Bruder et al). Koc, et al (J Clin Oncol, 2000, 18:307-16) reported the co-infusion of culture expanded autologous bone marrow mesenchymal stem cells (in DMEM and bovine fetal serum medium) and peripheral blood progenitor cells in 32 breast cancer patients after high dose chemotherapy, with no observed toxicity or reduced engraftment related to the mesenchymal cell administration. Infusion of allogeneic bone marrow derived mesenchymal stem cells for Hurler syndrome and metachromatic leukodystrophy (Koc, et al, Bone Marrow Transplant. 2002; 30:215-22) also indicated no toxicity and possible therapeutic value. Recently, Lazarus, et al (Biol. Blood Marrow Transplant. 2005; 11:389-98) reported the co-administration of culture expanded mesenchymal stem cells and hematopoietic stem cells from sib-matched donors to 46 hematopological malignancy patients following high dose chemotherapy, with no toxicity and an increased probability of successful transplant in the co-administered group.

Thiede et al (U.S. Pat. No. 6,030,836) disclose the use of co-cultured bone marrow hematopoietic stem cells and mesenchymal stem cells (or adipocytes), enriching the CD34+, CD34+/90+ and CD34+/CD14+ fraction of hematopoietic stem cells for engraftment. McIntosh et al (U.S. Pat. Nos. 6,368,636 and 6,875,430) teach the reduction of immune response to cellular transplant, and reduction in graft versus host disease, by infusion of mesenchymal stem cells before, after, or along with the transplanted cells. Seshi, et al (US Patent Application No. 2003000308) teaches the isolation of mesenchymal progenitor cells expressing different multiple cellular differentiation markers, such as fat, osteoblasts, smooth muscle and fibroblast markers, for treatment of graft versus host disease, and for enhanced transplantation.

Based on the above descriptions, it is clear that there is thus a widely recognized need for, and it would be highly advantageous to have, methods enabling efficient ex-vivo expansion of hematopoietic stem cells using co-culture of hematopoietic stem cells with mesenchymal cells, yielding large numbers of stem cell populations for transplantation, alone or along with the mesenchymal cells.

SUMMARY OF THE INVENTION

The present invention discloses methods of ex-vivo expansion of renewable populations of adult and/or fetal stem cells by ex-vivo co-culture with mesenchymal cells, populations of renewable stem cells expanded by co-culture with mesenchymal cells, and methods for the use thereof for transplantation into host subjects.

While reducing the present invention to practice, it was unexpectedly found that ex-vivo expansion of stem and progenitor cells using a unique culturing system and including co-culture with adherent mesenchymal cells, resulted in large populations of implantable stem cells, which can be used for therapeutic and clinical applications as is further detailed hereinunder.

According to one aspect of the present invention there is provided a method of expanding and at the same time inhibiting differentiation of a population of stem cells, the method comprising ex-vivo co-culturing the stem cells with mesenchymal cells under conditions which allow expanding and at the same time inhibiting differentiation of at least a portion of the stem cells, wherein said conditions are selected from the group consisting of: (i) conditions reducing expression and/or activity of CD38 in the cells; (ii) conditions reducing capacity of the cells in responding to signaling pathways involving CD38 in the cells; (iii) conditions reducing capacity of the cells in responding to retinoic acid, retinoids and/or Vitamin D in the cells; (iv) conditions reducing capacity of the cells in responding to signaling pathways involving the retinoic acid receptor, the retinoid X receptor and/or the Vitamin D receptor in the cells; (v) conditions reducing capacity of the cells in responding to signaling pathways involving PI 3-kinase; (vi) conditions wherein the cells are cultured in the presence of nicotinamide, a nicotinamide analog, a nicotinamide or a nicotinamide analog derivative or a nicotinamide or a nicotinamide analog metabolite; (vii) conditions wherein the cells are cultured in the presence of a copper chelator; (viii) conditions wherein the cells are cultured in the presence of a copper chelate; (ix) conditions wherein the cells are cultured in the presence of a PI 3-kinase inhibitor; and (x) conditions wherein the cells are cultured in the presence of an inhibitor of sirtuin enzymes.

According to another aspect of the present invention, undifferentiated stem cells expanded using the methods of the present invention can be used for transducing expanded, undifferentiated stem cells with an exogene. The method is effected by ex-vivo co-culturing the stem cells with mesenchymal cells according to the methods of the present invention to thereby obtain the expanded, undifferentiated cells; and transducing the expanded, undifferentiated stem cells with the exogene.

According to further features in preferred embodiments of the invention described below the transducing is effected by a vector comprising the exogene.

According to another aspect of the present invention there is provided a method of stem cells transplantation into a recipient, the method comprising ex-vivo co-culturing the stem cells with mesenchymal cells according to the methods of the present invention, and transplanting the stem cells into the recipient.

According to further features in preferred embodiments of the invention described below the stem cells are hematopoietic stem cells.

According to further features in preferred embodiments of the invention described below the transplanting the stem cells is effected together with the co-cultured mesenchymal cells.

According to further features in preferred embodiments of the invention described below the method further comprising a step of isolating the stem cells from the co-culture prior to the transplanting.

According to another aspect of the present invention there is provided a method of adoptive immunotherapy effected by obtaining hematopoietic stem cells from a patient, ex vivo expanding and inhibiting differentiation the hematopoietic cells by ex-vivo co-culturing the hematopoietic stem cells with mesenchymal cells according to the methods of any of the present invention; and transplanting said hematopoietic stem cells into a recipient.

According to yet another aspect of the present invention there is provided a method of bone marrow transplantation effected by obtaining hematopoietic stem cells from a patient, ex vivo expanding and inhibiting differentiation of the stem cells by ex-vivo co-culturing the stem cells with mesenchymal cells according to the methods of any of the present invention; and transplanting the ex-vivo expanded hematopoietic cells into a recipient.

According to yet another aspect of the present invention there is provided a method of tissue regeneration effected by obtaining stem cells from a patient; ex vivo expanding and inhibiting differentiation of the stem cells by ex-vivo co-culturing the stem cells with mesenchymal cells according to the methods of any of the present invention; and transplanting the ex-vivo expanded cells into a recipient.

According to further features in preferred embodiments of the invention described below the transplanting of hematopoietic stem cells is effected together with the co-cultured mesenchymal cells.

According to further features in preferred embodiments of the invention described below the method further comprising a step of isolating said stem cells from the co-culture prior to stem cells transplantation.

According to further features in preferred embodiments of the invention described below the stem and/or mesenchymal cells are derived from the subject.

According to further features in preferred embodiments of the invention described below the mesenchymal cells are derived from a source selected from the group consisting of endothelial cells, cardiac muscle cells, bone cells, cartilage cells, tendon cells, skeletal muscle cells, bone cells, cartilage cells, tendon cells, adipose tissue cells, neural cells, endocrine cells, hematopoietic cells, hematopoietic precursor cells, bone marrow cells, hepatocytes and hepatocyte precursor cells.

According to further features in preferred embodiments of the invention described below the mesenchymal cells are mesenchymal stem cells and/or bone marrow-derived mesenchymal cells.

According to further features in preferred embodiments of the invention described below the method further comprising providing a feeder layer of the mesenchymal cells prior to co-culturing.

According to further features in preferred embodiments of the invention described below the expanded, undifferentiated stem cells are CD34+ and/or CD133+ and/or CD34+/CD38− cells.

According to further features in preferred embodiments of the invention described below the stem cells are derived from a source selected from the group consisting of hematopoietic cells, umbilical cord blood cells, mobilized peripheral blood cells and bone marrow cells.

According to further features in preferred embodiments of the invention described below the stem cells are derived from the entire cell population or the mononuclear fraction of the bone marrow, peripheral blood or neonatal umbilical cord blood.

According to further features in preferred embodiments of the invention described below the population of stem cells is enriched for hematopoietic stem cells.

According to further features in preferred embodiments of the invention described below, the method further comprising the step of selecting a population of stem cells enriched for hematopoietic stem cells. The selecting can be effected via CD34, CD133 and CD34/CD38.

According to further features in preferred embodiments of the invention described below, the method further comprising the step of selecting a population of stem cells enriched for early hematopoietic stem/progenitor cells.

According to further features in preferred embodiments of the invention described below the method further comprising providing conditions which allow cell proliferation. Such conditions can comprise providing the cells with nutrients and cytokines.

According to further features in preferred embodiments of the invention described below the cytokines are selected from the group consisting of early acting cytokines and late acting cytokines. The early acting cytokines can be selected from the group consisting of stem cell factor, FLT3 ligand, interleukin-6, thrombopoietin and interleukin-3.

According to further features in preferred embodiments of the invention described below the early acting cytokine is FLT3 ligand.

According to further features in preferred embodiments of the invention described below the late acting cytokines are selected from the group consisting of granulocyte colony stimulating factor, granulocyte/macrophage colony stimulating factor and erythropoietin.

According to further features in preferred embodiments of the invention described below the late acting cytokine is granulocyte colony stimulating factor.

According to further features in preferred embodiments of the invention described below the stem and/or mesenchymal cells are genetically modified cells.

According to further features in preferred embodiments of the invention described below the co-culturing is effected in a two-dimensional culture or a three-dimensional culture.

According to another aspect of the present invention there is provided a therapeutic ex vivo cultured stem cell population comprising undifferentiated stem cells expanded according to the methods of the invention described below.

According to another aspect of the present invention there is provided a therapeutic ex vivo cultured stem cell population comprising mesenchymal stem cells and undifferentiated stem cells expanded according to the methods of the invention described below.

According to further features in preferred embodiments of the invention described below the cell population of the present invention is isolated from cell culture medium.

According to another aspect of the present invention there is provided a pharmaceutical composition comprising any of the cell populations of the present invention and a pharmaceutically acceptable carrier. The pharmaceutical composition may comprise an isolated or unisolated cell population The present invention successfully addresses the shortcomings of the presently known configurations by providing a method of synergistically enhancing the expansion yet at the same time inhibiting differentiation of stem cells by co-culturing with mesenchymal cells, and interference with CD38 or PI 3-kinase expression, activity, and/or PI 3-kinase signaling, and sirtuin enzymes.

The present invention further successfully addresses the shortcomings of the presently known configurations by enabling expansion of stem cells, yielding large numbers of these cell populations for transplantation into appropriate host tissues and organs for repopulation.

Additional features and advantages of the methods of cell preparations and methods of treatment according to the present invention will become apparent to the skilled artisan by reading the following descriptions.

DESCRIPTION OF THE PREFERRED EMBODIMENTS

The present invention is of methods for ex-vivo expansion of stem cells employing co-culturing of stem and mesenchymal cells, expanded populations of renewable stem cells and their use for transplantation into recipient subjects. In one embodiment, the invention facilitates the efficient establishment of large ex-vivo expanded populations of renewable hematopoietic stem cells derived from cord blood, bone marrow, peripheral blood in which differentiation was inhibited while stem and progenitor cell expansion was preferentially propagated, suitable for transplantation with or without the co-cultured mesenchymal cells. Specifically in this respect, the present invention can be used to provide ex-vivo expanded populations of stem cells, which can be used for applications in hematopoietic cell transplantations, and in generation of stem cells suitable for genetic manipulations, which may be used for cellular gene therapy. Additional applications may include, but are not limited to, adoptive immunotherapy, treatments for multiple diseases, such as, for example, implantation of stem cells for in vivo tissue and organ regeneration settings, and ex vivo tissue engineering in for tissue and organ regeneration. Additional applications may include, but are not limited to, treatments for diseases and conditions such as hematopoietic malignancies, myeloablation and in autologous or allogeneic cell therapy promoting the regeneration of any tissue or organ in need thereof. The present invention further relates to expanded stem cell preparations and to articles-of-manufacture for preparing same.

While reducing the present invention to practice, it was uncovered that co-culture of mesenchymal-derived, non-hematopoietic cells from bone marrow, along with a hematopoietic stem cell containing unselected mononuclear cell fraction, with additional of modulators of cell fate such as nicotinamide, consistently results in greatly enhanced, synergistic preferential ex-vivo proliferation and expansion without differentiation of late and early progenitor CD34+, CD34+/38+, and CD34+/lin− cell populations.

The principles and operation of the present invention may be better understood with reference to the accompanying descriptions and examples.

Before explaining at least one embodiment of the invention in detail, it is to be understood that the invention is not limited in its application to the details of construction and the arrangement of the components set forth in the following description or illustrated in the Examples section. The invention is capable of other embodiments or of being practiced or carried out in various ways. Also, it is to be understood that the phraseology and terminology employed herein is for the purpose of description and should not be regarded as limiting.

Co-culture of mesenchymal and hematopoietic cells has been previously reported. U.S. Pat. No. 6,030,836 to Thiede et al discloses the use of bone marrow mesenchymal stem cells or adipocytes in co-culture with autologous bone marrow hematopoietic stem cells, and the enhanced survival and expansion of hematopoietic progenitors such as CD34+, CD 34+/90+ and CD34+/CD14+. However, Thiede et al report that while the CD34+ hematopoietic stem cell fraction of the cultured cells is not depleted, it is significantly reduced by 21 days co-culture. Guo et al (Zhongguo Shi Yan Ye Xue Za Zhi 2000; 893-96), and Wang et al. (Haematologia, 2004; 89:837-44) reported that co-culture of mesenchymal stem cells and hematopoietic stem cells supported hematopoietic stem cell proliferation, but also reported induction of hematopoietic differentiation by 14 days in culture.

While reducing the present invention to practice, it was surprisingly found that culturing stem cells, such as hematopoietic stem cells, in the presence of cultured mesenchymal cells and modulators of cell fate results in preferential ex-vivo expansion of populations of undifferentiated hematopoietic stem cells. The proportion (from total nucleated cells) of undifferentiated CD34+ stem cells detected after 21 days co culture with mesenchymal cells increased from 0.65 to 1.5% in one case (Table 3), and from 4 to 5.3% in another (Table 4), as described in the Examples section hereinbelow. The proportion of CD34+/38− cells, and CD34+/Lin− cells in the cultures also increased significantly (up to more than a 10 fold increase with nicotinamide in some cases, see Tables 1-5 in the Examples section).

Thus, according to one aspect of the present invention there is provided a method of expanding and at the same time inhibiting differentiation of a population of stem cells, the method comprising ex-vivo co-culturing the stem cells with mesenchymal cells under conditions which allow expanding and at the same time inhibiting differentiation of at least a portion of the stem cells, wherein said conditions are selected from the group consisting of: (i) conditions reducing expression and/or activity of CD38 in the cells; (ii) conditions reducing capacity of the cells in responding to signaling pathways involving CD38 in the cells; (iii) conditions reducing capacity of the cells in responding to retinoic acid, retinoids and/or Vitamin D in the cells; (iv) conditions reducing capacity of the cells in responding to signaling pathways involving the retinoic acid receptor, the retinoid X receptor and/or the Vitamin D receptor in the cells; (v) conditions reducing capacity of the cells in responding to signaling pathways involving PI 3-kinase; (vi) conditions wherein the cells are cultured in the presence of nicotinamide, a nicotinamide analog, a nicotinamide or a nicotinamide analog derivative or a nicotinamide or a nicotinamide analog metabolite; (vii) conditions wherein the cells are cultured in the presence of a copper chelator; (viii) conditions wherein the cells are cultured in the presence of a copper chelate; (ix) conditions wherein the cells are cultured in the presence of a PI 3-kinase inhibitor; and (x) conditions wherein the cells are cultured in the presence of an inhibitor of sirtuin enzymes.

As used herein, the phrase "stem cells" refers both to the earliest renewable cell population responsible for generating cell mass in a tissue or body and the very early progenitor cells, which are somewhat more differentiated, yet are not committed and can readily revert to become a part of the earliest renewable cell population. Methods of ex-vivo culturing stem cells are well known in the art of cell culturing. To this effect, see for example, the text book "Culture of Animal Cells—A Manual of Basic Technique" by Freshney, Wiley-Liss, N.Y. (1994), Third Edition, the teachings of which are hereby incorporated by reference.

In a preferred embodiment, the source of the stem cell population is an unfractionated mononuclear cell preparation, not having been enriched for CD34+ or other hematopoietic stem cells. In another embodiment, the stem cells are identified by stem cell markers such as CD34+, CD34+/CD38−, CD133+, CD34+/Lin−, and other stem cell markers known in the art. In yet another embodiment, the source of the stem cell population for co-culture with mesenchymal cells are stem cells having been enriched for hematopoietic stem cells by selection according to stem cell markers. In yet a further embodiment, the source of the stem cell population for co-culture with mesenchymal cells is an expanded, undifferentiated stem cell population, following short- or long-term expansion according to the methods described hereinbelow.

Mesenchymal cells originate from the mesodermal layer of embryonic cells during development, and are present in every organ including subcutaneous tissue, lungs, liver, and mesenchymal tissue such as bone, cartilage, fat, tendon, skeletal muscle and the stroma of bone marrow. Mesenchymal cells are capable of differentiating in a given direction and are capable of expanding. Under normal conditions, mesenchymal cells stay at phase G0, but can shift to phase G1 (initiation of division) when stimulated. Examples of mesenchymal cells include stromal cells and cells having the properties of stromal cells. As used herein, the phrase "mesenchymal cells" refers to cells derived from the mesodermal layer and capable of differentiation. Mesodermal cells can also be characterized, and isolated, by a number of prospective markers: presently, the presence of CD 73 and/or CD105 and/or CD166, CD49b, SH(1), SH(2), SH(3), or SH(4) surface antigens, the absence of CD34+, CD14+, CD45+, and HLA class 1, as well as superior adherence to plastic and multipotent differentiation potential, help to identify cells of mesenchymal lineage from various tissue sources (see Horowitz, Cytotherapy 2000, 2:387-88, and Lee et al, BBRC 2004; 320:273-78, and US Patent Application Nos. 20020058289 and 20040058397 to Thomas, et al).

Examples of cells derived from mesenchymal cells include (1) cells of the cardiovascular system such as endothelial cells or cardiac muscle cells or the precursor cells of the cells of the cardiovascular system, and cells having the properties of these cells; (2) cells of any one of bone, cartilage, tendon and skeletal muscle, the precursor cells of the cells of any one of bone, cartilage, tendon, skeletal muscle and adipose tissue, and the cells having the properties of these cells; (3) neural cells or the precursor cells of neural cells, and the cells having the properties of these cells; (4) endocrine cells or the precursor cells of endocrine cells, and the cells having the properties of these cells; (5) hematopoietic cells or the precursor cells of hematopoietic cells, and the cells having the properties of these cells; and (6) hepatocytes or the precursor cells of hepatocytes, and the cells having the properties of these cells. Methods of mesenchymal cell culture are well known in the art of cell culturing (see, for example, Friedenstein, et al, Exp Hematol 1976 4, 267-74; Dexter et al. J Cell Physiol 1977, 91:335-44; and Greenberger, Nature 1978 275, 7524). Thus, according to one embodiment of the present invention, mesenchymal cells are derived from a source selected from the group consisting of endothelial cells, cardiac muscle cells, bone cells, cartilage cells, tendon cells, skeletal muscle cells, bone cells, cartilage cells, tendon cells, adipose tissue cells, neural cells, endocrine cells, hematopoietic cells, hematopoietic precursor cells, bone marrow cells, and the precursor cells thereof, hepatocytes, and hepatocyte precursor cells.

Cell culture methods are described generally in the current edition of Culture of Animal Cells: A Manual of Basic Technique (R. I. Freshney ed., Wiley & Sons); General Techniques of Cell Culture (M. A. Harrison & I. F. Rae, Cambridge Univ. Press), and Embryonic Stem Cells: Methods and Protocols (K. Turksen ed., Humana Press). Other texts are Creating a High Performance Culture (Aroselli, Hu. Res. Dev. Pr. 1996) and Limits to Growth (D. H. Meadows et al., Universe Publ. 1974). Tissue culture supplies and reagents are available from commercial vendors such as Gibco/BRL, Nalgene-Nunc International, Sigma Chemical Co., and ICN Biomedicals.

It will be appreciated, in the context of the present invention, that the cell culture can be a two dimensional cell culture system, or a three dimensional cell culture system. Two-dimensional cell culture systems are defined as cultures in which cells are grown as confluent monolayers which make the surface suitable for attachment of other cells, such as feeder layers. For example, the growth of glioma on confluent feeder layers of normal fetal intestine has been reported. While the growth of cells in two dimensions is a convenient method for preparing, observing and studying cells in culture, allowing a high rate of cell proliferation, it lacks the cell-cell and cell-matrix interactions characteristic of whole tissue in vivo. Investigators have explored the use of three-dimensional substrates such as collagen gel (Douglas et al., 1980, In Vitro 16:306-312; Yang et al., 1979, Proc. Natl. Acad. Sci. 76:3401; Yang et al., 1980, Proc. Natl. Acad. Sci. 77:2088-2092; Yang et al., 1981, Cancer Res. 41:1021-1027); cellulose sponge, alone (Leighton et al., 1951, J. Natl. Cancer Inst. 12:545-561) or collagen coated (Leighton et al., 1968, Cancer Res. 28:286-296); a gelatin sponge, Gelfoam (Sorour et al., 1975, J. Neurosurg. 43:742-749). Three dimensional cell culture systems are systems which allow the cells to grow in multiple layers, thus creating a three-dimensional cell culture system which may overcome the limitations of contact inhibition found in two-dimensional systems. Three dimensional culture systems are usually characterized by provision of a support or matrix for growth of cells, as detailed hereinabove. Many cell types and tissues can be grown in the three-dimensional culture system. Methods for growth of cells in such three dimensional cultures are described in detail in the art, for example, U.S. Pat. Nos. 5,160,490, 5,032,508, 5,785,964 and 5,858,721, all to Naughton, et al.

Co-culturing of stem cells with mesenchymal cells can be initiated at different times in the culture process. Mesenchymal cells may be added to an existing stem cell culture, stem cells may be added to an existing mesenchymal cell culture, or the cells may be mixed and cultured simultaneously. In a preferred embodiment, the mesenchymal cells are cultured to confluence, replated and recultured to provide a feeder layer, to which is added the hematopoietic stem cell population, for co-culturing under conditions allowing expansion and at the same time inhibit differentiation of the stem cells.

As used herein the term "inhibiting" refers to slowing, decreasing, delaying, preventing or abolishing.

As used herein the term "differentiation" refers to relatively generalized or specialized changes during development. Cell differentiation of various lineages is a well-documented process and requires no further description herein. As used herein the term differentiation is distinct from maturation which is a process, although some times associated with cell division, in which a specific cell type mature to function and then dies, e.g., via programmed cell death.

The phrase "cell expansion" is used herein to describe a process of cell proliferation substantially devoid of cell differentiation. Cells that undergo expansion hence maintain their cell renewal properties and are oftentimes referred to herein as renewable cells, e.g., renewable stem cells.

As used herein the term "ex-vivo" refers to a process in which cells are removed from a living organism and are propagated outside the organism (e.g., in a test tube). As used herein, the term "ex-vivo", however, does not refer to a process by which cells known to propagate only in-vitro, such as various cell lines (e.g., HL-60, MEL, HeLa, etc.) are cultured. In other words, cells expanded ex-vivo according to the present invention do not transform into cell lines in that they eventually undergo differentiation.

Providing the ex-vivo grown cells with conditions for ex-vivo cell proliferation include providing the cells with nutrients and preferably with one or more cytokines, as is further detailed hereinunder.

While reducing the present invention to practice, it has been shown that the methods of the present invention allow proliferation of cells in culture, while preferentially expanding the stem cell population, and inhibiting differentiation thereof.

Ex-vivo expansion of the stem and/or progenitor cells, under conditions allowing expanding and inhibiting differentiation, has been described. PCT IL03/00064 to Peled et al, which is incorporated by reference as if fully set forth herein, teaches methods of reducing expression and/or activity of CD38 in cells, methods of reducing capacity of cells in responding to signaling pathways involving CD38 in the cells, methods of reducing capacity of cells in responding to retinoic acid, retinoids and/or Vitamin D in the cells, methods of reducing the capacity of cells in responding to signaling pathways involving the retinoic acid receptor, the retinoid X receptor and/or the Vitamin D receptor in the cells, methods of reducing the capacity of cells in responding to signaling pathways involving PI 3-kinase, conditions wherein cells are cultured in the presence of nicotinamide, a nicotinamide analog, a nicotinamide or a nicotinamide analog derivative or a nicotinamide or a nicotinamide analog metabolite, conditions wherein cells are cultured in the presence of a PI 3-kinase inhibitor and conditions wherein cells are cultured in the presence of an inhibitor of sirtuin enzymes.

In one embodiment of the invention, reducing the activity of CD38 is effected by providing the cells with an agent that inhibits CD38 activity (i.e., a CD38 inhibitor).

As used herein a "CD38 inhibitor" refers to an agent which is capable of down-regulating or suppressing CD38 activity in stem cells.

A CD38 inhibitor according to this aspect of the present invention can be a "direct inhibitor" which inhibits CD38 intrinsic activity or an "indirect inhibitor" which inhibits the activity or expression of CD38 signaling components (e.g., the cADPR and ryanodine signaling pathways) or other signaling pathways which are effected by CD38 activity.

According to presently known embodiments of this aspect of the present invention, nicotinamide is a preferred CD38 inhibitor.

Hence, in one embodiment, the method according to this aspect of the present invention is effected by providing the cells either with nicotinamide itself, or with a nicotinamide analog, a nicotinamide or a nicotinamide analog derivative or a nicotinamide or a nicotinamide analog metabolite.

As used herein, the phrase "nicotinamide analog" refers to any molecule that is known to act similarly to nicotinamide. Representative examples of nicotinamide analogs include, without limitation, benzamide, nicotinethioamide (the thiol analog of nicotinamide), nicotinic acid and α-amino-3-indolepropionic acid.

The phrase "a nicotinamide or a nicotinamide analog derivative" refers to any structural derivative of nicotinamide itself or of an analog of nicotinamide. Examples of such derivatives include, without limitation, substituted benzamides, substituted nicotinamides and nicotinethioamides and N-substituted nicotinamides and nicotinthioamides.

The phrase "a nicotinamide or a nicotinamide analog metabolite" refers to products that are derived from nicotinamide or from analogs thereof such as, for example, NAD, NADH and NADPH.

Alternatively, a CD38 inhibitor according to this aspect of the present invention can be an activity neutralizing antibody which binds for example to the CD38 catalytic domain, thereby inhibiting CD38 catalytic activity. It will be appreciated, though, that since CD38 is an intracellular protein measures are taken to use inhibitors which may be delivered through the plasma membrane. In this respect a fragmented antibody such as a Fab fragment (described hereinunder) is preferably used.

The term "antibody" as used in this invention includes intact molecules as well as functional fragments thereof, such as Fab, F(ab')$_2$, and Fv that are capable of binding to macrophages. These functional antibody fragments are defined as follows:

Fab, the fragment which contains a monovalent antigen-binding fragment of an antibody molecule, can be produced by digestion of whole antibody with the enzyme papain to yield an intact light chain and a portion of one heavy chain;

Fab', the fragment of an antibody molecule that can be obtained by treating whole antibody with pepsin, followed by reduction, to yield an intact light chain and a portion of the heavy chain; two Fab' fragments are obtained per antibody molecule;

(Fab')$_2$, the fragment of the antibody that can be obtained by treating whole antibody with the enzyme pepsin without subsequent reduction; F(ab')$_2$ is a dimer of two Fab' fragments held together by two disulfide bonds;

Fv, defined as a genetically engineered fragment containing the variable region of the light chain and the variable region of the heavy chain expressed as two chains; and Single chain antibody ("SCA"), a genetically engineered molecule containing the variable region of the light chain and the variable region of the heavy chain, linked by a suitable polypeptide linker as a genetically fused single chain molecule.

Methods of making these fragments are known in the art. (See for example, Harlow and Lane, Antibodies: A Laboratory Manual, Cold Spring Harbor Laboratory, New York, 1988, incorporated herein by reference).

Antibody fragments according to the present invention can be prepared by expression in E. coli or mammalian cells (e.g. Chinese hamster ovary cell culture or other protein expression systems) of DNA encoding the fragment.

Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R., Biochem. J., 73: 119-126, 1959. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of $V_H$ and $V_L$ chains. This association may be noncovalent, as described in Inbar et al., Proc. Nat'l Acad. Sci. USA 69:2659-62, 1972. Alternatively, the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are described, for example, by Whitlow and Filpula, Methods, 2: 97-105, 1991; Bird et al., Science 242:423-426, 1988; Pack et al., Bio/Technology 11:1271-77, 1993; and Ladner et al., U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry, Methods, 2: 106-10, 1991.

Humanized forms of non-human (e.g., murine) antibodies are chimeric molecules of immunoglobulins, immunoglobulin chains or fragments thereof (such as Fv, Fab, Fab', $F(ab')_2$ or other antigen-binding subsequences of antibodies) which contain minimal sequence derived from non-human immunoglobulin. Humanized antibodies include human immunoglobulins recipient antibody in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321: 522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

Human antibodies can also be produced using various techniques known in the art, including phage display libraries (Hoogenboom and Winter, J. Mol. Biol., 227:381 (1991); Marks et al., J. Mol. Biol., 222:581 (1991)). The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1):86-95 (1991)]. Similarly, human can be made by introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10, 779-783 (1992); Lonberg et al., Nature 368 856-859 (1994); Morrison, Nature 368 812-13 (1994); Fishwild et al., Nature Biotechnology 14, 845-51 (1996); Neuberger, Nature Biotechnology 14, 826 (1996); Lonberg and Huszar, Intern. Rev. Immunol. 13 65-93 (1995).

Alternatively, the method according to this aspect of the present invention can be effected by providing the ex-vivo cultured stem cells with an agent that down-regulates CD38 expression.

An agent that downregulates CD38 expression refers to any agent which affects CD38 synthesis (decelerates) or degradation (accelerates) either at the level of the mRNA or at the level of the protein. For example, a small interfering polynucleotide molecule which is designed to down regulate the expression of CD38 can be used according to this aspect of the present invention.

An example for a small interfering polynucleotide molecule which can down-regulate the expression of CD38 is a small interfering RNA or siRNA, such as, for example, the morpholino antisense oligonucleotides described by in Munshi et al. (Munshi C B, Graeff R, Lee H C, J Biol Chem 2002 Dec. 20; 277(51):49453-8), which includes duplex oligonucleotides which direct sequence specific degradation of mRNA through the previously described mechanism of RNA interference (RNAi) (Hutvagner and Zamore (2002) Curr. Opin. Genetics and Development 12:225-232).

As used herein, the phrase "duplex oligonucleotide" refers to an oligonucleotide structure or mimetics thereof, which is formed by either a single self-complementary nucleic acid strand or by at least two complementary nucleic acid strands. The "duplex oligonucleotide" of the present invention can be composed of double-stranded RNA (dsRNA), a DNA-RNA hybrid, single-stranded RNA (ssRNA), isolated RNA (i.e., partially purified RNA, essentially pure RNA), synthetic RNA and recombinantly produced RNA.

Preferably, the specific small interfering duplex oligonucleotide of the present invention is an oligoribonucleotide composed mainly of ribonucleic acids.

Instructions for generation of duplex oligonucleotides capable of mediating RNA interference are provided in www.ambion.com.

Hence, the small interfering polynucleotide molecule according to the present invention can be an RNAi molecule (RNA interference molecule).

Alternatively, a small interfering polynucleotide molecule can be an oligonucleotide such as a CD38-specific antisense molecule or a rybozyme molecule, further described hereinunder.

Oligonucleotides designed according to the teachings of the present invention can be generated according to any oligonucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the oligonucleotides is well within the capabilities of one skilled in the art.

Oligonucleotides used according to this embodiment of the present invention are those having a length selected from a range of 10 to about 200 bases preferably 15-150 bases, more preferably 20-100 bases, most preferably 20-50 bases.

The oligonucleotides of the present invention may comprise heterocyclic nucleosides consisting of purines and the pyrimidines bases, bonded in a 3' to 5' phosphodiester linkage.

Preferably used oligonucleotides are those modified in either backbone, internucleoside linkages or bases, as is broadly described hereinunder. Such modifications can oftentimes facilitate oligonucleotide uptake and resistivity to intracellular conditions.

Specific examples of preferred oligonucleotides useful according to this aspect of the present invention include oligonucleotides containing modified backbones or non-natural internucleoside linkages. Oligonucleotides having modified backbones include those that retain a phosphorus atom in the backbone, as disclosed in U.S. Pat. Nos. 4,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides which can be used according to the present invention, are those modified in both sugar and the internucleoside linkage, i.e., the backbone, of the nucleotide units are replaced with novel groups. The base units are maintained for complementation with the appropriate polynucleotide target. An example for such an oligonucleotide mimetic, includes peptide nucleic acid (PNA). A PNA oligonucleotide refers to an oligonucleotide where the sugar-backbone is replaced with an amide containing backbone, in particular an aminoethylglycine backbone. The bases are retained and are bound directly or indirectly to aza nitrogen atoms of the amide portion of the backbone. United States patents that teach the preparation of PNA compounds include, but are not limited to, U.S. Pat. Nos. 5,539,082; 5,714,331; and 5,719,262, each of which is herein incorporated by reference. Other backbone modifications, which can be used in the present invention are disclosed in U.S. Pat. No. 6,303,374.

Oligonucleotides of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Such bases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. [Sanghvi Y S et al. (1993) Antisense Research and Applications, CRC Press, Boca Raton 276-278] and are presently preferred base substitutions, even more particularly when combined with 2'-O-methoxyethyl sugar modifications.

Another modification of the oligonucleotides of the invention involves chemically linking to the oligonucleotide one or more moieties or conjugates, which enhance the activity, cellular distribution or cellular uptake of the oligonucleotide. Such moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., dihexadecyl-rac-glycerol or triethylammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety, as disclosed in U.S. Pat. No. 6,303,374.

It is not necessary for all positions in a given oligonucleotide molecule to be uniformly modified, and in fact more than one of the aforementioned modifications may be incorporated in a single compound or even at a single nucleoside within an oligonucleotide.

As described hereinabove, the oligonucleotides of the present invention are preferably antisense molecules, which are chimeric molecules. "Chimeric antisense molecules" are oligonucleotides, which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target polynucleotide. An additional region of the oligonucleotide may serve as a substrate for enzymes capable of cleaving RNA:DNA or RNA:RNA hybrids. An example for such includes RNase H, which is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense molecules of the present invention may be formed as composite structures of two or more oligonucleotides, modified oligonucleotides, as described above. Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, each of which is herein fully incorporated by reference.

The oligonucleotides of the present invention can further comprise a ribozyme sequence. Ribozymes are being increasingly used for the sequence-specific inhibition of gene expression by the cleavage of mRNAs. Several rybozyme sequences can be fused to the oligonucleotides of the present invention. These sequences include but are not limited to ANGIOZYME specifically inhibiting formation of the VEGF-R (Vascular Endothelial Growth Factor receptor), a key component in the angiogenesis pathway, and HEPTAZYME, a rybozyme designed to selectively destroy Hepatitis C Virus (HCV) RNA, (Rybozyme Pharmaceuticals, Incorporated—WEB home page).

Further alternatively, a small interfering polynucleotide molecule, according to the present invention can be a DNAzyme.

DNAzymes are single-stranded catalytic nucleic acid molecules A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M Curr Opin Mol Ther 2002; 4:119-21).

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther www.asgt.org). In another application, DNAzymes complementary to bcr-ab1 oncogenes were successful in inhibiting the oncogenes expression in leukemia cells, and lessening relapse rates in autologous bone marrow transplant in cases of CML and ALL.

Alternatively, as described hereinabove, retinoid receptor superfamily inhibitors (e.g., antagonists, siRNA molecules, antisense molecules, antibodies, etc.) which downregulate or suppress retinoid receptor activity and/or expression can be used to down regulate CD38 expression.

Briefly, retinoid receptors such as RAR, RXR and VDR have been reported to be involved in the regulation of gene expression pathways associated with cell proliferation and differentiation and in particular in the regulation of CD38 expression. Hence, preferred agents that downregulate CD38 expression according to the present invention include RAR antagonists, RXR antagonists and VDR antagonists or, alternatively, antagonists for reducing the capacity of the stem cells in responding to retinoic acid, retinoid and/or Vitamin D.

As used herein the term "antagonist" refers to an agent that counteracts or abrogates the effects of an agonist or a natural ligand of a receptor. Further features relating to such antagonists are detailed hereinunder.

In one preferred embodiment, reducing the capacity of the stem cells in responding to the above antagonists and/or signaling pathways of the above receptors and kinase is by ex-vivo culturing the stem cells in a presence of an effective amount of at least one retinoic acid receptor antagonist, at least one retinoid X receptor antagonist and/or at least one Vitamin D receptor antagonist, preferably, for a time period of 0.1-50%, preferably, 0.1-25%, more preferably, 0.1-15%, of an entire ex-vivo culturing period of the stem cells or for the entire period. In this respect it was surprisingly uncovered that an initial pulse exposure to an antagonist is sufficient to exert cell expansion long after the antagonist was removed from the culturing set up.

Many antagonists to RAR, RXR and VDR are presently known, some of which are listed hereinafter.

The retinoic acid receptor antagonist used in context of the different aspects and embodiments of the present invention can be:
AGN 194310; AGN 109; 3-4-Methoxy-phenylsulfanyl)-3-methyl-butyric acid; 6-Methoxy-2,2-dimethyl-thiochroman-4-one,2,2-Dimethyl-4-oxo-thiochroman-6-yltrifluoromethane-sulfonate; Ethyl 4-((2,2 dimethyl-4-oxo-thiochroman-6-yl)ethynyl)-benzoate; Ethyl 4-((2,2-dimethy 1-4-triflouromethanensulfonyloxy-(2H)-thiochromen-6-yl) ethynyl)-benzoate(41); Thiochromen-6-yl]-ethynyl]-benzoate(yl); (p-[(E)-2-[3'4'-Dihydro-4,4'-dimethyl-7'-(heptyloxy)-2'H-1-benzothiopyran-6'yl]propenyl]benzoic acid 1'1'-dioxide; 2E,4E,6E-[7-(3,5-Di-t-butyl-4-n-butoxyphenyl)-3-methyl]-octa-2,4,6-trienoic acid; 2E,4E,6E-[7-(3,5-Di-t-butyl-4-n-propoxyphenyl)-3-methyl]-octa-2,4,6-trienoic acid; 2E,4E,6E-[7-(3,5-Di-t-butyl-4-n-pentoxyphenyl)-3-methyl]-octa-2,4,6-trienoic acid; 2E,4E,6E-[7-(3,5-Di-t-butyl-4-n-hexoxyphenyl)-3-methyl]-octa-2,4,6-trienoic acid;

2E,4E,6E-[7-(3,5-Di-t-butyl-4-n-heptoxyphenyl)-3-methyl]-octa-2,4,6-trienoic acid; 2E,4E,6E-[7-(3,5-Di-t-butyl-4-n-octoxyphenyl)-3-methyl]-octa-2,4,6-trienoic acid; (2E, 4E,6E)-7-[3-t-butyl-5-(1-phenyl-vinyl)-phenyl]-3-methyl-octa-2,4,6-trienoic acid; 2E,4E,6E-[7-(3,5-Di-t-butyl-4-{[4, 5-.sup.3H.sub.2]-n-pentoxy}phenyl)-3-methyl]-octa-2,4,6-trienoic acid; (2E,4E)-(1RS,2RS)-5-[2-(3,5-di-tert.butyl-2-ethoxy-phenyl)-cyclopropyl]-3-methyl-penta-2,4-dienoic acid ethyl ester; (2E,4E)-(1RS,2RS)-5-[2-(3,5-di-tert.butyl-2-ethoxy-phenyl)-cyclopropyl]-3-methyl-penta-2,4-dienoic acid; (2E,4E)-(1RS,2RS)-5-[2-(3,5-di-tert.butyl-2-butoxy-phenyl)-cyclopropyl]-3-methyl-penta-2,4-dienoic acid; (2E, 4E,6Z)-7-[3,5-di-tert.butyl-2-ethoxyphenyl]3-methyl-2,4,6-octatrienoic acid; (2E,4E,6Z)-7-[3,5-di-tert.butyl-2-butyloxyphenyl]-3-methyl-2,4,6-octatrienoic acid; 4-(5,6,7,8-tetrahydro-5,5,8,8-tetramethyl-2-naphthalene-carboxamido) benzoic acid; (2E,4E)-3-methyl-5-[(1S,2S)-2-(5,5,8,8-tetramethyl-5,6,7,8-tetrahydro-naphthalen-2-yl)-cyclopropyl]-penta-2,4-dienoic acid; p-[(E)-2-[3',4'-Dihydro-4',4'-dimethyl-7'-(heptyloxy)-2'H-1-benzothiopyran-6'-yl]propenyl]benzoic acid; 1',1'-dioxide, 4-(7,7,10,10-Tetramethyl-1-pyridin-3-ylmethyl-4,5,7,8,9,10-hexahydro-1H-naphto[2,3-g]indol-3-yl)-benzoic acid; (2E,4E,6Z)-7-[3,5-di-tert.butyl-2-methoxyphenyl]-3-methyl-2,4,6-octatrienoic acid; (2E,4E,6Z)-7-[3,5-di-tert.butyl-2-ethoxyphenyl]-3-methyl-2,4,6-octatrienoic acid; (2E,4E,6Z)-7-[3,5-di-tert.butyl-2-hexyloxyphenyl]-3-methyl-2,4,6-octatrienoic acid; (2E,4E,6Z)-7-[3,5-di-tert.butyl-2-octyloxyphenyl]-3-methyl-2,4,6-octatrienoic acid; and (2E, 4E)-(1RS,2RS)-5-[2-(3,5-di-tert-butyl-2-butoxy-phenyl)-cyclopropyl]-3-methyl-penta-2,4-dienoic acid (2E,4E,6Z)-7-(3-n-propoxy-5,6,7,8-tetrahydro-5,5,8,8-tetramethylnaphthalene-2-yl)-3-methylocta-2,4,6-trienoic acid, and 4-(5H-2,3(2,5 dimethyl-2,5-hexano)-5-n-propyldibenzo[b,e][1,4]diazepin-11-yl)benzoic acid, and 4-(5H-2,3-(2,5-dimethyl-2,5-hexano)-5methyl-8-nitrodibenzo[b,e][1,4]diazepin-11-yl)benzoic acid, and 4-{[4-(4-Ethylphenyl)2,2-dimethyl-(2H)-thiochromen-6-yl]ethynyl}benzoic acid, and 4-[4-2methyl-1,2-dicarba-closo-dodecaboran-1-yl-phenylcarbamoyl]benzoic acid, and 4-[4,5,7,8,9,10-hexahydro-7,7,10,10-tetramethyl-1-(3-pyridylmethyl)-anthra[1,2-b]pyrrol-3-yl]benzoic acid, and (3-pyridylmethyl)-]5-thiaanthra[2,1-b]pyrrol-3-yl)benzoic acid, and (3-pyridylmethyl)-anthra[2m1-d]pyrazol-3-yl]benzoic acid.

The retinoid X receptor antagonist used in context of the different aspects and embodiments of the present invention can be: LGN100572, 1-(3-hydroxy-5,6,78-tetrahydro-5,5,8,8-tetramethylnaphthalene-2-yl)ethanone, 1-(3-propoxy-5,6,7,8-tetrahydro-5,5,8,8-tetramethylnaphthalene-2-yl)ethanone, 3-(3-propoxy-5,6,7,8-tetrahydro-5,5,8,8-tetramethylnaphthalene-2-yl)but-2-enenitrile, 3-(3-propoxy-5,6,7,8-tetrahydro-5,5,8,8-tetramethylnaphthalene-2-yl)but-2-enal, (2E,4E,6E)-7-3[-propoxy-5,6,7,8-tetrahydro 5,5,8,8-tetramethyl-2-naphthalene-yl]-3-methylocta-2,4,6-trienoic acid, 4-[3,5,5,8,8-pentamethyl-5,6,7,8-tetrahydro-2-naphthyl)carbonyl]benzoic acid, 4-[1-(3,5,5,8,8-pentamethyl-5,6,7,8-tetrahydro-2-naphthyl)ethenyl]benzoic acid, 4-[1(3,5,5,8,8-pentamethyl-5,6,7,8-tetrahydro-2-naphthyl)cyclopropyl]benzoic acid, 4-[1-(3,5,5,8,8-pentamethyl-5,6,7,8-tetrahydro-2-naphthyl)ethenyl]benzenetetrazole, 2-[1-(5,5,8,8-tetramethyl-5,6,7,8-tetrahydro-2-naphthyl)ethenyl]pyridine-5-carboxylic acid, 2-[1-(3,5,5,8,8-pentamethyl-5,6,7,8-tetrahydro-2-naphthyl)ethyl]pyridine-5-carboxylic acid, ethyl-2-[1-(3,5,5,8,8-pentamethyl-5,6,7,8-tetrahydro-2-naphthyl)ethenyl]pyridine-5-carboxylate, 5-[1-3,5,5,8,8-pentamethyl-5,6,7,8-tetrahydro-2-naphthyl)ethenyl]pyridine-2-carboxylic acid, 2-[1-(3,5,5,8,8-pentamethyl-5,6,7,8-tetrahydro-2-naphthyl)cyclopropyl]pyridine-5-carboxylic acid, methyl 2-[1-(3,5,5,8,8-pentamethyl-5,6,7,8-tetrahydro-2-naphthyl)cyclopropyl]pyridine-5-carboxylate, 4-[1-(3,5,5,8,8-pentamethyl-5,6,7,8-tetrahydro-2-naphthyl)ethenyl]-N-(4-hydroxyphenyl) benzamide, 2-[1-(3,5,5,8,8-Pentamethyl-5,6,7,8-tetrahydro-2-naphthyl)ethenyl]pyridine-5-carboxylic acid, 2-[1-(3,5,5,8,8-Pentamethyl-5,6,7,8-tetrahydro-2-naphthyl) cyclopropyl]pyridine-5-carboxylic acid, 4-[(3,5,5,8,8-pentamethyl-5,6,7,8-tetrahydro-2-naphthyl)carbonyl] benzoic acid butyloxime, 4-[(3,5,5,8,8-pentamethyl-5,6,7,8-tetrahydro-2-naphthyl) carbonyl]benzoic acid propyloxime, 4-[(3,5,5,8,8-pentamethyl-5,6,7,8-terrahydro-2-naphthyl) carbonyl]benzoic acid cyanoimine, 4-[(3,5,5,8,8-pentamethyl-5,6,7,8-tetrahydro-2-naphthyl)carbonyl]benzoic acid allyloxime, 4-[(3,5,5,8,8-pentamethyl-5,6,7,8-tetrahydro-2-naphthyl)carbonyl]benzoic acid 4-(3-methylbut-2-enoic acid)oxime, and 4-[(3,5,5,8,8-pentamethyl-5,6,7,8-tetrahydro-2-naphthyl)carbonyl]benzoic acid 1-aminoethyloxime(2E, 4E,6Z)-7-(3-n-propoxy-5,6,7,8-tetrahydro-5,5,8,8-tetramethylnaphthalene-2-yl)-3-methylocta-2,4,6-trienoic acid, and 4-(5H-2,3(2,5 dimethyl-2,5-hexano)-5-n-propyldibenzo[b,e][1,4]diazepin-11-yl)benzoic acid, and 4-(5H-2,3-(2,5-dimethyl-2,5-hexano)-5m.

The Vitamin D receptor antagonist used in context of the different aspects and embodiments of the present invention can be: 1 alpha, 25-(OH)-D3-26,23 lactone; 1alpha, 25-dihydroxyvitamin D (3); the 25-carboxylic ester ZK159222; (23S)-25-dehydro-1 alpha-OH-D (3); (23R)-25-dehydro-1 alpha-OH-D (3); 1 beta, 25 (OH)$_2$D$_3$; 1 beta, 25(OH)$_2$-3-epi-D$_3$; (23S) 25-dehydro-1 alpha(OH) D3-26,23-lactone; (23R) 25-dehydro-1 alpha(OH)D3-26,23-lactone and Butyl-(5Z, 7E,22E-(1S,7E,22E-(1S,3R,24R)-1,3,24-trihydroxy-26,27-cyclo-9,10-secocholesta-5,7,10(19),22-tetraene-25-carboxylate).

The above listed antagonists are known for their high affinity towards their respective cognate receptors. However, it may be possible for these molecules to be active towards other receptors.

Each of the agents described hereinabove may reduce the expression or activity of CD38 individually. However, the present invention aims to also encompass the use of any subcombination of these agents.

It will be appreciated that protein agents (e.g., antibodies) of the present invention can be expressed from a polynucleotide encoding same and provided to ex-vivo cultured stem cells employing an appropriate gene delivery vehicle/method and a nucleic acid construct as is further described hereinunder.

Examples of suitable constructs include, but are not limited to pcDNA3, pcDNA3.1 (+/−), pGL3, PzeoSV2 (+/−), pDisplay, pEF/myc/cyto, pCMV/myc/cyto each of which is commercially available from Invitrogen Co. (www.invitrogen.com). Examples of retroviral vector and packaging systems are those sold by Clontech, San Diego, Calif., including Retro-X vectors pLNCX and pLXSN, which permit cloning into multiple cloning sites and the transgene is transcribed from CMV promoter. Vectors derived from Mo-MuLV are also included such as pBabe, where the transgene will be transcribed from the 5'LTR promoter.

As the method of ex-vivo expanding and inhibiting differentiation of a population of stem cells, while at the same time inhibiting the differentiation of the stem cells is effected by co-culturing with mesenchymal cells under conditions modulating CD38 expression and/or activity, either at the protein level, using RAR, RXR or VDR antagonists or a CD38 inhibitor such as nicotinamide and analogs thereof, or at the at the expression level via genetic engineering techniques, as is detailed hereinabove, there are further provided, according to the present invention, several preferred methods of ex-vivo expanding a population of stem cells, while at the same time, inhibiting differentiation of the stem cells ex-vivo.

Still alternatively, according to the present invention, as described hereinabove, inhibitors of activity or expression of PI 3-kinase are used to down regulate CD38 expression.

Thus, in still another particular embodiment of this aspect of the present invention, culturing the stem cells ex-vivo with mesenchymal cells under conditions allowing expanding and at the same time inhibiting differentiation is effected by culturing the cells in conditions reducing the capacity of the cells in responding to signaling pathways involving PI 3-kinase, or in conditions wherein the cells are cultured in the presence of the PI 3-kinase inhibitors.

All the methodologies described herein with respect to the inhibition of expression apply also to inhibition of expression of PI 3-kinase and sirtuin enzymes. These methodologies include, for example, the use of polynucleotides, such as small interfering RNA molecules, antisense ribozymes and DNAzymes, as well as intracellular antibodies.

Inhibition of PI 3-kinase activity can be effected by known PI 3-kinase inhibitors, such as wortmannin and LY294002 and the inhibitors described in, for example, U.S. Pat. No. 5,378,725, which is incorporated herein by reference. In one particular embodiment, the ex-vivo expanding and inhibiting differentiation of a population of stem cells is effected by co-culturing with mesenchymal cells and providing the stem cells with ex-vivo culture conditions for reducing a capacity of the stem cells in responding to retinoic acid, retinoids and/or Vitamin D, thereby expanding the population of stem cells while at the same time, inhibiting differentiation of the stem cells ex-vivo. In still another particular embodiment of this aspect of the present invention, the ex-vivo expanding and at the same time inhibiting differentiation of a population of stem cells, is effected by obtaining adult or neonatal umbilical cord whole white blood cells or whole bone marrow cells sample, co-culturing with mesenchymal cells, and providing the cells in the sample with ex-vivo culture conditions for stem cells ex-vivo cell proliferation and with a PI 3-kinase inhibitor, thereby expanding and at the same time inhibiting differentiation of a population of a renewable stem cells in the sample.

In one preferred embodiment, concomitant with treating the cells with conditions which allow for ex-vivo the stem cells to proliferate, the cells are short-term treated or long-term treated to reduce the expression and/or activity of PI 3-kinase.

In one embodiment of the invention, reducing the activity of PI 3-kinase is effected by providing the cells with an modulator of PI 3-kinase that inhibits PI 3-kinase catalytic activity (i.e., a PI 3-kinase inhibitor).

As used herein a "modulator capable of downregulating PI 3-kinase activity or gene expression" refers to an agent which is capable of down-regulating or suppressing PI 3-kinase activity in stem cells.

An inhibitor of PI 3-kinase activity according to this aspect of the present invention can be a "direct inhibitor" which inhibits PI 3-kinase intrinsic activity or an "indirect inhibitor" which inhibits the activity or expression of PI 3-kinase signaling components (e.g., the Akt and PDK1 signaling pathways) or other signaling pathways which are effected by PI 3-kinase activity.

According to presently known embodiments of this aspect of the present invention, wortmannin and LY294002 are preferred PI 3-kinase inhibitors.

Hence, in one embodiment, the method according to this aspect of the present invention is effected by providing known PI 3-kinase inhibitors, such as wortmannin, LY294002, and active derivatives thereof, as described in, for example, U.S. Pat. Nos. 5,378,725, 5,480,906, 5,504,103, and in International Patent Publications WO 03072557, and WO 9601108, which are incorporated herein by reference, and by the specific PI 3-kinase inhibitors disclosed in US Patent Publication 20030149074 to Melese et al., also incorporated herein by reference.

Phosphatidylinositol 3-kinase inhibitors are well known to those of skill in the art. Such inhibitors include, but are not limited to Ly294002 (Calbiochem Corp., La Jolla, Calif.) and wortmannin (Sigma Chemical Co., St. Louis Mo.) which are both potent and specific PI3K inhibitors. The chemical properties of Ly294002 are described in detail in J. Biol., Chem., (1994) 269: 5241-5248. Briefly, Ly294002, the quercetin derivative, was shown to inhibit phosphatidylinositol 3-kinase inhibitor by competing for phosphatidylinositol 3-kinase binding of ATP. At concentrations at which LY294002 fully inhibits the ATP-binding site of PI3K, it has no inhibitory effect against a number of other ATP-requiring enzymes including PI4-kinase, EGF receptor tyrosine kinase, src-like kinases, MAP kinase, protein kinase A, protein kinase C, and ATPase.

LY294002 is very stable in tissue culture medium, is membrane permeable, has no significant cytotoxicity, and at concentrations at which it inhibits members of PI3K family, it has no effect on other signaling molecules.

Phosphatidylinositol 3-kinase, has been found to phosphorylate the 3-position of the inositol ring of phosphatidylinositol (PI) to form phosphatidylinositol 3-phosphate (PI-3P) (Whitman et al. (1988) Nature, 322: 664-646). In addition to PI, this enzyme also can phosphorylate phosphatidylinositol 4-phosphate and phosphatidylinositol 4,5-bisphosphate to produce phosphatidylinositol 3,4-bisphosphate and phosphatidylinositol 3,4,5-trisphosphate (PIP3), respectively (Auger et al. (1989) Cell, 57: 167-175). PI 3-kinase inhibitors are materials that reduce or eliminate either or both of these activities of PI 3-kinase. Identification, isolation and synthesis of such inhibitors is disclosed in U.S. Pat. No. 6,413,773 to Ptasznik et al.

The phrase "active derivative" refers to any structural derivative of wortmannin or LY294002 having a PI 3-kinase downregulatory activity, as measured, for example, by catalytic activity, binding studies, etc, in vivo or in vitro.

Alternatively, a modulator downregulating PI 3-kinase activity or gene expression according to this aspect of the present invention can be an activity neutralizing anti-PI 3-kinase antibody which binds, for example to the PI 3-kinase catalytic domain, or substrate bingeing site, thereby inhibiting PI 3-kinase catalytic activity. It will be appreciated, though, that since PI 3-kinase is an intracellular protein measures are taken to use modulators which may be delivered through the plasma membrane. In this respect a fragmented antibody such as a Fab fragment (described hereinunder), or a genetically engineered ScFv is preferably used.

A modulator that downregulates PI 3-kinase expression refers to any agent which affects PI 3-kinase synthesis (decelerates) or degradation (accelerates) either at the level of the mRNA or at the level of the protein. For example, downregulation of PI 3-kinase expression can be achieved using oligonucleotide molecules designed to specifically block the transcription of PI 3-kinase mRNA, or the translation of PI 3-kinase transcripts at the ribosome, can be used according to this aspect of the present invention. In one embodiment, such oligonucleotides are antisense oligonucleotides.

Design of antisense molecules which can be used to efficiently inhibit PI 3-kinase expression must be effected while considering two aspects important to the antisense approach. The first aspect is delivery of the oligonucleotide into the cytoplasm of the appropriate cells, while the second aspect is design of an oligonucleotide which specifically binds the designated mRNA within cells in a way which inhibits translation thereof. Sequences suitable for use in construction and synthesis of oligonucleotides which specifically bind to PI 3-kinase mRNA, genomic DNA, promoter and/or other control sequences of PI 3-kinase are available in published PI 3-kinase nucleotide sequences, including, but not limited to, GenBank Accession Nos: AF327656 (human gamma catalytic subunit); NM006219 (human beta subunit); NM002647 (human class III); NM181524 (human p85 alpha subunit); U86453 (human p110 delta isoform); and S67334 (human p110 beta isoform).

The prior art teaches of a number of delivery strategies which can be used to efficiently deliver oligonucleotides into a wide variety of cell types (see, for example, Luft (1998) J Mol Med 76(2): 75-6; Kronenwett et al. (1998) Blood 91(3): 852-62; Rajur et al. (1997) Bioconjug Chem 8(6): 93540; Lavigne et al. (1997) Biochem Biophys Res Commun 237(3): 566-71 and Aoki et al. (1997) Biochem Biophys Res Commun 231(3): 540-5).

In addition, algorithms for identifying those sequences with the highest predicted binding affinity for their target mRNA based on a thermodynamic cycle that accounts for the energetics of structural alterations in both the target mRNA and the oligonucleotide are also available [see, for example, Walton et al. (1999) Biotechnol Bioeng 65(1): 1-9].

Such algorithms have been successfully employed to implement an antisense approach in cells. For example, the algorithm developed by Walton et al. enabled scientists to successfully design antisense oligonucleotides for rabbit beta-globin (RBG) and mouse tumor necrosis factor-alpha (TNF alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiency of specific oligonucleotides using an in vitro system were also published (Matveeva et al. (1998) *Nature Biotechnology* 16, 1374-1375). Examples of antisense molecules which have been demonstrated capable of down-regulating the expression of PI 3-kinase are the PI 3-kinase specific antisense oligonucleotides described by Mood et al (Cell Signal 2004; 16:631-42), incorporated herein by reference. The production of PI 3-kinase-specific antisense molecules is disclosed by Ptasznik et al (U.S. Pat. No. 6,413,773), incorporated herein by reference.

In yet another embodiment, the method of ex-vivo expanding and at the same time inhibiting differentiation a population of stem cells, is effected by co-culturing with mesenchymal cells, wherein the cells are cultured in the presence of an inhibitor of sirtuin enzymes, and/or an agent capable of down-regulating activity and/or expression of a SIR protein and/or a down-stream effector of said SIR protein, thereby expanding and inhibiting differentiation of the population of stem cells.

As used herein the phrase "Sir2 protein" refers to at least one enzyme of the Sir2(sirtuin) family of deacetylases. Sir2 protein of the present invention is preferably a eukaryotic Sir2 protein, more preferably a mammalian Sir2 protein (e.g., mouse, primate, human), most preferably a human Sir2 protein. Examples of human Sir2 proteins include, but are not limited to, SIRT1 (GenBank Accession No. NP_036370), SIRT2 (GenBank Accession No. NP_085096), SIRT3 (GenBank Accession No. NP_036371), SIRT4 (GenBank Accession No. NP_036372), SIRT5 (GenBank Accession No. NP_112534), SIRT6 (GenBank Accession No. NM_057623) and SIRT7 (GenBank Accession No. NM_057622).

As used herein the phrase "down-stream effector of a Sir2 protein" refers to a reaction product of a Sir2 catalysis. An example of a down-stream effector of a Sir2 protein is O-acetyl-ADP-ribose (OAADPr) which is generated by the transfer of the acetyl group (removed from the Sir2 substrate) to the ADP-ribose. OAADPr is thought to act as a second messenger.

As used herein the phrase "Sir2 (sirtuin) activity" refers to the catalytic activity of Sir2 family of protein deacetylases, essentially hydrolysis of one molecule of NAD+ for each molecule of acetylated lysine, becoming deacetylated, and the production of one molecule of deacetylated lysine, nicotineamide and OAADPr. Other catalytic reactions catalyzed by this family of enzymes are also envisaged by the present invention, such as ribosyl-transferase (SIRT6). The phrase Sir2 activity as used herein, also refers to a biological function regulated by Sir2 family of proteins, such as for example, gene silencing, chromosome stability or cell survival (apoptosis) transcription factor regulation.

As used herein the phrase "Sir2 expression" refers to expression at the protein level and/or at the mRNA level. Generally, the level of expression is affected by the balance between protein synthesis and protein degradation (a similar balance exists also at the mRNA level).

Agents capable of down-regulating expression and/or activity of Sir2 proteins or down-stream effectors thereof include, but are not limited to, chemical inhibitors; oligonucleotide inhibitors directed at a nucleic acid sequence encoding Sir2 protein; and protein inhibitors, such as antibodies specifically recognizing a Sir2 protein; and peptide inhibitors. Specific agents modulating the expression of sirtuin expression, which can be used in accordance with the present invention are disclosed in detail in PCT IL 2005/000753, to Peled et al., filed Jul. 14, 2005.

Reducing the capacity of the cells in responding to retinoic acid, retinoids and/or Vitamin D, or to retinoic acid, retinoid X and/or Vitamin D receptor signaling may be effected, for example, by the administration of chemical inhibitors, including receptor antagonists. In another particular, the method of ex-vivo expanding and at the same time inhibiting differentiation of a population of stem cells, is effected by co-culturing with mesenchymal cells and providing the stem cells with ex-vivo culture conditions for reducing a capacity of the stem cells in responding to signaling pathways involving the retinoic acid receptor, retinoid-X receptor and/or Vitamin D receptor. Reducing the capacity of the cells to respond to retinoic acid, retinoid X and/or Vitamin D receptor signaling events, includes treating the cells with antagonists supplied continuously or for a short-pulse period, and is effected by a diminution or abrogation of cellular signaling pathways through their respective, cognate receptors.

Final concentrations of the antagonists may be, depending on the specific application, in the micromolar or millimolar ranges. For example, within about 0.1 μM to about 100 mM, preferably within about 4 μM to about 50 mM, more preferably within about 5 μM to about 40 mM.

Final concentrations of the nicotinamide or the analogs, derivatives or metabolites thereof and of the PI 3-kinase inhibitor are preferably, depending on the specific application, in the micro and up to millimolar ranges. For example, within about 1 μM and up to 0.1 mM to about 20 mM, preferably within about 1 mM to about 10 mM, more preferably within about 5 mM to about 10 mM.

In still another particular embodiment of this aspect of the present invention, culturing the stem and/or progenitor cells ex-vivo under conditions allowing for cell expansion and at the same time inhibiting differentiation of the stem cells is effected by culturing the cells in the presence of a copper chelator. PCT IL99/00444 to Peled, et al, which is incorporated by reference as if fully set for herein, discloses the use of heavy metal chelators, having high affinity for copper, for efficient ex-vivo expansion of stem and/or progenitor cells, while substantially inhibiting differentiation thereof.

Final concentrations of the chelator may be, depending on the specific application, in the micromolar or millimolar ranges. For example, within about 0.1 μM to about 100 mM, preferably within about 4 μM to about 50 mM, more preferably within about 5 μM to about 40 mM.

According to a preferred embodiment of the invention the chelator is a polyamine chelating agent, such as, but not limited to ethylendiamine, diethylenetriamine, triethylenetetramine, triethylenediamine, tetraethylenepentamine, aminoethylethanolamine, aminoethylpiperazine, pentaethylenehexamine, triethylenetetramine-hydrochloride, tetraethylenepentamine-hydrochloride, pentaethylenehexamine-hydrochloride, tetraethylpentamine, captopril, penicilamine, N,N'-bis(3-aminopropyl)-1,3-propanediamine, N,N,Bis(2 aminoethyl)1,3 propane diamine, 1,7-dioxa-4,10-diazacyclododecane, 1,4,8,11-tetraaza cyclotetradecane-5,7-dione, 1,4,7-triazacyclononane trihydrochloride, 1-oxa-4,7,10-triazacyclododecane, 1,4,8,12-tetraaza cyclopentadecane or 1,4,7,10-tetraaza cyclododecane, preferably tetraethylpentamine. The above listed chelators are known in their high affinity towards Copper ions.

In yet another particular embodiment of this aspect of the present invention, culturing the stem and/or progenitor cells ex-vivo under conditions allowing for cell expansion and at the same time inhibiting differentiation of the stem cells is effected by culturing the cells in the presence of a copper chelate. PCT IL03/00062 to Peled, et al, which is incorporated by reference as if fully set forth herein, discloses the use of copper chelates, complexes of copper and heavy metal chelators having high affinity for copper, for efficient ex-vivo expansion of stem and/or progenitor cells, while substantially inhibiting differentiation thereof.

The copper chelate, according to the present invention, is used in these and other aspects of the present invention, in the context of expanding a population of stem and/or progenitor cells, while at the same time reversibly inhibiting differentiation of the stem and/or progenitor cells. Providing the cells with the copper chelate maintains the free copper concentration available to the cells substantially unchanged.

The copper chelate according to the present invention is oftentimes capable of forming an organometallic complex with a transition metal other than copper. As metals other than copper are typically present in the cells (e.g., zinc) or can be administered to cells during therapy (e.g., platinum), it was found that copper chelates that can also interact with other metals are highly effective. Representative examples of such transition metals include, without limitation, zinc, cobalt, nickel, iron, palladium, platinum, rhodium and ruthenium.

The copper chelates of the present invention comprise copper ion (e.g., $Cu^{+1}$, $Cu^{+2}$) and one or more chelator(s). As is discussed hereinabove, preferred copper chelators include polyamine molecules, which can form a cyclic complex with the copper ion via two or more amine groups present in the polyamine.

Hence, the copper chelate used in the context of the different aspects and embodiments of the present invention preferably includes a polyamine chelator, namely a polymeric chain that is substituted and/or interrupted with 1-10 amine moieties, preferably 2-8 amine moieties, more preferably 4-6 amine moieties and most preferably 4 amine moieties.

The phrases "amine moiety", "amine group" and simply "amine" are used herein to describe a —NR'R" group or a —NR'— group, depending on its location within the molecule, where R' and R" are each independently hydrogen, alkyl, cycloalkyl, aryl, heteroaryl or heterocyclic, as these terms are defined hereinbelow.

The polyamine chelator can be a linear polyamine, a cyclic polyamine or a combination thereof.

A linear polyamine, according to the present invention, can be a polyamine that has a general formula I:

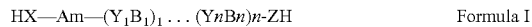

HX—Am—(Y$_1$B$_1$)$_1$ ... (Y$n$B$n$)$n$-ZH       Formula I wherein m is an integer from 1 to 10; n is an integer from 0 to 20; X and Z are each independently selected from the group consisting of an oxygen atom, a sulfur atom and a —NH group; Y$_1$ and Yn are each independently selected from the group consisting of an oxygen atom, a sulfur atom and a —NH group; A is an alkylene chain having between 1 and 10 substituted and/or non-substituted carbon atoms; and B$_1$ and Bn are each independently an alkylene chain having between 1 and 20 substituted and/or non-substituted carbon atoms, provided that at least one of X, Z, Y$_1$ and Yn is a —NH group and/or at least one of the carbon atoms in the alkylene chains is substituted by an amine group.

Hence, the linear polyamine, according to the present invention, is preferably comprised of one or more alkylene chains (Am, B$_1$ ... Bn, in Formula I), is interrupted by one or more heteroatoms such as S, O and N (Y$_1$ ... Yn in Formula I), and terminates with two such heteroatoms (X and Z in Formula I).

Alkylene chain A, as is described hereinabove, includes 1-10 substituted or non-substituted carbon atoms and is connected, at least at one end thereof, to a heteroatom (e.g., X in Formula I). Whenever there are more than one alkylene chains A (in cases where m is greater than one), only the first alkylene chain A is connected to X. However, m is preferably 1 and hence the linear polyamine depicted in Formula I preferably includes only one alkylene chain A.

Alkylene chain B, as is described hereinabove, includes between 1 and 20 substituted or non-substituted carbon atoms. The alkylene chain B is connected at its two ends to a heteroatom (Y$_1$ ... Yn and Z in Formula I).

The preferred linear polyamine delineated in Formula I comprises between 1 and 20 alkylene chains B, denoted as B$_1$ ... Bn, where "B$_1$ ... Bn" is used herein to describe a plurality of alkylene chains B, namely, B$_1$, B$_2$, B$_3$, ..., Bn-1 and Bn, where n equals 0-20. These alkylene chains can be the same or different. Each of B$_1$ ... Bn is connected to the respective heteroatom Y$_1$ ... Yn, and the last alkylene chain in the structure, Bn, is also connected to the heteroatom Z.

It should be noted that herein throughout, whenever an integer equals 0 or whenever a component of a formula is followed by the digit 0, this component is absent from the structure. For example, if n in Formula I equals 0, there is no alkylene chain B and no heteroatom Y are meant to be in the structure.

Preferably, n equals 2-10, more preferably 2-8 and most preferably 3-5. Hence, the linear polyamine depicted in Formula I preferably includes between 3 and 5 alkylene chains B, each connected to 3-5 heteroatoms Y.

The linear polyamine depicted in Formula I must include at least one amine group, as this term is defined hereinabove, preferably at least two amine groups and more preferably at least four amine groups. The amine group can be present in the structure as the heteroatoms X, Z or $Y_1 \ldots Y_n$, such that at least one of X, Z and $Y_1 \ldots Y_n$ is a —NH— group, or as a substituent of one or more of the substituted carbon atoms in the alkylene chains A and $B_1 \ldots B_n$. The presence of these amine groups is required in order to form a stable chelate with the copper ion, as is discussed hereinabove.

The alkylene chain A preferably has a general Formula II:

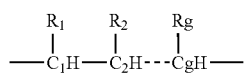

Formula II wherein g is an integer that equals 0 or 3-10.

Hence, the alkylene chain A is comprised of a plurality of carbon atoms $C_1, C_2, C_3 \ldots, C_{g-1}$ and $C_g$, substituted by the respective $R_1, R_2, R_3 \ldots, R_{g-1}$ and $R_g$ groups. Preferably, the alkylene chain A includes 2-10 carbon atoms, more preferably, 2-6 and most preferably 2-4 carbon atoms.

As is defined hereinabove, in cases where g equals 0, the component $C_gH(R_g)$ is absent from the structure and hence the alkylene chain A comprises only 2 carbon atoms.

$R_1$, $R_2$ and $R_g$ are each a substituent attached to the carbon atoms in A. Each of $R_1$, $R_2$ and $R_g$ can independently be a substituent such as, but not limited to, hydrogen, alkyl, alkenyl, alkynyl, aryl, cycloalkyl, heteroalicyclic, heteroaryl, halo, amino, alkylamino, arylamino, cycloalkylamino, heteroalicyclic amino, heteroarylamino, hydroxy, alkoxy, aryloxy, azo, C-amido, N-amido, ammonium, thiohydroxy, thioalkoxy, thioaryloxy, sulfonyl, sulfinyl, N-sulfonamide, S-sulfonamide, phosphonyl, phosphinyl, phosphonium, carbonyl, thiocarbonyl, C-carboxy, O-carboxy, C-thiocarboxy, O-thiocarboxy, N-carbamate, O-carbamate, N-thiocarbamate, O-thiocarbamate, urea, thiourea, borate, borane, boroaza, silyl, siloxy, silaza, aquo, alcohol, peroxo, amine oxide, hydrazine, alkyl hydrazine, aryl hydrazine, nitric oxide, cyanate, thiocyanate, isocyanate, isothiocyanate, cyano, alkylnitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, carboxylic acid, alkyl carboxylic acid, aryl carboxylic acid, sulfate, sulfite, bisulfite, thiosulfate, thiosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, phosphate, thiophosphate, phosphite, pyrophosphate, triphosphate, hydrogen phosphate, dihydrogen phosphate, guanidino, S-dithiocarbamate, N-dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraarylborate, tetraalkyl borate, tartarate, salicylate, succinate, citrate, ascorbate, saccharirate, amino acid, hydroxamic acid and thiotosylate.

Whenever $R_1$, $R_2$ or $R_g$ is hydrogen, its respective carbon atom in a non-substituted carbon atom.

As used herein, the term "alkyl" is a saturated aliphatic hydrocarbon including straight chain and branched chain groups. Preferably, the alkyl group has 1 to 20 carbon atoms. More preferably, it is a medium size alkyl having 1 to 10 carbon atoms. Most preferably, it is a lower alkyl having 1 to 4 carbon atoms. The alkyl group may be substituted or non-substituted. When substituted, the substituent group can be, for example, cycloalkyl, aryl, heteroaryl, heteroalicyclic, hydroxy, alkoxy, aryloxy, thiohydroxy, thioalkoxy, thioaryloxy, cyano, halo, carbonyl, thiocarbonyl, O-carbamate, N-carbamate, O-thiocarbamate, N-thiocarbamate, C-amido, N-amido, C-carboxy, O-carboxy, nitro, sulfonamide, silyl, guanidine, urea or amino, as these terms are defined hereinbelow.

The term "alkenyl" describes an alkyl group which consists of at least two carbon atoms and at least one carbon-carbon double bond.

The term "alkynyl" describes an alkyl group which consists of at least two carbon atoms and at least one carbon-carbon triple bond.

The term "cycloalkyl" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane. A cycloalkyl group may be substituted or unsubstituted. When substituted, the substituent group can be, for example, alkyl, aryl, heteroaryl, heteroalicyclic, hydroxy, alkoxy, aryloxy, thiohydroxy, thioalkoxy, thioaryloxy, cyano, halo, carbonyl, thiocarbonyl, C-carboxy, O-carboxy, O-carbamate, N-carbamate, C-amido, N-amido, nitro, or amino, as these terms are defined hereinabove or hereinbelow.

The term "aryl" describes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted. When substituted, the substituent group can be, for example, halo, trihalomethyl, alkyl, hydroxy, alkoxy, aryloxy, thiohydroxy, thiocarbonyl, C-carboxy, O-carboxy, O-carbamate, N-carbamate, O-thiocarbamate, N-thiocarbamate, C-amido, N-amido, sulfinyl, sulfonyl or amino, as these terms are defined hereinabove or hereinbelow.

The term "heteroaryl" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted. When substituted, the substituent group can be, for example, alkyl, cycloalkyl, halo, trihalomethyl, hydroxy, alkoxy, aryloxy, thiohydroxy, thiocarbonyl, sulfonamide, C-carboxy, O-carboxy, sulfinyl, sulfonyl, O-carbamate, N-carbamate, O-thiocarbamate, N-thiocarbamate, C-amido, N-amido or amino, as these terms are defined hereinabove or hereinbelow.

The term "heteroalicyclic" describes a monocyclic or fused ring group having in the ring(s) one or more atoms such as nitrogen, oxygen and sulfur. The rings may also have one or more double bonds. However, the rings do not have a completely conjugated pi-electron system. The heteroalicyclic may be substituted or unsubstituted. When substituted, the substituted group can be, for example, alkyl, cycloalkyl, aryl, heteroaryl, halo, trihalomethyl, hydroxy, alkoxy, aryloxy, thiohydroxy, thioalkoxy, thioaryloxy, cyano, nitro, carbonyl, thiocarbonyl, C-carboxy, O-carboxy, O-carbamate, N-carbamate, O-thiocarbamate, N-thiocarbamate, sulfinyl, sulfonyl, C-amido, N-amido or amino, as these terms are defined hereinabove or hereinbelow.

The term "halo" describes a fluorine, chlorine, bromine or iodine atom.

The term "amino", as is defined hereinabove with respect to an "amine" or an "amino group", is used herein to describe an —NR'R", wherein R' and R" are each independently hydrogen, alkyl, cycloalkyl, aryl, heteroaryl or heterocyclic, as these terms are defined hereinabove.

Hence, the terms "alkylamino", "arylamino", "cycloalkylamino", "heteroalicyclic amino" and "heteroarylamino" describe an amino group, as defined hereinabove, wherein at least one of R' and R" thereof is alkyl, aryl, cycloalkyl, heterocyclic and heteroaryl, respectively.

The term "hydroxy" describes an —OH group.

An "alkoxy" describes both an —O-alkyl and an —O-cycloalkyl group, as defined herein.

An "aryloxy" describes both an —O-aryl and an —O-heteroaryl group, as defined herein.

The term "azo" describes a —N=N group.

A "C-amido" describes a —C(=O)—NR'R" group, where R' and R" are as defined hereinabove.

An "N-amido" describes a R'C(=O)—NR"— group, where R' and R" are as defined hereinabove.

An "ammonium" describes an —N$^+$HR'R" group, where R' and R" are as defined hereinabove.

The term "thiohydroxy" describes a —SH group.

The term "thioalkoxy" describes both a —S-alkyl group and a —S-cycloalkyl group, as defined hereinabove.

The term "thioaryloxy" describes both a —S-aryl and a —S-heteroaryl group, as defined hereinabove.

A "sulfinyl" describes a —S(=O)—R group, where R can be, without limitation, alkyl, cycloalkyl, aryl and heteroaryl as these terms are defined hereinabove.

A "sulfonyl" describes a —S(=O)$_2$—R group, where R is as defined hereinabove.

A "S-sulfonamido" is a —S(=O)$_2$—NR'R" group, with R' and R" as defined hereinabove.

A "N-sulfonamido" is an R'(S=O)$_2$—NR"— group, with R' and R" as defined hereinabove.

A "phosphonyl" is a —O—P(=O)(OR')—R" group, with R' and R" as defined hereinabove.

A "phosphinyl" is a —PR'R" group, with R' and R" as defined hereinabove.

A "phosphonium" is a —P$^+$R'R"R'", where R' and R" are as defined hereinabove and R'" is defined as either R' or R".

The term "carbonyl" describes a —C(=O)—R group, where R is hydrogen, alkyl, cycloalkyl, aryl, heteroaryl (bonded through a ring carbon) or heteroalicyclic (bonded through a ring carbon) as defined hereinabove.

A "thiocarbonyl" describes a —C(=S)—R group, where R is as defined hereinabove with respect to the term "carbonyl".

A "C-carboxy" describes a —C(=O)—O—R groups, where R is as defined hereinabove with respect to the term "carbonyl".

An "O-carboxy" group refers to a RC(=O)—O— group, where R is as defined hereinabove with respect to the term "carbonyl".

A "carboxylic acid" is a C-carboxy group in which R is hydrogen.

A "C-thiocarboxy" is a —C(=S)—O—R groups, where R is as defined hereinabove with respect to the term "carbonyl".

An "O-thiocarboxy" group refers to an R—C(=S)—O— group, where R is as defined hereinabove with respect to the term "carbonyl".

The term "O-carbamate" describes an —OC(=O)—NR'R" group, with R' and R" as defined hereinabove.

A "N-carbamate" describes a R'—O—C(=O)—NR"— group, with R' and R" as defined hereinabove.

An "O-thiocarbamate" describes an —O—C(=S)—NR'R" group, with R' and R" as defined hereinabove.

A "N-thiocarbamate" describes a R'OC(=S)NR"— group, with R' and R" as defined hereinabove.

The term "urea" describes a —NR'—C(=O)—NR'R" group, with R', R" and R'" as defined hereinabove.

The term "thiourea" describes a —NR'—C(=S)—NR'R" group, with R', R" and R'" as defined hereinabove.

The term "borate" describes an —O—B—(OR)$_2$ group, with R as defined hereinabove.

The term "borane" describes a —B—R'R" group, with R' and R" as defined hereinabove.

The term "boraza" describes a —B(R')(NR"R'") group, with R', R" and R'" as defined hereinabove.

The term "silyl" describes a —SiR'R"R'", with R', R" and R'" as defined herein.

The term "siloxy" is a —Si—(OR)$_3$, with R as defined hereinabove.

The term "silaza" describes a —Si—(NR'R")$_3$, with R' and R" as defined herein.

The term "aquo" describes a H$_2$O group.

The term "alcohol" describes a ROH group, with R as defined hereinabove.

The term "peroxo" describes an —OOR group, with R as defined hereinabove.

As used herein, an "amine oxide" is a —N(=O)R'R"R'" group, with R', R" and R'" as defined herein.

A "hydrazine" is a —NR'—NR"R'" group, with R', R" and R'" as defined herein.

Hence, "alkyl hydrazine" and "aryl hydrazine" describe a hydrazine where R' is an alkyl or an aryl, respectively, and R" and R'" are as defined hereinabove.

The term "nitric oxide" is a —N=O group.

The term "cyano" is a —C≡N group.

A "cyanate" is an —O—C≡N group.

A "thiocyanate" is a "—S—C≡N group.

An "isocyanate" is a —N=C=O group.

An "isothiocyanate" is a —N=C=S group.

The terms "alkyl nitrile" and "aryl nitrile" describe a —R—C≡N group, where R is an alkyl or an aryl, respectively.

The terms "alkyl isonitrile" and "aryl isonitrile" describe a R—N≡C— group, where R is an alkyl or aryl, respectively.

A "nitrate" or "nitro" is a —NO$_2$ group.

A "nitrite" is an —O—N=O group.

An "azido" is a N$_3^+$ group.

An "alkyl sulfonic acid" and an "aryl sulfonic acid" describe a —R—SO$_2$—OH group, with R being an alkyl or an aryl, respectively.

An "alkyl sulfoxide", an "aryl sulfoxide" and an "alkyl aryl sulfoxide" describe a —R'S(=O)R" group, where R' and R" are each an alkyl, R' and R" are each an aryl and where R' is and alkyl and R" is an aryl, respectively.

An "alkyl sulfenic acid" and "aryl sulfenic acid" describe a —R—S—OH group, where R is an alkyl or an aryl, respectively.

An "alkyl sulfinic acid" and "aryl sulfinic acid" describe a —R—S(=O)—OH group where R is an alkyl or an aryl, respectively.

As used herein, the terms "alkyl carboxylic acid" and "aryl carboxylic acid" describe a —R—C(=O)—OH group, where R is an alkyl or an aryl, respectively.

An "alkyl thiol carboxylic acid" and an "aryl thiol carboxylic acid" describe a —R—C(=O)—SH group, where R is an alkyl or an aryl, respectively.

An "alkyl thiol thiocarboxylic acid" and an "aryl thiol thiocarboxylic acid" describe a —R—C(=S)—SH group, where R is an alkyl or an aryl, respectively.

A "sulfate" is a —O—SO$_2$—OR' group, with R' as defined hereinabove.

A "sulfite" group is a —O—S(=O)—OR' group, with R' as defined hereinabove.

A "bisulfite" is a sulfite group, where R' is hydrogen.

A "thiosulfate" is an —O—SO$_2$—SR' group, with R' as defined hereinabove.

A "thiosulfite" group is an —O—S(=O)—SR' group, with R' as defined hereinabove.

The terms "alkyl/aryl phosphine" describe a —R—PH$_2$ group, with R being an alkyl or an aryl, respectively, as defined above.

The terms "alkyl and/or aryl phosphine oxide" describe a —R'—PR"$_2$(=O) group, with R' and R" being an alkyl and/or an aryl, as defined hereinabove.

The terms "alkyl and/or aryl phosphine sulfide" describe a —R'—PR"$_2$(=S) group, with R' and R" being an alkyl and/or an aryl, as defined hereinabove.

The terms "alkyl/aryl phosphonic acid" describe a —R'—P(=O)(OH)$_2$ group, with R' being an alkyl or an aryl as defined above.

The terms "alkyl/aryl phosphinic acid" describes a —R'—P(OH)$_2$ group, with R' being an alkyl or an aryl as defined above.

A "phosphate" is a —O—P(=O)(OR')(OR") group, with R' and R" as defined hereinabove.

A "hydrogen phosphate" is a phosphate group, where R' is hydrogen.

A "dihydrogen phosphate" is a phosphate group, where R' and R" are both hydrogen.

A "thiophosphate" is a —S—P(=O)(OR')$_2$ group, with R' as defined hereinabove.

A "phosphite" is an —O—P(OR')$_2$ group, with R' as defined hereinabove.

A "pyrophosphite" is an —O—P—(OR')—O—P(OR")$_2$ group, with R' and R" as defined hereinabove.

A "triphosphate" describes an —OP(=O)(OR')—O—P(=O)(OR")—O—P(=O)(OR''')$_2$, with R', R" and R''' are as defined hereinabove.

As used herein, the term "guanidine" describes a —R'NC(=N)—NR"R''' group, with R', R" and R''' as defined herein.

The term "S-dithiocarbamate" describes a —SC(=S)—NR'R" group, with R' and R" as defined hereinabove.

The term "N-dithiocarbamate" describes an R'SC(=S)—NR"— group, with R' and R" as defined hereinabove.

A "bicarbonate" is an —O—C(=O)—O$^-$ group.

A "carbonate" is an —O—C(=O)—OH group.

A "perchlorate" is an —O—Cl(=O)$_3$ group.

A "chlorate" is an —O—Cl(=O)$_2$ group.

A "chlorite" is an —O—Cl(=O) group.

A "hypochlorite" is an —OCl group.

A "perbromate" is an —O—Br(=O)$_3$ group.

A "bromate" is an —O—Br(=O)$_2$ group.

A "bromite" is an —O—Br(=O) group.

A "hypobromite" is an —OBr group.

A "periodate" is an —O—I(=O)$_3$ group.

A "iodate" is an —O—I(=O)$_2$ group.

The term "tetrahalomanganate" describes MnCl$_4$, MnBr$_4$ and MnI$_4$.

The term "tetrafluoroborate" describes a —BF$_4$ group.

A "tetrafluoroantimonate" is a SbF$_6$ group.

A "hypophosphite" is a —P(OH)$_2$ group.

The term "metaborate" describes the group

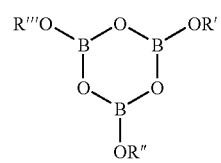

where R', R" and R''' are as defined hereinabove.

The terms "tetraalkyl/tetraaryl borate" describe a R'B$^-$ group, with R' being an alkyl or an aryl, respectively, as defined above.

A "tartarate" is an —OC(=O)—CH(OH)—CH(OH)—C(=O)OH group.

A "salycilate" is the group

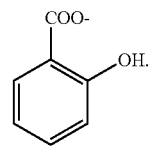

A "succinate" is an —O—C(=O)—(CH$_2$)$_2$—COOH group.

A "citrate" is an —O—C(=O)—CH$_2$—CH(OH)(COOH)—CH$_2$—COOH group.

An "ascorbate" is the group

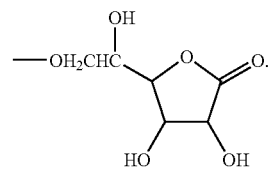

A "saccharirate" is an oxidized saccharide having two carboxylic acid group.

The term "amino acid" as used herein includes natural and modified amino acids and hence includes the 21 naturally occurring amino acids; those amino acids often modified post-translationally in vivo, including, for example, hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids which are linked via a peptide bond or a peptide bond analog to at least one addition amino acid as this term is defined herein.

A "hydroxamic acid" is a —C(=O)—NH—OH group.

A "thiotosylate" is the group

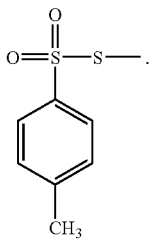

Similarly, each of the alkylene chains $B_1 \ldots Bn$ independently has a general formula III:

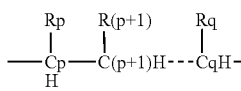

Formula III wherein p is an integer that equals 0 or g+1 and q is an integer from g+2 to g+20.

Hence, each of the alkylene chains $B_1 \ldots Bn$ is comprised of a plurality of carbon atoms Cp, Cp+1, Cp+2 ..., Cq−1 and Cq, substituted by the respective Rp, Rp+1, Rp+2 ..., Rq−1 and Rq groups. Preferably, each of the alkylene chains $B_1 \ldots Bn$ includes 2-20 carbon atoms, more preferably 2-10, and most preferably 2-6 carbon atoms.

As is defined hereinabove, in cases where p equals 0, the component —CpH(Rp)— is absent from the structure. In cases where p equals g+1, it can be either 1 or 4-11. The integer q can be either 2 or 5-20.

Each of the substituents Rp, Rp+1 ... Rn can be any of the substituents described hereinabove with respect to $R_1$, $R_2$ and Rg.

Hence, a preferred linear polyamine according to the present invention includes two or more alkylene chains. The alkylene chains are interrupted therebetween by a heteroatom and each is connected to a heteroatom at one end thereof. Preferably, each of the alkylene chains include at least two carbon atoms, so as to enable the formation of a stable chelate between the heteroatoms and the copper ion.

The linear polyamine delineated in Formula I preferably includes at least one chiral carbon atom. Hence, at least one of $C_1$, $C_2$ and Cg in the alkylene chain A and/or at least one of Cp, Cp+1 and Cq in the alkylene chain B is chiral.

A preferred linear polyamine according to the present invention is tetraethylenepentamine. Other representative examples of preferred linear polyamines usable in the context of the present invention include, without limitation, ethylenediamine, diethylenetriamine, triethylenetetramine, triethylenediamine, aminoethylethanolamine, pentaethylenehexamine, triethylenetetramine, N,N'-bis(3-aminopropyl)-1,3-propanediamine, and N,N'-Bis(2-aminoethyl)-1,3 propanediamine.

In cases where the polyamine chelator is a cyclic polyamine, the polyamine can have a general formula IV:

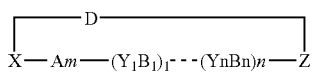

Formula IV wherein m is an integer from 1 to 10; n is an integer from 0 to 20; X and Z are each independently selected from the group consisting of an oxygen atom, a sulfur atom and a —NH group; $Y_1$ and Yn are each independently selected from the group consisting of an oxygen atom, a sulfur atom and a —NH group; A is an alkylene chain having between 1 and 10 substituted and/or non-substituted carbon atoms; $B_1$ and Bn are each independently an alkylene chain having between 1 and 20 substituted and/or non-substituted carbon atoms; and D is a bridging group having a general formula V:

U—W—V  Formula V whereas U and V are each independently selected from the group consisting of substituted hydrocarbon chain and non-substituted hydrocarbon chain; and W is selected from the group consisting of amide, ether, ester, disulfide, thioether, thioester, imine and alkene, provided that at least one of said X, Z, $Y_1$ and Yn is a —NH group and/or at least one of said carbon atoms in said alkylene chains is substituted by an amine group.

Optionally, the cyclic polyamine has one of the general formulas VI-X:

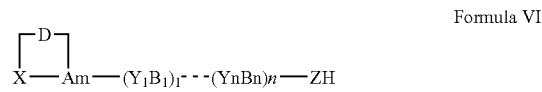

Formula VI

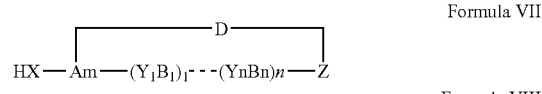

Formula VII

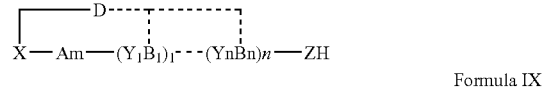

Formula VIII

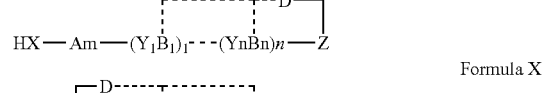

Formula IX

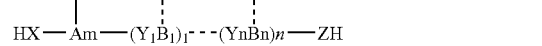

Formula X wherein m, n, X, $Y_1$, Yn, Z, A, B and D are as described above and further wherein should the bridging group D is attached at one end to A (Formulas VI, VII and X), U or V are being attached to one carbon atom in the alkylene chain and should D is attached at one end to B1 or Bn (Formulas VIII, IX and X), U or V are being attached to one carbon atom in the alkylene chain.

Hence, a preferred cyclic polyamine according to the present invention includes two or more alkylene chains, A, $B_1 \ldots Bn$, as is detailed hereinabove with respect to the linear polyamine. The alkylene chains can form a cyclic structure by being connected, via the bridging group D, between the ends thereof, namely between the heteroatoms X and Z (Formula IV). Optionally, the alkylene chains can form a conformationally restricted cyclic structure by being connected, via the bridging group D, therebetween (Formula X). Further optionally, a conformationally restricted cyclic structure can be formed by connecting one alkylene chain to one terminal heteroatom (X or Z, Formulas VI-IX).

As is described hereinabove, in cases where the cyclic structure is formed by connecting one alkylene chain to one terminal heteroatom, as is depicted in Formulas VI-IX, the bridging group D connects a terminal heteroatom, namely X or Z, and one carbon atom in the alkylene chains A and $B_1 \ldots Bn$. This carbon atom can be anyone of $C_1$, $C_2$, Cg, Cp, Cp+1 and Cq described hereinabove.

As is further described hereinabove, the cyclic structure is formed by the bridging group D, which connects two components in the structure. The bridging group D has a general formula U—W—V, where each of U and V is a substituted or non-substituted hydrocarbon chain.

As used herein, the phrase "hydrocarbon chain" describes a plurality of carbon atoms which are covalently attached one to another and are substituted, inter alia, by hydrogen atoms. The hydrocarbon chain can be saturated, unsaturated, branched or unbranched and can therefore include one or more alkyl, alkenyl, alkynyl, cycloalkyl and aryl groups and combinations thereof.

The length of the hydrocarbon chains, namely the number of carbon atoms in the chains, is preferably determined by the structure of the cyclic polyamine, such that on one hand, the ring tension of the formed cyclic structure would be minimized and on the other hand, an efficient chelation with the copper ion would be achieved.

When the hydrocarbon chain is substituted, the substituents can be any one or combinations of the substituents described hereinabove with respect to $R_1$, $R_2$ and Rg in the linear polyamine.

The two hydrocarbon chains are connected therebetween by the group W, which can be amide, ether, ester, disulfide, thioether, thioester, imine and alkene.

As used herein, the term "ether" is an —O— group.
The term "ester" is a —C(=O)—O— group.
A "disulfide" is a —S—S— group.
A "thioether" is a —S— group.
A "thioester" is a —C(=O)—S— group.
An "imine" is a —C(=NH)— group.
An "alkene" is a —CH=CH— group.

The bridging group D is typically formed by connecting reactive derivatives of the hydrocarbon chains U and V, so as to produce a bond therebetween (W), via well-known techniques, as is described, for example, in U.S. Pat. No. 5,811,392.

As is described above with respect to the linear polyamine, the cyclic polyamine must include at least one amine group, preferably at least two amine groups and more preferably at least four amine groups, so as to form a stable copper chelate.

A preferred cyclic polyamine according to the present invention is cyclam (1,4,8,11-tetraazacyclotetradecane).

As is described hereinabove, the polyamine chelator of the present invention can further include a multimeric combination of one or more linear polyamine(s) and one or more cyclic polyamine(s). Such a polyamine chelator can therefore be comprised of any combinations of the linear and cyclic polyamines described hereinabove.

Preferably, such a polyamine chelator has a general Formula XI:

Formula XI

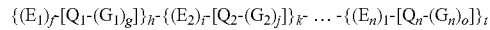

wherein n is an integer greater than 1; each of f, g, h, i, j, k, l, o and t is independently an integer from 0 to 10; each of $E_1$, $E_2$ and En is independently a linear polyamine, as is described hereinabove; each of $G_1$, $G_2$ and Gn is independently a cyclic polyamine as is described hereinabove; and each of $Q_1$, $Q_2$ and Qn is independently a linker linking between two of said polyamines, provided that at least one of said $Q_1$, $Q_2$ and Qn is an amine group and/or at least one of said linear polyamine and said cyclic polyamine has at least one free amine group.

Each of $E_1$, $E_2$ and En in Formula XI represent a linear polyamine as is described in detail hereinabove, while each of $G_1$, $G_2$ and Gn represents a cyclic polyamine as is described in detail hereinabove.

The polyamine described in Formula XI can include one or more linear polyamine(s), each connected to another linear polyamine or to a cyclic polyamine.

Each of the linear or cyclic polyamines in Formula XI is connected to another polyamine via one or more linker(s), represented by $Q_1$, $Q_2$ and Qn in Formula XI.

Each of the linker(s) $Q_1$, $Q_2$ and Qn can be, for example, alkylene, alkenylene, alkynylene, arylene, cycloalkylene, heteroarylene, amine, azo, amide, sulfonyl, sulfinyl, sulfonamide, phosphonyl, phosphinyl, phosphonium, ketoester, carbonyl, thiocarbonyl, ester, ether, thioether, carbamate, thiocarbamate, urea, thiourea, borate, borane, boroaza, silyl, siloxy and silaza.

As used herein, the term "alkenylene" describes an alkyl group which consists of at least two carbon atoms and at least one carbon-carbon double bond.

The term "alkynylene" describes an alkyl group which consists of at least two carbon atoms and at least one carbon-carbon triple bond.

The term "cycloalkylene" describes an all-carbon monocyclic or fused ring (i.e., rings which share an adjacent pair of carbon atoms) group wherein one of more of the rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene, and adamantane.

The term "arylene" describes an all-carbon monocyclic or fused-ring polycyclic (i.e., rings which share adjacent pairs of carbon atoms) groups having a completely conjugated pi-electron system. Examples, without limitation, of aryl groups are phenyl, naphthalenyl and anthracenyl. The aryl group may be substituted or unsubstituted.

The term "heteroarylene" describes a monocyclic or fused ring (i.e., rings which share an adjacent pair of atoms) group having in the ring(s) one or more atoms, such as, for example, nitrogen, oxygen and sulfur and, in addition, having a completely conjugated pi-electron system. Examples, without limitation, of heteroaryl groups include pyrrole, furane, thiophene, imidazole, oxazole, thiazole, pyrazole, pyridine, pyrimidine, quinoline, isoquinoline and purine. The heteroaryl group may be substituted or unsubstituted.

As used in the context of the linker of the present invention, the term "amine" describes an —NR'—, wherein R' can be hydrogen, alkyl, cycloalkyl, aryl, heteroaryl or heterocyclic, as these terms are defined hereinabove.

As is further used in the context of the linker of the present invention, the term "azo" describes a —N=N— group.

The term "amide" describes a —C(=O)—NR'— group, where R' is as defined hereinabove.

The term "ammonium" describes an —N$^+$HR'— group, where R' is as defined hereinabove.

The term "sulfinyl" describes a —S(=O)— group.
The term "sulfonyl" describes a —S(=O)$_2$— group.
The term "sulfonamido" describes a —S(=O)$_2$—NR'— group, with R' as defined hereinabove.

The term "phosphonyl" describes a —O—P(=O)(OR')— group, with R' as defined hereinabove.

The term "phosphinyl" describes a —PR'— group, with R' as defined hereinabove.

The term "phosphonium" is a —P$^+$R'R", where R' and R" are as defined hereinabove.

The term "ketoester" describes a —C(=O)—C(=O)—O— group.

The term "carbonyl" describes a —C(=O)— group.

The term "thiocarbonyl" describes a —C(=S)— group.

The term "carbamate" describes an —OC(=O)—NR'— group, with R' as defined hereinabove.

The term "thiocarbamate" describes an —OC(=S)—NR— group, with R' as defined hereinabove.

The term "urea" describes an —NR'—C(=O)—NR"— group, with R' and R" and as defined hereinabove.

The term "thiourea" describes a —NR'—C(=S)—NR'— group, with R' and R" as defined hereinabove.

The term "borate" describes an —O—B—(OR)— group, with R as defined hereinabove.

The term "borane" describes a —B—R—'— group, with R as defined hereinabove.

The term "boraza" describes a —B(NR'R")— group, with R' and R" as defined hereinabove.

The term "silyl" describes a —SiR'R"—, with R' and R" as defined herein.

The term "siloxy" is a —Si—(OR)$_2$—, with R as defined hereinabove.

The term "silaza" describes a —Si—(NR'R")$_2$— with R' and R" as defined herein.

It should be noted that all the terms described hereinabove in the context of the linker of the present invention are the same as described above with respect to the substituents. However, in distinction from the substituent groups, which are connected to a component at one end thereof, the linker groups are connected to two components at two sites thereof and hence, these terms have been redefined with respect to the linker.

As has been mentioned hereinabove, according to the presently most preferred embodiment of the present invention, the polyamine chelator is tetraethylenepentamine (TEPA). However, other preferred polyamine chelators include, without limitation, ethylendiamine, diethylenetriamine, triethylenetetramine, triethylenediamine, aminoethylethanolamine, aminoethylpiperazine, pentaethylenehexamine, triethylenetetramine, captopril, penicilamine, N,N'-bis(3-aminopropyl)-1,3-propanediamine, N,N'-Bis(2-aminoethyl)-1,3-propanediamine, 1,7-dioxa-4,10-diazacyclododecane, 1,4,8,11-tetraazacyclotetradecane-5,7-dione, 1,4,7-triazacyclononane, 1-oxa-4,7,10-triazacyclododecane, 1,4,8,12-tetraazacyclopentadecane and 1,4,7,10-tetraazacyclododecane.

The above listed preferred chelators are known in their high affinity towards copper ions. However, these chelators are further beneficially characterized by their substantial affinity also towards other transition metals, as is described by Ross and Frant [22], which is incorporated by reference as if fully set forth herein.

All the polyamine chelators described hereinabove can be either commercially obtained or can be synthesized using known procedures such as described, for example, in: T. W. Greene (ed.), 1999 ("Protective Groups in Organic Synthesis" 3ed Edition, John Wiley & Sons, Inc., New York 779 pp); or in: R. C. Larock and V. C. H. Wioley, "Comprehensive Organic Transformations—A Guide to Functional Group Preparations", (1999) $2^{nd}$ Edition.

The copper chelate can be provided to the cell culture medium. The final concentrations of copper chelate may be, depending on the specific application, in the micromolar or millimolar ranges, for example, within about 0.1 μM to about 100 mM, preferably within about 4 μM to about 50 mM, more preferably within about 5 μM to about 40 mM. As is described hereinabove, the copper chelate is provided to the cells so as to maintain the free copper concentration of the cells substantially unchanged during cell expansion.

The stem cells used in the present invention can be of various origin. According to a preferred embodiment of the present invention, the stem and/or progenitor cells are derived from a source selected from the group consisting of hematopoietic cells, umbilical cord blood cells, and mobilized peripheral blood cells. Methods of preparation of stem cells are well known in the art, commonly selecting cells expressing one or more stem cell markers such as CD34, CD133, etc, or lacking markers of differentiated cells. Selection is usually by FACS, or immunomagnetic separation, but can also be by nucleic acid methods such as PCR (see Materials and Experimental Methods hereinbelow). Embryonic stem cells and methods of their retrieval are well known in the art and are described, for example, in Trounson A O (Reprod Fertil Dev (2001) 13: 523), Roach M L (Methods Mol Biol (2002) 185: 1), and Smith A G (Annu Rev Cell Dev Biol (2001) 17:435). Adult stem cells are stem cells, which are derived from tissues of adults and are also well known in the art. Methods of isolating or enriching for adult stem cells are described in, for example, Miraglia, S. et al. (1997) Blood 90: 5013, Uchida, N. et al. (2000) Proc. Natl. Acad. Sci. USA 97: 14720, Simmons, P. J. et al. (1991) Blood 78: 55, Prockop D J (Cytotherapy (2001) 3: 393), Bohmer R M (Fetal Diagn Ther (2002) 17: 83) and Rowley S D et al. (Bone Marrow Transplant (1998) 21: 1253), Stem Cell Biology Daniel R. Marshak (Editor) Richard L. Gardner (Editor), Publisher: Cold Spring Harbor Laboratory Press, (2001) and Hematopoietic Stem Cell Transplantation. Anthony D. Ho (Editor) Richard Champlin (Editor), Publisher: Marcel Dekker (2000).

Peled et al (IL 2004/00064) demonstrated that unselected cells from the total nucleated cell (TNC) fraction of cord blood can be expanded ex-vivo while inhibiting differentiation thereof, and used for transplantation. Thus, in one embodiment of the present invention, the population of cells comprising stem cells is unselected mononuclear cells. PCT IL03/00681 to Peled, et al, which is incorporated by reference as if fully set for herein, discloses the use of molecules such as copper chelators, copper chelates and retinoic acid receptor (RAR) antagonists which are capable of repressing differentiation and stimulating and prolonging proliferation of hematopoietic stem cells when the source of cells includes the entire fraction of mononuclear blood cells, namely non-enriched stem cells.

As used herein, the phrase "hematopoietic mononuclear cells" refers to the entire repertoire of white blood cells present in a blood sample, usually hematopoietic mononuclear cells which comprise a major fraction of hematopoietic committed cells and a minor fraction of hematopoietic stem and progenitor cells. In a healthy human being, the white blood cells comprise a mixture of hematopoietic lineages committed and differentiated cells (typically over 99% of the mononuclear cells are lineages committed cells) including, for example: Lineage committed progenitor cells $CD34^+$ $CD33^+$ (myeloid committed cells), $CD34^+CD3^+$ (lymphoid committed cells) $CD34^+CD41^+$ (megakaryocytic committed cells) and differentiated cells—$CD34^-CD33^+$ (myeloids, such as granulocytes and monocytes), $CD34^-CD3^+$, $CD34^-CD19^+$ (T and B cells, respectively), $CD34^-CD41^+$ (megakaryocytes), and hematopoietic stem and early progenitor cells such as $CD34^+$Lineage negative ($Lin^-$), CD34– Lineage negative $CD34^+CD38^-$ (typically less than 1%).

Hematopoietic mononuclear cells are typically obtained from a blood sample by applying the blood sample onto a Ficoll-Hypaque layer and collecting, following density-cushion centrifugation, the interface layer present between the Ficoll-Hypaque and the blood serum, which interface layer essentially entirely consists of the white blood cells present in the blood sample. However, hematopoietic mononuclear cells can also be used for ex-vivo expansion according to the methods of the present invention, without the Ficoll separation.

Presently, hematopoietic stem cells can be obtained by further enrichment of the hematopoietic mononuclear cells obtained by differential density centrifugation as described above. This further enrichment process is typically performed by immuno-separation such as immunomagnetic-separation or FACS and results in a cell fraction that is enriched for hematopoietic stem cells (for detailed description of enrichment of hematopoietic stem cells, see Materials and Experimental Procedures in the Examples section hereinbelow).

Hence, using hematopoietic mononuclear cells as a direct source for obtaining expanded population of hematopoietic stem cells circumvents the need for stem cell enrichment prior to expansion, thereby substantially simplifying the process in terms of both efficiency and cost.

The newly discovered effect of co-culturing mesenchymal cells and stem cells on stem cell expansion and inhibition of differentiation is applicable for maximizing the ex-vivo expansion of various types of cells including hematopoietic cells, hepatocytes and embryonic stem cells. Such ex-vivo expanded cells can be applied in several clinical situations. The following lists a few.

Hematopoietic cell transplantation: Transplantation of hematopoietic cells has become the treatment of choice for a variety of inherited or malignant diseases. While early transplantation procedures utilized the entire bone marrow (BM) population, recently, more defined populations, enriched for stem cells ($CD34^+$ cells) have been used [Van Epps Blood Cells 20:411, (1994)]. In addition to the marrow, such cells could be derived from other sources such as peripheral blood (PB) and neonatal umbilical cord blood (CB) [Emerson Blood 87:3082 (1996)]. Compared to BM, transplantation with PB cells shortens the period of pancytopenia and reduces the risks of infection and bleeding [Brugger N Engl J Med 333:283, 1995; Williams Blood 87:1687, (1996); Zimmerman J Heamatotherapy 5:247, (1996)].

An additional advantage of using PB for transplantation is its accessibility. The limiting factor for PB transplantation is the low number of circulating pluripotent stem/progenitor cells.

To obtain enough PB-derived stem cells for transplantation, these cells are "harvested" by repeated leukophoresis following their mobilization from the marrow into the circulation by treatment with chemotherapy and cytokines [Brugger N Engl J Med 333:283, 1995; Williams Blood 87:1687, (1996)]. Such treatment is obviously not suitable for normal donors.

The use of ex-vivo expanded stem cells for transplantation has the following advantages [Koller Blood 82:378, (1993); Lebkowski Blood Cells 20:404, (1994)]:

It reduces the volume of blood required for reconstitution of an adult hematopoietic system and may obviate the need for mobilization and leukophoresis [Brugger N Engl J Med 333:283, 1995].

It enables storage of small number of PB or CB stem cells for potential future use.

In the case of autologous transplantation of recipients with malignancies, contaminating tumor cells in autologous infusion often contribute to the recurrence of the disease [Brugger N Engl J Med 333:283, 1995]. Selecting and expanding $CD34^+$ stem cells will reduce the load of tumor cells in the final transplant.

The cultures provide a significant depletion of T lymphocytes, which may be useful in the allogeneic transplant setting for reducing graft-versus-host disease.

Clinical studies indicate that transplantation of ex-vivo expanded cells derived from a small number of PB $CD34^+$ cells can restore hematopoiesis in recipients treated with high doses of chemotherapy, although the results do not yet allow firm conclusions about long term in-vivo hematopoietic capabilities of these cultured cells [Brugger N Engl J Med 333: 283, 1995; Williams Blood 87:1687, (1996)].

For successful transplantation, shortening of the duration of the cytopenic phase, as well as long-term engraftment, is crucial. Inclusion of intermediate and late progenitor cells in the transplant could accelerate the production of donor-derived mature cells thereby shortening the cytopenic phase. It is important, therefore, that ex-vivo expanded cells include, in addition to stem cells, more differentiated progenitor cells in order to optimize short-term recovery and long-term restoration of hematopoiesis. Expansion of intermediate and late progenitor cells, especially those committed to the neutrophilic and megakaryocytic lineages, concomitant with expansion of stem cells, should serve this purpose [Sandstrom Blood 86:958, (1995)].

Such cultures may be useful in restoring hematopoiesis in recipients with completely ablated bone marrow, as well as in providing a supportive measure for shortening recipient bone marrow recovery following conventional radio- or chemotherapies.

Tissue regeneration: Stem cell populations expanded by co-culturing with mesenchymal cells, according to the methods of the present invention, can be used for the promotion of tissue regeneration. Transplantation of stem cells, with or without supportive stroma, has great promise for benefits in regenerative medicine, reconstructive surgery, tissue engineering, regenerating new tissues and naturally healing diseased or injured organs (for review see Czyz et al, Biol Chem, 2003; 384:1391-40, Sylvester et al Arch Surg 2004; 139:93-99).

Recent reports have demonstrated the capability of transplanted or transfused stem cells to enhance regeneration in non-homologous tissue, other than that which the stem cells were derived. For example, enhanced myogenesis and angiogenesis in infarcted myocardium have been observed following infusion of bone marrow stem cells (Tse et al, Lancet 2003, 361:47-79, Jackson et al J Clin Invest 2001; 107:1395-402, Orlic et al Nature 2001; 410:701-5; Lee et al, Cell Cycle 2005; 4:861-64, Nagaya et al Am J Heart Circ Phys 2004; 287:H2670-76). Other studies have shown bone marrow, endothelial and skeletal muscle stem cells to be beneficial in ischemic renal injury (Togel et al, AJP Renal Phys 2005; 289:F31-F42 and Arriero, et al, AMJ Ren Phys 2004; 287: F621-27).

Prenatal diagnosis of genetic defects in scarce cells: Prenatal diagnosis involves the collection of embryonic cells from a pregnant woman, in utero, and analysis thereof for genetic defects. A preferred, non-invasive, means of collecting embryonic cells involves separation of embryonic nucleated red blood cell precursors that have infiltrated into peripheral maternal circulation. However, since the quantities of these cells are quite scarce, a further application of the present invention would be the expansion of such cells according to methods described herein, prior to analysis. The present invention, therefore, offers a means to expand embryonic cells for applications in prenatal diagnosis.

Gene therapy: For successful long-term gene therapy, a high frequency of genetically modified stem cells with transgenes stably integrated within their genome, is an obligatory requirement. In BM tissue, while the majority of cells are cycling progenitors and precursors, stem cells constitute only a small fraction of the cell population and most of them are in a quiescent, non-cycling state. Viral-based (e.g., retroviral) vectors require active cell division for integration of the transgene into the host genome. Therefore, gene transfer into fresh BM stem cells is highly inefficient. The ability to expand a purified population of stem cells and to regulate their cell division ex-vivo would provide for an increased probability of their genetic modification [Palmiter Proc Natl Acad Sci USA 91(4): 1219-1223, (1994)].

Adoptive immunotherapy: Ex-vivo-expanded, defined lymphoid subpopulations have been studied and used for adoptive immunotherapy of various malignancies, immunodeficiencies, viral and genetic diseases [Freedman Nature Medicine 2: 46, (1996); Heslop Nature Medicine 2: 551, (1996); Protti Cancer Res 56: 1210, (1996)].

The treatment enhances the required immune response or replaces deficient functions. This approach was pioneered clinically by Rosenberg et al. [Rosenberg J Natl Cancer Inst. 85: 622, 1993] using a large number of autologous and also allogeneic ex-vivo expanded non-specific killer T cells, and subsequently ex-vivo expanded specific tumor infiltrating lymphocytes.

Functionally active, antigen-presenting cells could be grown from a starting population of $CD34^+$ PB cells in cytokine-supported cultures, as well. These cells can present soluble protein antigens to autologous T cells in-vitro and, thus, offer new prospects for the immunotherapy of minimal residual disease after high dose chemotherapy. Ex-vivo expansion of antigen-presenting dendritic cells has been studied as well, and is an additional promising application of the currently proposed technology [Bernhard Cancer Res 10: 99, (1995); Fisch Eur J Immunol 26: 595, (1996); Siena Expt Hematol 23:1463, (1996)].

Additional Examples for Both Ex-Vivo and In-Vivo Applications:

Additional applications of stem and progenitor cell expansion include skin regeneration, hepatic regeneration, muscle regeneration and stimulation of bone growth for applications in osteoporosis.

According to one aspect of the present invention, the ex-vivo expansion of populations of stem cells, according to the features described hereinabove, can be utilized for expanding a population of renewable stem cells ex-vivo for implanting the cells in an organ of a subject in need thereof.

Implanting can be by means of direct injection into an organ, injection into the bloodstream, intraperitoneal injection, etc. Suitable methods of implantation can be determined by monitoring the homing of the implanted cells to the desired organ, the expression of desired organ-specific genes or markers, and the function of the endodermally-derived organ of the subject. In the pancreas, for example, maintenance of euglycemia, secretion of insulin and/or C peptide can be a measure of the restoration of function to a diabetic host animal following cell replacement therapy as disclosed hereinbelow. In the liver, for example, albumin synthesis can be monitored.

As described hereinabove, prior to implantation the stem and/or progenitor cells can be co-cultured with mesenchymal cells ex-vivo under conditions allowing for cell proliferation and, at the same time, substantially inhibiting differentiation thereof. According to preferred embodiments of the present invention, providing the stem cells with the conditions for ex-vivo cell proliferation comprises providing the cells with nutrients and with cytokines. Preferably, the cytokines are early acting cytokines, such as, but not limited to, stem cell factor, FLT3 ligand, interleukin-1, interleukin-2, interleukin-3, interleukin-6, interleukin-10, interleukin-12, tumor necrosis factor-α and thrombopoietin. It will be appreciated in this respect that novel cytokines are continuously discovered, some of which may find uses in the methods of cell expansion of the present invention.

Late acting cytokines can also be used. These include, for example, granulocyte colony stimulating factor, granulocyte/macrophage colony stimulating factor, erythropoietin, FGF, EGF, NGF, VEGF, LIF, Hepatocyte growth factor and macrophage colony stimulating factor.

The present invention can be used for gene therapy. Gene therapy as used herein refers to the transfer of genetic material (e.g., DNA or RNA) of interest into a host to treat or prevent a genetic or acquired disease or condition or phenotype. The genetic material of interest encodes a product (e.g., a protein, polypeptide, peptide, functional RNA, antisense) whose production in vivo is desired. For example, the genetic material of interest can encode a hormone, receptor, enzyme, polypeptide or peptide of therapeutic value. For review see, in general, the text "Gene Therapy" (Advanced in Pharmacology 40, Academic Press, 1997).

Two basic approaches to gene therapy have evolved: (i) ex-vivo or cellular gene therapy; and (ii) in vivo gene therapy. In ex-vivo gene therapy cells are removed from a patient, and while being cultured are treated in-vitro. Generally, a functional replacement gene is introduced into the cells via an appropriate gene delivery vehicle/method (transfection, transduction, homologous recombination, etc.) and an expression system as needed and then the modified cells are expanded in culture and returned to the host/patient. These genetically re-implanted cells have been shown to express the transfected genetic material in situ.

Hence, in one embodiment of the present invention, the stem and/or progenitor cells are genetically modified cells. In a preferred embodiment, genetically modifying the cells is effected by a vector, which comprises the exogene or transgene, which vector is, for example, a viral vector or a nucleic acid vector. Many viral vectors suitable for use in cellular gene therapy are known, examples are provided hereinbelow. Similarly, a range of nucleic acid vectors can be used to genetically transform the expanded cells of the invention, as is further described below.

Accordingly, the expanded cells of the present invention can be modified to express a gene product. As used herein, the phrase "gene product" refers to proteins, peptides and functional RNA molecules. Generally, the gene product encoded by the nucleic acid molecule is the desired gene product to be supplied to a subject. Examples of such gene products include proteins, peptides, glycoproteins and lipoproteins normally produced by an organ of the recipient subject. For example, gene products which may be supplied by way of gene replacement to defective organs in the pancreas include insulin, amylase, protease, lipase, trypsinogen, chymotrypsinogen, carboxypeptidase, ribonuclease, deoxyribonuclease, triacylglycerol lipase, phospholipase $A_2$, elastase, and amylase; gene products normally produced by the liver include blood clotting factors such as blood clotting Factor VIII and Factor IX, UDP glucuronyl transferae, ornithine transcarbanoylase, and cytochrome p450 enzymes, and adenosine deaminase, for the processing of serum adenosine or the endocytosis of low density lipoproteins; gene products produced by the thymus include serum thymic factor, thymic humoral factor, thymopoietin, and thymosin $α_1$; gene products produced by the digestive tract cells include gastrin, secretin, cholecystokinin, somatostatin, serotinin, and substance P.

Alternatively, the encoded gene product is one, which induces the expression of the desired gene product by the cell (e.g., the introduced genetic material encodes a transcription factor, which induces the transcription of the gene product to be supplied to the subject).

In still another embodiment, the recombinant gene can provide a heterologous protein, e.g., not native to the cell in which it is expressed. For instance, various human MHC components can be provided to non-human cells to support engraftment in a human recipient. Alternatively, the transgene is one, which inhibits the expression or action of a donor MHC gene product.

A nucleic acid molecule introduced into a cell is in a form suitable for expression in the cell of the gene product encoded by the nucleic acid. Accordingly, the nucleic acid molecule includes coding and regulatory sequences required for transcription of a gene (or portion thereof) and, when the gene product is a protein or peptide, translation of the gene acid molecule include promoters, enhancers and polyadenylation signals, as well as sequences necessary for transport of an encoded protein or peptide, for example N-terminal signal sequences for transport of proteins or peptides to the surface of the cell or secretion.

Nucleotide sequences which regulate expression of a gene product (e.g., promoter and enhancer sequences) are selected based upon the type of cell in which the gene product is to be expressed and the desired level of expression of the gene product. For example, a promoter known to confer cell-type specific expression of a gene linked to the promoter can be used. A promoter specific for myoblast gene expression can be linked to a gene of interest to confer muscle-specific expression of that gene product. Muscle-specific regulatory elements, which are known in the art, include upstream regions from the dystrophin gene (Klamut et al., (1989) *Mol. Cell. Biol.* 9: 2396), the creatine kinase gene (Buskin and Hauschka, (1989) *Mol. Cell. Biol.* 9: 2627) and the troponin gene (Mar and Ordahl, (1988) *Proc. Natl. Acad. Sci. USA.* 85: 6404). Regulatory elements specific for other cell types are known in the art (e.g., the albumin enhancer for liver-specific expression; insulin regulatory elements for pancreatic islet cell-specific expression; various neural cell-specific regulatory elements, including neural dystrophin, neural enolase and A4 amyloid promoters).

Alternatively, a regulatory element, which can direct constitutive expression of a gene in a variety of different cell types, such as a viral regulatory element, can be used. Examples of viral promoters commonly used to drive gene expression include those derived from polyoma virus, Adenovirus 2, cytomegalovirus and Simian Virus 40, and retroviral LTRs.

Alternatively, a regulatory element, which provides inducible expression of a gene linked thereto, can be used. The use of an inducible regulatory element (e.g., an inducible promoter) allows for modulation of the production of the gene product in the cell. Examples of potentially useful inducible regulatory systems for use in eukaryotic cells include hormone-regulated elements (e.g., see Mader, S. and White, J. H. (1993) *Proc. Natl. Acad. Sci. USA* 90: 5603-5607), synthetic ligand-regulated elements (see, e.g., Spencer, D. M. et al. 1993) *Science* 262: 1019-1024) and ionizing radiation-regulated elements (e.g., see Manome, Y. Et al. (1993) *Biochemistry* 32: 10607-10613; Datta, R. et al. (1992) *Proc. Natl. Acad. Sci. USA* 89: 1014-10153). Additional tissue-specific or inducible regulatory systems, which may be developed, can also be used in accordance with the invention.

There are a number of techniques known in the art for introducing genetic material into a cell that can be applied to modify a cell of the invention.

In one embodiment, the nucleic acid is in the form of a naked nucleic acid molecule. In this situation, the nucleic acid molecule introduced into a cell to be modified consists only of the nucleic acid encoding the gene product and the necessary regulatory elements.

Alternatively, the nucleic acid encoding the gene product (including the necessary regulatory elements) is contained within a plasmid vector. Examples of plasmid expression vectors include CDM8 (Seed, B. (1987) *Nature* 329: 840) and pMT2PC (Kaufman, et al. (1987) *EMBO J.* 6: 187-195).

In another embodiment, the nucleic acid molecule to be introduced into a cell is contained within a viral vector. In this situation, the nucleic acid encoding the gene product is inserted into the viral genome (or partial viral genome). The regulatory elements directing the expression of the gene product can be included with the nucleic acid inserted into the viral genome (i.e., linked to the gene inserted into the viral genome) or can be provided by the viral genome itself.

Naked nucleic acids can be introduced into cells using calcium phosphate mediated transfection, DEAE-dextran mediated transfection, electroporation, liposome-mediated transfection, direct injection, and receptor-mediated uptake.

Naked nucleic acid, e.g., DNA, can be introduced into cells by forming a precipitate containing the nucleic acid and calcium phosphate. For example, a HEPES-buffered saline solution can be mixed with a solution containing calcium chloride and nucleic acid to form a precipitate and the precipitate is then incubated with cells. A glycerol or dimethyl sulfoxide shock step can be added to increase the amount of nucleic acid taken up by certain cells. $CaPO_4$-mediated transfection can be used to stably (or transiently) transfect cells and is only applicable to in vitro modification of cells. Protocols for $CaPO_4$-mediated transfection can be found in Current Protocols in Molecular Biology, Ausubel, F. M. et al. (eds.) Greene Publishing Associates, (1989), Section 9.1 and in Molecular Cloning: A Laboratory Manual, 2nd Edition, Sambrook et al. Cold Spring Harbor Laboratory Press, (1989), Sections 16.32-16.40 or other standard laboratory manuals.

Naked nucleic acid can be introduced into cells by forming a mixture of the nucleic acid and DEAE-dextran and incubating the mixture with the cells. A dimethylsulfoxide or chloroquine shock step can be added to increase the amount of nucleic acid uptake. DEAE-dextran transfection is only applicable to in vitro modification of cells and can be used to introduce DNA transiently into cells but is not preferred for creating stably transfected cells. Thus, this method can be used for short-term production of a gene product but is not a method of choice for long-term production of a gene product. Protocols for DEAE-dextran-mediated transfection can be found in Current Protocols in Molecular Biology, Ausubel, F. M. et al. (eds.) Greene Publishing Associates (1989), Section 9.2 and in Molecular Cloning: A Laboratory Manual, 2nd Edition, Sambrook et al. Cold Spring Harbor Laboratory Press, (1989), Sections 16.41-16.46 or other standard laboratory manuals.

Naked nucleic acid can also be introduced into cells by incubating the cells and the nucleic acid together in an appropriate buffer and subjecting the cells to a high-voltage electric pulse. The efficiency with which nucleic acid is introduced into cells by electroporation is influenced by the strength of the applied field, the length of the electric pulse, the temperature, the conformation and concentration of the DNA and the ionic composition of the media. Electroporation can be used to stably (or transiently) transfect a wide variety of cell types and is only applicable to in vitro modification of cells. Protocols for electroporating cells can be found in Current Protocols in Molecular Biology, Ausubel F. M. et al. (eds.) Greene Publishing Associates, (1989), Section 9.3 and in Molecular Cloning: A Laboratory Manual, 2nd Edition, Sambrook et al. Cold Spring Harbor Laboratory Press, (1989), Sections 16.54-16.55 or other standard laboratory manuals.

Another method by which naked nucleic acid can be introduced into cells includes liposome-mediated transfection (lipofection). The nucleic acid is mixed with a liposome suspension containing cationic lipids. The DNA/liposome complex is then incubated with cells. Liposome mediated transfection can be used to stably (or transiently) transfect cells in culture in vitro. Protocols can be found in Current Protocols in Molecular Biology, Ausubel F. M. et al. (eds.) Greene Publishing Associates, (1989), Section 9.4 and other standard laboratory manuals. Additionally, gene delivery in vivo has been accomplished using liposomes. See for example Nicolau et al. (1987) *Meth. Enz.* 149:157-176; Wang and Huang (1987) *Proc. Natl. Acad. Sci. USA* 84:7851-7855; Brigham et al. (1989) *Am. J. Med. Sci* 298:278; and Gould-Fogerite et al. (1989) *Gene* 84:429-438.

Naked nucleic acid can also be introduced into cells by directly injecting the nucleic acid into the cells. For an in vitro culture of cells, DNA can be introduced by microinjection. Since each cell is microinjected individually, this approach is very labor intensive when modifying large numbers of cells. However, a situation wherein microinjection is a method of choice is in the production of transgenic animals (discussed in greater detail below). In this situation, the DNA is stably introduced into a fertilized oocyte, which is then allowed to develop into an animal. The resultant animal contains cells carrying the DNA introduced into the oocyte. Direct injection has also been used to introduce naked DNA into cells in vivo (see e.g., Acsadi et al. (1991) *Nature* 332:815-818; Wolff et al. (1990) *Science* 247:1465-1468). A delivery apparatus (e.g., a "gene gun") for injecting DNA into cells in vivo can be used. Such an apparatus is commercially available (e.g., from Bio-Rad).

Naked nucleic acid can be complexed to a cation, such as polylysine, which is coupled to a ligand for a cell-surface receptor to be taken up by receptor-mediated endocytosis (see for example Wu, G. and Wu, C. H. (1988) *J. Biol. Chem.* 263:14621; Wilson et al. (1992) *J. Biol. Chem.* 267: 963-967; and U.S. Pat. No. 5,166,320). Binding of the nucleic acid-ligand complex to the receptor facilitates uptake of the DNA by receptor-mediated endocytosis. Receptors to which a DNA-ligand complex has targeted include the transferrin receptor and the asialoglycoprotein receptor. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci. USA* 88: 8850; Cristiano et al. (1993) *Proc. Natl. Acad. Sci. USA* 90: 2122-2126). Receptor-mediated DNA uptake can be used to introduce DNA into cells either in vitro or in vivo and, additionally, has the added feature that DNA can be selectively targeted to a particular cell type by use of a ligand which binds to a receptor selectively expressed on a target cell of interest.

Generally, when naked DNA is introduced into cells in culture (e.g., by one of the transfection techniques described above) only a small fraction of cells (about 1 out of $10^5$) typically integrate the transfected DNA into their genomes (i.e., the DNA is maintained in the cell episomally). Thus, in order to identify cells, which have taken up exogenous DNA, it is advantageous to transfect nucleic acid encoding a selectable marker into the cell along with the nucleic acid(s) of interest. Preferred selectable markers include those, which confer resistance to drugs such as G418, hygromycin and methotrexate. Selectable markers may be introduced on the same plasmid as the gene(s) of interest or may be introduced on a separate plasmid.

A preferred approach for introducing nucleic acid encoding a gene product into a cell is by use of a viral vector containing nucleic acid, e.g., a cDNA, encoding the gene product. Infection of cells with a viral vector has the advantage that a large proportion of cells receive the nucleic acid which can obviate the need for selection of cells which have received the nucleic acid. Additionally, molecules encoded within the viral vector, e.g., a cDNA contained in the viral vector, are expressed efficiently in cells which have taken up viral vector nucleic acid and viral vector systems can be used either in vitro or in vivo.

Defective retroviruses are well characterized for use in gene transfer for gene therapy purposes (for review see Miller, A. D. (1990) *Blood* 76: 271). A recombinant retrovirus can be constructed having a nucleic acid encoding a gene product of interest inserted into the retroviral genome. Additionally, portions of the retroviral genome can be removed to render the retrovirus replication defective. The replication defective retrovirus is then packaged into virions, which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM, which are well known to those skilled in the art. Examples of suitable packaging virus lines include ψCrip, ψCrip, ψ2 and ψAm. Retroviruses have been used to introduce a variety of genes into many different cell types, including epithelial cells endothelial cells, lymphocytes, myoblasts, hepatocytes, bone marrow cells, in vitro and/or in vivo (see for example Eglitis, et al. (1985) Science 230: 1395-1398; Danosand Mulligan (1988) *Proc. Natl. Acad. Sci. USA* 85: 6460-6464; Wilson et al. (1988) *Proc. Natl. Acad. Sci USA* 85:3014-3018; Armentano et al., (1990) Proc. Natl. Acad. Sci. USA 87: 6141-6145; Huber et al. (1991) Proc. Natl. Acad. Sci. USA 88: 8039-8043; Feri et al. (1991) Proc. Natl. Acad. Sci. USA 88:8377-8381; Chowdhury et al. (1991) *Science* 254: 1802-1805; van Beusechem et al. (1992) Proc. Natl. Acad. Sci USA 89:7640-7644; Kay et al. (1992) *Human Gene Therapy* 3:641-647; Dai et al. (1992) *Proc. Natl. Acad. Sci. USA* 89:10892-10895; Hwu et al. (1993) J. Immunol. 150:4104-4115; U.S. Pat. No. 4,868,116; U.S. Pat. No. 4,980, 286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616; Rosenfeld et al. (1991) *Science* 252:431-434; and Rosenfeld et al. (1992) *Cell* 68:143-155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci. USA* 89: 6482-6486), hepatocytes (Herz and Gerard (1993) *Proc. Natl. Acad. Sci. USA* 90: 2812-2816) and muscle cells (Quantin et al. (1992) *Proc. Natl. Acad. Sci. USA* 89: 2581-2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol* 57: 267). Most replication-defective adenoviral vectors currently in use are deleted for all or parts of the viral E1 and E3 genes but retain as much as 80% of the adenoviral genetic material.

Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics In Micro. And Immunol.* (1992) 158: 97-129). It is also one of the few viruses that may integrate its DNA into non-dividing cells, and exhibits a high frequency of stable integration (see for example Flotte et al. (1992) *Am. J. Respir. Cell. Mol. Biol.* 7: 349-356; Samulski et al. (1989) *J. Virol.* 63:3822-3828; and McLaughlin et al. (1989) J. Virol. 62: 1963-1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5: 3251-3260 can be used to introduce DNA into cells. A variety of nucleic acids have been introduced into different cell types using AAV vectors (see for example Hermonat et al. (1984) *Proc. Natl. Acad. Sci. USA* 81: 6466-6470; Tratschin et al. (1985) *Mol. Cell. Biol.* 4: 2072-2081; Wondisford et al. (1988) *Mol. Endocrinol.* 2:32-39; Tratschin et al. (1984) *J. Virol.* 51: 611-619; and Flotte et al. (1993) J. Biol. Chem. 268: 3781-3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product, such as an enzymatic assay. If the gene product of interest to be interest to be expressed by a cell is not readily assayable, an expression system can first be optimized using a reporter gene linked to the regulatory elements and vector to be used. The reporter gene encodes a gene product, which is easily detectable and, thus, can be used to evaluate efficacy of the system. Standard reporter genes used in the art include genes encoding β-galactosidase, chloramphenicol acetyl transferase, luciferase and human growth hormone.

When the method used to introduce nucleic acid into a population of cells results in modification of a large proportion of the cells and efficient expression of the gene product by the cells (e.g., as is often the case when using a viral expression vector), the modified population of cells may be used without further isolation or subcloning of individual cells within the population. That is, there may be sufficient production of the gene product by the population of cells such that no further cell isolation is needed. Alternatively, it may be desirable to grow a homogenous population of identically modified cells from a single modified cell to isolate cells, which efficiently express the gene product. Such a population of uniform cells can be prepared by isolating a single modified cell by limiting dilution cloning followed by expanding the single cell in culture into a clonal population of cells by standard techniques.

According to the methods of the present invention, the ex-vivo expanded cells are implanted into a subject in need of thereof. In one embodiment, the subject is a human. As used herein, the phrase "in need thereof" indicates the state of the subject, wherein enhancement of one or more organs or tissues is desirable. Such a state can include, but is not limited to, subjects suffering from stroke, diabetes, myocardial disease, renal disease, ischemic disease, primary liver disease such as primary biliary cirrhosis, hepatic cancer, primary sclerosing cholangitis, autoimmune chronic hepatitis, alcoholic liver disease and infectious disease such as hepatitis C, secondary conditions such as the hepatic stage of parasitic infections (helminthes, etc), drug and chemical toxicity, pancreatic diseases such as acute and chronic pancreatitis, hereditary pancreatitis, pancreatic cancer and diabetes. In any of the methods of this aspect of the present invention, the donor and the recipient of the stem and/or progenitor cells can be a single individual or different individuals, for example, allogeneic or xenogeneic individuals. When allogeneic transplantation is practiced, regimes for reducing implant rejection and/or graft vs. host disease, as well know in the art, should be undertaken. Such regimes are currently practiced in human therapy. Most advanced regimes are disclosed in publications by Slavin S. et al., e.g., J Clin Immunol (2002) 22: 64, and J. Hematother Stem Cell Res (2002) 11: 265), Gur H. et al. (Blood (2002) 99: 4174), and Martelli M F et al, (Semin Hematol (2002) 39: 48), which are incorporated herein by reference.

The methods described hereinabove for ex-vivo expanding stem cells populations can result, inter alia, in an expanded population of stem cells.

Thus, further according to an aspect of the present invention there is provided an ex-vivo expanded population of hematopoietic stem cells which comprises a plurality of cells characterized by an enhanced proportion of cells being reselectable $CD34^+$ cells. In one embodiment, the hematopoietic stem cells are derived from a source selected from the group consisting of bone marrow, peripheral blood and neonatal umbilical cord blood. In another embodiment, the population of cells has a single genetic background. Cell surface expression of the CD34 and/or Lin markers can be determined, for example, via FACS analysis or immunohistological staining techniques. A self renewal potential of the stem cells can be determined in-vitro by long term colony formation (LTC-CFUc), as is further exemplified in the Examples section that follows, or by in-vivo engraftment in the SCID-Hu mouse model. The SCID-Hu mouse model employs C.B-17 scid/scid (SCID) mice transplanted with human fetal thymus and liver tissue or fetal BM tissue and provides an appropriate model for the evaluation of putative human hematopoietic stem cells. Because of the reconstitution of the SCID mice with human fetal tissue, the model affords the proliferation of stem cells, in this case human hematopoietic stem cells to proliferate, and function in the hematopoietic microenvironment of human origin. Mice are typically irradiated, then delivered stem cells into the grafts, and reconstitution is measured by any number of methods, including FACS and immunohistochemistry of repopulated organs (Humeau L., et al. Blood (1997) 90:3496).

Additionally, the methods described hereinabove can be utilized to produce transplantable hematopoietic cell preparations, such that according to yet another aspect of the present invention there is provided a therapeutic ex vivo cultured stem cell population, which comprises undifferentiated hematopoietic cells expanded ex-vivo as described hereinabove. It will be appreciated, in the context of the present invention, that the therapeutic stem cell population can be provided along with the culture medium containing, isolated from the culture medium, and combined with a pharmaceutically acceptable carrier. Hence, cell populations of the invention can be administered in a pharmaceutically acceptable carrier or diluent, such as sterile saline and aqueous buffer solutions. The use of such carriers and diluents is well known in the art.

In one preferred embodiment, the expanded hematopoietic cell population is provided along with mesenchymal cells, preferably the mesenchymal cells of the co-culture, as described hereinabove. In another embodiment, the hematopoietic cell population is provided without mesenchymal cells. Methods for separation of mesenchymal cells and hematopoietic cells are well known in the art, and include, but are not limited to, washing (mesenchymal cells adhere to plastic) and affinity separation (according to mesenchymal and/or hematopoietic cell markers) by chromatography, batch separation and/or FACS. Purity of a cell preparation can be assessed according to similar criteria.

The ability of the methods of the present invention to inhibit differentiation of stem cells can be further used in various technical applications:

According to a further aspect of the present invention there is provided a method of preserving stem cells. In one embodiment, the method is effected by handling the stem cell in at least one of the following steps: harvest, isolation and/or storage, in a presence of a mesenchymal cell culture, under conditions allowing expanding and at the same time inhibiting differentiation of the stem cells According to still a further aspect of the present invention there is provided a cells collection/culturing bag. The cells collection/culturing bag of the present invention is supplemented with an effective amount of at least one of the above described agents, and mesenchymal stem cells, or supernatant or conditioned medium from mesenchymal stem cell culture. Methods for the preparation of such conditioned medium or supernatant are well known in the art, and are disclosed in detail in U.S. Pat. Nos. 6,875,430 and 6,368,636 to McIntosh et al.

The methods described hereinabove for ex-vivo expanding and at the same time inhibiting differentiation of a population of stem and/or progenitor cells into stem cells can result, inter alia, in an expanded population of stem cells having a specific stem cell phenotype.

It will be appreciated, in the context of the present invention, that the therapeutic stem cell population can be provided along with the culture medium containing growth factors, isolated from the culture medium, and combined with a pharmaceutically acceptable carrier. Hence, cell populations of the invention can be administered in a pharmaceutically acceptable carrier or diluent, such as sterile saline and aqueous buffer solutions. The use of such carriers and diluents is well known in the art. Thus, according to another aspect of the present invention, there is provided a pharmaceutical composition comprising cell populations of the invention and a pharmaceutically acceptable carrier.

Methods of administration of cells for treatment of diseases by implantation and repopulation of diseased organs and tissues are well known in the art (for detailed description of such methods see, for example, U.S. Pat. No. 5,843,156 to Slepian et al, and U.S. Pat. No. 5,670,140 to Sherwin et al, both incorporated by reference as if fully set forth herein). In a preferred embodiment, the cells are administered by direct implantation into the damaged organ. In addition to direct implantation of cells, cellular therapy can be also provided via indwelling and external bio-artificial devices, encapsulated cells, and the like.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following.

EXAMPLES

Reference is now made to the following examples, which together with the above descriptions illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683, 202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Experimental Methods

Isolation of mesenchymal cells: Mononuclear cells containing mesenchymal cells from bone marrow were obtained from a hematopoietic cell enriched fraction prepared by negative immuno-depletion of CD3, CD14, CD19, CD38, CD66b, and glycophorin-A positive cells using a commercially available kit (RosetteSep®, StemCell Technologies, Vancouver, BC, Canada), as per manufacturer's instructions. This procedure yields a highly purified population of CD34+CD38− cells [Thomas T E, Fairhurst M A, Lansdorp P M Rapid single step immunomagnetic isolation of highly enriched primitive human hematopoietic progenitors. Blood 90 Suppl. 1 347b, 1997 (abst)]. The immuno-depleted cells were harvested, and then either further separated by layering on a Ficoll-Paque (Amersham-Pharmacia, Piscataway, N.J., USA) density gradient column (1.077 g/cm$^3$) and centrifuged at 400×g for 30 minutes, or cultured without further separation. The collected cells were plated in T75 non-coated tissue culture flasks (Nunc) at a concentration of 2×10$^5$ cells/ml, in expansion medium containing: low glucose DMEM and 20% Fetal Bovine Serum (FBS, Hyclone, Logan, Utah, USA) supplemented with or without 10 ng/ml bFGF (Pepro Tech Inc, Rocky Hill N.J.), 0.05 mg/ml gentamicin (Sigma Inc., St. Louis, Mo.) and 2 mM L-glutamine (Biological Industries, Israel). Selected cells were allowed to adhere for 3-4 days and non-adherent cells were washed out with medium changes. Some experiments were initiated as well with the entire MNC fraction.

Alternatively, mesenchymal cells were isolated based on their plastic adherence potential alone, separated from non-adherent cells by washing, collected, and cultured as above.

Maintenance and expansion of mesenchymal cells: When adherent mesenchymal cells reached approximately 80-90% confluence, they were detached with 0.25% trypsin-EDTA (Sigma, Inc. St Louis, Mo.), washed twice in DMEM and 20% Fetal Bovine Serum, with centrifugation, 400 g, 5 min., and re-plated at a 1:2 to 1:1000 dilution under the same culture conditions.

Modulators of cell fate: Where indicated, mesenchymal and stem cells were cultured in the presence of low molecular weight (LMW) modulators of hematopoietic stem cell fate such as copper chelators (PCT/US99/02664; Publication No.: WO 99/40783 and PCT/IL99/00444; Publication No.: WO 00/18885), Nicotinamide (PCT/IL03/00681; Publication No.: WO 2004/016731), SIRT2 inhibitors (U.S. provisional patent application No. 60/587,496, filed Jul. 14, 2004 and PCT IL05/000753), Retinoic acid receptors antagonists (PCT/IL03/00681; Publication No.: WO 2004/016731) and antagonists to PI3-K (PCT/IL2004/000215) to increase the numbers of hematopoietic renewal cells with high differentiation potential while co-cultured with mesenchymal cells.

Purification of CDD133+ and CD34+ cells—To purify CDD133+ or CD34$^+$ cells, the mononuclear cell fraction was subjected to two cycles of immuno-magnetic separation using the "MiniMACS or Clinimax CD34 progenitor cell isolation kit" (Miltenyi Biotec, Aubun, Calif.) following the manufacturer's recommendations. The purity of the CD34$^+$ population obtained ranged from 95% to 98% as evaluated by flow cytometry.

Ex vivo expansion of CD34$^+$ cells—Purified CD34$^+$ cells were cultured in 24-well Costar Cell Culture Clusters (Corning Inc. Corning, N.Y.) or culture bags at 10$^4$ cells/mL in alpha medium supplemented with 10% fetal bovine serum (FBS) (Biological Industries) and the following human recombinant cytokines: Thrombopoietin (TPO), interleukin-6 (IL-6) and FLT-3 ligand, at final concentration of 50 ng/mL each +/−IL-3 at 20 ng/ml (all from Perpo Tech, Inc. Rocky Hill, N.J.), with and without Nicotinamide. The cultures were incubated at 37° C. in humidified atmosphere of 5% CO$_2$ in air.

At weekly intervals, cultures were either topped or semi-depopulated and supplemented with fresh medium, serum and cytokines. At various time points, cells were harvested, counted following staining with trypan blue, and cell morphology was determined on cytospin (Shandon, UK)-prepared smears stained with May-Grunwald/Giemsa solutions.

Mesenchymal hematopoietic co-cultures: Mesenchymal cultures were established as described above. After reaching confluence, the mesenchymal medium was discarded and replaced with fresh, hematopoietic supportive medium containing early acting or early and late acting cytokines, and hematopoietic cells selected from; cord blood, bone marrow, placenta or peripheral blood mononuclear cells or purified progenitor cells (CD34+ or CD133+ cells), with or without a modulator of cell fate. Mononuclear or purified stem and/or progenitor cells were isolated and prepared for ex-vivo culture as previously described (see, above, or, for example, PCT IL05/000753). At different intervals the non-adherent cells were harvested, analyzed for hematopoietic potential by functional analysis (clonogenic assay, CFU, etc), and re-cultured in a stroma-free medium. The stromal layer was then re-supplemented with fresh hematopoietic supportive medium (medium including 10% FCS, SCF, TPO, FLT3, and IL6). This process was repeated several times during two to six weeks co-culture duration (as on day 10, day 14, etc). At the end of the process, all cultures derived from the same experimental group were combined and analyzed for hematopoietic potential (cell surface markers CD34+, CD34+/38+, and CD34+lin−) to demonstrate the improved quality of hematopoietic cell recovered from the experimental group supplemented with the modulators of stem cell fate.

Immunophenotyping: At different time points the cells were detached with 1 mM EDTA (15', 37° C.). The detached cells were washed with a PBS solution containing 1% BSA, and stained (at 4° C. for 30 min) with either fluorescein isothiocyanate (FITC) or phycoerythrin (PE)-conjugated antibodies: mesenchymal markers 105 PE, 105 FITC (Serotec), 73 PE, and 49b PE, and other, non-mesenchymal markers such as 45 FITC, 14 FITC, HLA-DR FITC (BD Biosciences Pharmngen), 34 PE (Dako, Carpenteria, Calif., USA), HLA class1 PE, (BD Biosciences Pharmingen, San Diego Calif.). The cells were then washed in the above buffer and analyzed using a FACScalibur® flow cytometer (Becton Dickinson and Co, San Jose, Calif., USA). Cells were passed at a rate of about 1000 cells/second, using saline as the sheath fluid. A 488 nm argon laser beam served as the light source for excitation. Emission of ten thousand cells was measured using logarithmic amplification and calculated using the cellQuest software. Background noise was determined using isotype control stained cells. Arithmetic Mean Fluorescence Channel (MFC) of the negative and positive populations and the stained cells to noise (S/N) ratio were calculated.

Assay for Colony Forming Units (CFU)—Cells were cloned in semi-solid, methylcellulose-containing medium supplemented with 2 IU/mL erythropoietin (Eprex, Cilag AG Int., Switzerland), stem cell factor and IL-3, both at 20 ng/mL, G-CSF and GM-CSF, both at 10 ng/mL (all from Pepro Tech, Rocky Hill, N.J.). Cultures were incubated for 14 days at 37° C. in humidified atmosphere of 5% $CO_2$ in air.

Experimental Results

Example I

Nicotinamide Enhances Expansion of Hematopoietic Stem Cells in Co-Culture with Mesenchymal Cells Modulators of cell fate, such as nicotinamide, have been shown to enhance the proliferation of stem cells ex-vivo, while inhibiting their differentiation, allowing long term expansion of undifferentiated stem cells of various origins. In order to determine whether such modulators of cell fate can exert a similar effect on hematopoietic stem cells co-cultured with mesenchymal cells, mononuclear cells were grown ex-vivo in co-culture with a mesenchymal feeder layer, with or without the addition of nicotinamide (5 mM).

Tables 1-4 represent the results of four separate experiments, demonstrating the expansion of populations of undifferentiated hematopoietic stem cells in 3 week cultures of mononuclear cells co-cultured with mesenchymal cells. As the tables clearly demonstrate, addition of nicotinamide (5 mM) to the culture medium results in a significant synergistic increase in the proportion of the undifferentiated hematopoietic cell populations, as indicated by analysis of cell surface markers (CD34+, CD34+/38+, and CD34+/lin−) and functional analysis (CFUc). When compared with the number of total nucleated cells, Tables 3 and 4 show up to a 2.3 times greater expansion of stem cells (CD34+) as compared with cocultures without nicotinamide (5.3% vs 4%, table 3; 1.5% vs 0.65, table 4).

TABLE 1

Mesenchymal− MNC Co-culture at 21 days +/− Nicotinamide 5 mM

| | TNC × $10^6$ | CD34+CD38− ($\times 10^4$) | CD34+Lin− ($\times 10^4$) |
|---|---|---|---|
| Mesenchymal+ MNC Co-culture | 422 | 138 | 3.6 |
| Mesenchymal+ MNC Co-culture + Nicotinamide | 309 | 304 | 25 |

TABLE 2

Mesenchymal− MNC Co-culture at 21 days +/− Nicotinamide 5 mM

| | TNC × $10^6$ | CD34+CD38− ($\times 10^4$) | CD34+Lin− ($\times 10^4$) |
|---|---|---|---|
| Mesenchymal+ MNC Co-culture | 422 | 581 | 230 |
| Mesenchymal+ MNC Co-culture + Nicotinamide | 309 | 1238 | 689 |

TABLE 3

Mesenchymal− MNC Co-culture at 21 days +/− Nicotinamide 5 mM

| | TNC × $10^6$ | CD34+ ($\times 10^4$) | CD34+/ TNC | CD34+ CD38− ($\times 10^4$) | CPU ($\times 10^3$) |
|---|---|---|---|---|---|
| Mesenchymal+ MNC Co-culture | 220 | 880 | 4% | 37 | 2640 |
| Mesenchymal+ MNC Co-culture + Nicotinamide | 292 | 1553 | 5.3% | 82 | 4331 |

TABLE 4

Mesenchymal− MNC Co-culture at 21 days +/− Nicotinamide 5 mM

| | TNC × $10^6$ | CD34+ ($\times 10^4$) | CD34+/ TNC | CD34+ CD38− ($\times 10^4$) | CD34+ Lin− ($\times 10^4$) |
|---|---|---|---|---|---|
| Mesenchymal+ MNC Co-culture | 224 | 146 | 0.65% | 11 | 0.07 |
| Mesenchymal+ MNC Co-culture + Nicotinamide | 144 | 216 | 1.5% | 63 | 1.54 |

TNC = Total Nucleated Cells
MNC = Mononuclear Cells

Thus, the results brought herein clearly illustrate the synergistic enhancement of expansion of hematopoietic stem cells co-cultured with mesenchymal cells, in the presence of modulators of cell fate.

Example 2

Nicotinamide Enhances Expression of CXCR4 in Hematopoietic Stem Cells in Co-Culture with Mesenchymal Cells CXCR4 has been identified as the cell surface receptor for the stromal cell-derived factor (SDF)-1 (CXCL12), and it's expression has been shown to be important to engraftment and tissue homing of hematopoietic progenitors. Induction of CXCR4 expression in hematopoietic stem cells results in increased sensitivity to lower levels of SDF-1, increased migration of the cells to SDF-1, improved proliferation and survival of the hematopoietic stem cells in-vitro and in-vivo, and improved engraftment potential of the induced cells. Similarly, it has been shown that blockage of CXCR4 with specific antibodies prevents engraftment of hematopoietic stem cells (Brenner, et al Stem Cells 2004; 22:1128-33; Kahn et al, Blood, 2004; 103:2942-49; Peled et al, Science 1999; 283:845-48). In order to investigate the effect of modulators of cell fate on CXCR4 expression in hematopoietic stem cells in co-culture with mesenchymal cells, the population of CD34+/CXCR4+ cell in co-cultured cells was detected and quantified by double staining with PE labeled CD34 and FITC labeled CXCR4.

TABLE 5

CXCR4 in Mesenchymal– MNC Co-culture at 21 days +/– Nicotinamide 5 mM

|  | Exp 1 | Exp 2 |
|---|---|---|
| Co-culture+ Cytokines | $36 \times 10^4$ | $150 \times 10^4$ |
| Co-culture+ Cytokines+ Nicotinamide | $65 \times 10^4$ | $200 \times 10^4$ |
| % Increase | 80% | 33% |

Number of CD34+CXCR4+ cells were calculated as following: % CD34+CXCR4+ × Number of cells in culture/100.

Table 5 shows the results of two representative experiments illustrating the synergistic effect of nicotinamide on three week cultures of hematopoietic stem cells, prepared and co-cultured with mesenchymal cells as described in Example 1 hereinabove. As is demonstrated in Table 5, exposure of the hematopoietic-mesenchymal co-cultures to nicotinamide significantly enhances CXCR4 expression, which is consistent with the preferential, synergistic expansion, and at the same time, inhibition of differentiation of hematopoietic cells observed with nicotinamide and co-culturing with mesenchymal cells. This enhanced CXCR4 expression contributes to the enhanced engraftment potential of the expanded, undifferentiated hematopoietic stem cells.

Example 3

Nicotinamide Enhances Expansion and Long-Term Clonogenic Potential in Hematopoietic Stem Cells in Co-Culture with Mesenchymal Cells In order to determine the long-term effects of modulators of cell fate on the long-term engraftment potential of hematopoietic stem cells, CFUc, CD34+ and CD34+/CD38– cells were assessed in co-cultured cells at 8 weeks (5 weeks after removal of nicotinamide from the medium).

TABLE 6

Long-Term Mesenchymal– MNC Co-culture (21 days +/– Nicotinamide 5 mM followed by 5 weeks cytokines only)

|  | CFUc (cumulative) | CD34+ cells (cumulative) | CD34+/ CD38– (%) |
|---|---|---|---|
| Co-culture + Cytokines | $13 \times 10^6$ | $112 \times 10^6$ | 0.6 |
| Co-culture + Cytokines + Nicotinamide | $28 \times 10^6$ | $264 \times 10^6$ | 6.3 |
| Fold Increase (%) | 215% | 235% | 1050% |

The effects of co-culturing with mesenchymal cells and modulators of cells fate on engraftment potential of the expanded hematopoietic stem cells can be assessed in the short term, by using cells soon after expansion, or in the long term, after removal of the cell fate modulators. Thus, the short term (three weeks) exposure to nicotinamide could either exert a lasting effect following removal of nicotinamide from the medium, or a short-term effect only, which would be expected to diminish with time after removal of nicotinamide.

Table 6 illustrates the long-term effects of co-culturing hematopoietic stem cells (from bone marrow) with mesenchymal cells and three weeks exposure to 5 mM nicotinamide. The mononuclear cell fraction, prepared as described above, was expanded in co-culture with mesenchymal cells in medium supplemented with cytokines and 5 mM nicotinamide, as described hereinabove, for 21 days. After 21 days, the medium was replaced with medium supplemented with cytokines only, and expansion in co-cultures continued for another 5 weeks. At 8 weeks, the expanded cells were assessed for hematopoietic stem cell markers (CD34+ and CD34+/CD38–), and for engraftment potential (CFUc), as described hereinabove.

Analysis of the long term cultures demonstrates the superior expansion of hematopoietic progenitor cells and colonogenic potential (CFUc) in long-term mesenchymal co-cultures exposed short-term to nicotinamide, as compared with mesenchymal co-cultures exposed short-term to cytokines only during this period. Thus, the results brought hereinabove are of great significance for the use of the methods and populations of co-cultured, expanded stem cells of the present invention for transplantation, engraftment, and organ and tissue regeneration. The results clearly indicate that exposure of stem cells in co-culture with mesenchymal cells to modulators of cell fate capable of preferentially expanding stem cells while at the same time inhibiting their differentiation (such as nicotinamide, TEPA, and the like), synergistically enhances expansion of the stem cell fraction and increases the engraftment potential of the expanded cells. Further, the preferential expansion of stem cells, and superior engraftment potential persist in long term culture, weeks after removal of the modulator of cell fate.

In conclusion, co-culture of hematopoietic stem cells with mesenchymal cells, in the presence of modulators of cell fate, such as nicotinamide, results in synergistic expansion of undifferentiated late progenitor cells (CD34+ cells), as well as that of stem/early progenitor cells (CD34+CD38–, CD34+ Lin–, and CFUc) and induction of effectors of engraftment potential in renewable stem cell populations (CXCR4), as compared with cells co-cultured without added modulators of cell fate.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of expanding and at the same time inhibiting differentiation of a population of CD 133+ hematopoietic stem cells, the method comprising selecting a population of CD133+ hematopoietic stem cells, ex-vivo co-culturing the selected hematopoietic stem cells with an amount of mesenchymal cells sufficient for feeder layer production under conditions which allow expanding and at the same time inhibiting differentiation of at least a portion of the CD133+ hematopoietic stem cells, wherein said conditions comprise culturing cells in the presence of serum and nicotinamide or a nicotinamide analog selected from the group consisting of benzamide, nicotinethioamide, nicotinic acid and α-amino-3-indolepropionic acid for at least three weeks;

thereby expanding and at the same time inhibiting differentiation of said population of said CD133+ hematopoietic stem cells.

2. The method of claim 1, wherein said mesenchymal cells are mesenchymal stem cells.

3. The method of claim 1, wherein said mesenchymal cells are bone marrow-derived mesenchymal cells.

4. The method of claim 1, wherein said mesenchymal cells are provided as a feeder layer of cultured mesenchymal cells.

5. The method of claim 1, wherein said hematopoietic stem cells are derived from a source selected from the group consisting of umbilical cord blood cells, mobilized peripheral blood cells, bone marrow cells.

6. The method of claim 1, wherein said hematopoietic stem cells are derived from bone marrow or peripheral blood.

7. The method of claim 1, wherein said hematopoietic stem cells are derived from neonatal umbilical cord blood.

8. The method of claim 1, wherein said hematopoietic stem cells are derived from a mononuclear cell fraction.

9. The method of claim 1, wherein said hematopoietic stem cells are cultured in the presence of said nicotinamide or nicotinamide analog for three weeks and then further cultured without said nicotinamide or nicotinamide analog for at least 5 weeks.

10. The method of claim 1, wherein said CD 133+ hematopoietic stem cell population is further enriched by selecting CD34+/CD38− cells prior to said co-culturing.

11. The method of claim 1, wherein said conditions further comprise providing the cells with nutrients and cytokines.

12. A method of transducing expanded, undifferentiated hematopoietic stem cells with an exogene, the method comprising:
(a) ex-vivo co-culturing CD133+ hematopoietic stem cells with mesenchymal cells according to the method of claim 1 to thereby obtain expanded, undifferentiated hematopoietic stem cells; and
(b) transducing the expanded, undifferentiated hematopoietic stem cells with an exogene.

13. The method of claim 12, wherein said transducing is effected by a vector comprising the exogene.

14. The method of claim 12, further comprising the stem of transplanting the transduced, expanded undifferentiated hematopoietic stem cells into a recipient.

15. A method of hematopoietic stem cell transplantation into a recipient, the method comprising selecting and ex vivo co-culturing CD133+ hematopoietic stem cells with mesenchymal cells according to the method of claim 1 and transplanting said hematopoietic stem cells into the recipient.

16. The method of claim 15, wherein said transplanting said hematopoietic stem cells is effected together with said co-cultured mesenchymal cells.

17. The method of claim 15, further comprising a step of isolating said hematopoietic stem cells from the co-culture prior to said transplanting.

18. The method of claim 15, wherein said hematopoietic stem cells are cultured in the presence of said nicotinamide or a nicotinamide analog for three weeks and then further cultured without said nicotinamide or nicotinamide analog for at least 5 weeks.

19. A method of tissue regeneration comprising
(a) obtaining CD133+ hematopoietic stem cells from a patient;
(b) selecting and ex vivo expanding and inhibiting differentiation of said hematopoietic stem cells by ex-vivo co-culturing the CD133+ hematopoietic stem cells with mesenchymal cells according to the method of claim 1; and
(c) transplanting said ex-vivo expanded hematopoietic stem cells into a recipient.

20. The method of claim 19, wherein said transplanting said hematopoietic cells is effected together with said co-cultured mesenchymal cells.

21. The method of claim 19, further comprising a step of isolating said ex-vivo expanded hematopoietic stem cells from the co-culture prior to stem cells transplantation.

22. The method of claim 19, wherein said hematopoietic stem and/or mesenchymal cells are derived from said recipient.

23. The method of claim 19, wherein said hematopoietic stem cells are cultured in the presence of said nicotinamide or a nicotinamide analog for three weeks and then further cultured without said nicotinamide or nicotinamide analog for at least 5 weeks.

24. A method of adoptive immunotherapy comprising
(a) obtaining CD133+ hematopoietic stem cells from a patient;
(b) selecting and ex-vivo expanding and inhibiting differentiation of said hematopoietic stem cells by ex-vivo co-culturing the CD133+ hematopoietic stem cells with mesenchymal cells according to the method of claim 1; and
(c) transplanting said ex-vivo expanded hematopoietic stem cells into a recipient.

25. The method of claim 24, wherein said transplanting said hematopoietic cells is effected together with said co-cultured mesenchymal cells.

26. The method of claim 24, further comprising a step of isolating said ex-vivo expanded hematopoietic stem cells from the co-culture prior to hematopoietic stem cells transplantation.

27. The method of claim 24, wherein said hematopoietic stem and/or mesenchymal cells are derived from said recipient.

28. The method of claim 24, wherein said hematopoietic stem cells are cultured in the presence of said nicotinamide or nicotinamide analog for three weeks and then further cultured without said nicotinamide or nicotinamide analog selected for at least 5 weeks.

29. A method of hone marrow transplantation comprising
(a) obtaining CD133+ hematopoietic stem cells from a patient;
(b) selecting and ex rim expanding and inhibiting differentiation of said hematopoietic stem cells by ex-vivo co-culturing the CD133+ hematopoietic stem cells with mesenchymal cells according to the method of claim 1; and
(c) transplanting said ex-vivo expanded hematopoietic stem cells into a recipient.

30. The method of claim 29, wherein said transplanting said cells is effected together with said co-cultured mesenchymal cells.

31. The method of claim 29, further comprising a step of isolating ex-vivo expanded hematopoietic stem cells from the co-culture prior to hematopoietic stem cell transplantation.

32. The method of claim 29, wherein said hematopoietic stem and/or mesenchymal cells are derived from said recipient.

33. The method of claim 29, wherein said hematopoietic stem cells are cultured in the presence of said nicotinamide or nicotinamide analog for three weeks and then further cultured without said nicotinamide or nicotinamide analog for at least 5 weeks.

* * * * *

UNITED STATES PATENT AND TRADEMARK OFFICE
CERTIFICATE OF CORRECTION

| | | |
|---|---|---|
| PATENT NO. | : 8,080,417 B2 | Page 1 of 1 |
| APPLICATION NO. | : 11/606525 | |
| DATED | : December 20, 2011 | |
| INVENTOR(S) | : Peled et al. | |

It is certified that error appears in the above-identified patent and that said Letters Patent is hereby corrected as shown below:

At column 59, claim number 14, line number 41, "further comprising the stem" should read --further comprising the step--.

At column 60, claim number 21, line number 8, "prior to stem cells" should read --prior to hematopoietic stem cells--.

At column 60, claim number 28, line number 40, "nicotinamide analog selected" should read --nicotinamide analog--.

At column 60, claim number 29, line number 45, "ex rim expanding" should read --ex-vivo expanding--.

Signed and Sealed this
Twenty-eighth Day of February, 2012

David J. Kappos
*Director of the United States Patent and Trademark Office*